(12) United States Patent
Mooney et al.

(10) Patent No.: US 12,042,227 B2
(45) Date of Patent: Jul. 23, 2024

(54) SYSTEM FOR ASSESSING TARGET VISIBILITY AND TRACKABILITY FROM EYE MOVEMENTS

(71) Applicant: Burke Neurological Institute, White Plains, NY (US)

(72) Inventors: Scott William Joseph Mooney, New York, NY (US); Glen Prusky, White Plains, NY (US)

(73) Assignee: Burke Neurological Institute, White Plains, NY (US)

( * ) Notice: Subject to any disclaimer, the term of this patent is extended or adjusted under 35 U.S.C. 154(b) by 0 days.

(21) Appl. No.: 18/282,956

(22) PCT Filed: Mar. 28, 2022

(86) PCT No.: PCT/US2022/022150
§ 371 (c)(1),
(2) Date: Sep. 19, 2023

(87) PCT Pub. No.: WO2022/212259
PCT Pub. Date: Oct. 6, 2022

(65) Prior Publication Data
US 2024/0164636 A1    May 23, 2024

Related U.S. Application Data

(60) Provisional application No. 63/167,220, filed on Mar. 29, 2021.

(51) Int. Cl.
*A61B 3/113* (2006.01)
*A61B 3/00* (2006.01)
*A61B 5/16* (2006.01)

(52) U.S. Cl.
CPC ............ *A61B 3/113* (2013.01); *A61B 3/0091* (2013.01); *A61B 5/163* (2017.08)

(58) Field of Classification Search
CPC ........ A61B 3/113; A61B 3/0091; A61B 5/163
(Continued)

(56) References Cited

U.S. PATENT DOCUMENTS

2008/0043201 A1    2/2008   Todd
2012/0019662 A1    1/2012   Maltz
(Continued)

OTHER PUBLICATIONS

International Search Report and Written Opinion dated Jun. 14, 2022 issued in PCT International Application No. PCT/US2022/022150.
(Continued)

*Primary Examiner* — Mohammed A Hasan
(74) *Attorney, Agent, or Firm* — Amster, Rothstein & Ebenstein LLP

(57) ABSTRACT

A system and method for dynamically a visual function of a subject are provided where the system and method account for fixation eye movement(s); saccade eye movement (s); smooth pursuit eye movement(s); optokinetic nystagmus eye movement(s); and/or blink eye movement, the system for dynamically assessing a visual function of a subject is provided, comprising: i) a visual display; ii) an eye-tracking device configured to detect a gaze position of at least one eye of the subject; and updating in real time the appearance of a first stimulus to provide a second stimulus based on at least on of the updated evidence-of-visibility score and the updated evidence-of-trackability score for the first visual stimulus.

20 Claims, 32 Drawing Sheets

(58) Field of Classification Search
USPC ........................................................ 351/209
See application file for complete search history.

(56) References Cited

U.S. PATENT DOCUMENTS

| | | | |
|---|---|---|---|
| 2014/0171756 A1 | 6/2014 | Waldorf et al. | |
| 2016/0167672 A1* | 6/2016 | Krueger | G16H 40/63 |
| | | | 340/576 |
| 2019/0142270 A1* | 5/2019 | Monhart | G06F 3/017 |
| | | | 351/209 |

OTHER PUBLICATIONS

Mooney et al., "Gradiate: A Radial Sweep Approach to Measuring Detailed Contrast Sensitivity Functions from Eye Movements," Journal of Vision, Dec. 28, 2020, 20(13):17, pp. 1-18.

Bahill et al., "Smooth Pursuit Eye Movements in Response to Predictable Target Motions," Vision Res., 1983, vol. 23, No. 12, pp. 1573-1583.

Fehd et al., "Looking at the Center of the Targets Helps Multiple Object Tracking," Journal of Vision, Apr. 28, 2010, 10(4):19, pp. 1-13.

* cited by examiner 204-1

SYSTEM FOR ASSESSING TARGET VISIBILITY AND TRACKABILITY FROM EYE MOVEMENTS

CROSS-REFERENCE TO RELATED APPLICATIONS

This application is a U.S. national stage entry under 35 U.S.C. § 371 of PCT International Patent Application No. PCT/US2022/022150, filed Mar. 28, 2022, which claims benefit of U.S. Provisional Application No. 63/167,220, filed Mar. 29, 2021, the contents of which are hereby incorporated by reference.

FIELD OF THE INVENTION

The invention generally relates to systems and methods for dynamically assessing a visual function of a subject are provided where the system and method account for fixation eye movement(s); saccade eye movement(s); smooth pursuit eye movement(s); optokinetic nystagmus eye movement(s); and/or blink eye movement.

BACKGROUND OF THE INVENTION

Visual stimuli are signals presented on a display monitor, such as a small, localized texture, a full-screen pattern, or a pre-rendered video. A visual stimulus is "visible" to an observer, in an absolute sense, when the observer can become conscious of its distinguishing visual features, such as its position, motion, color, shape, or other visual characteristics, by attending to it. Visual stimuli may be nested within one another: a pre-rendered video can be considered a single visual stimulus, as can a single character, object, or other local feature the video depicts. Visibility can also be defined in a relative sense as the ease with which an observer can consciously or unconsciously attend to it. A white disc and a gray disc may both be visible on a black background, but the white target will be more salient to observers due to its higher contrast. Visibility also depends on the target's position in the observer's visual field and numerous aspects of the observer's dynamic visual system: the visibility of most static targets, for example, will decrease over time if the observer does not shift their gaze, due to neural adaptation.

Visibility is also closely linked to "trackability," which is the observer's ability to direct their fovea to the target and maintain its foveal position when the target changes any aspect of its appearance, such as its position. Stimuli that are highly trackable to a given observer can be smoothly pursued, keeping them on the fovea continuously; stimuli that are moderately trackable may require frequent catch-up saccades, and will repeatedly fall off the fovea; and stimuli that are not trackable may rarely or never be placed on the fovea. Visibility is necessary for trackability, and higher visibility will generally lead to higher trackability, but visibility is not sufficient: the observer may not have the attentional or cognitive resources to track (e.g., due to neurological impairment or temporary exhaustion/distraction). Thus, trackability, like visibility, is not a property intrinsic to a given stimulus, but rather a property that describes an interaction between visual stimuli and the dynamic behavioral/neurological status of a given observer.

Knowledge of stimulus visibility and trackability is critical in diagnosing visual impairments, designing interactive visual experiences such as video games, virtual reality programs, and user interfaces, and in behavioral research. The accurate and efficient assessment of these two aspects of visuomotor activity is therefore of high value in numerous fields.

A system and method for solving these problems is desired. Herein, systems and methods that use eye movements, as detected with an eye tracker, to infer the visibility and trackability of visual stimuli to an observer are provided. Multiple types of tracking can be detected to reach a larger population of human observers with varying levels of innate tracking ability and varying neurological and clinical profiles.

SUMMARY OF THE INVENTION

The invention generally relates to systems and methods for dynamically assessing a visual function of a subject are provided where the system and method account for fixation eye movement(s); saccade eye movement(s); smooth pursuit eye movement(s); optokinetic nystagmus eye movement(s); and/or blink eye movement.

In embodiments, a system for dynamically assessing a visual function of a subject is provided, comprising: i) a visual display; ii) an eye-tracking device configured to detect a gaze position of at least one eye of the subject; iii) one or more processors operably connected to the visual display and the eye-tracking device; iv) a non-transitory memory operably connected to the one or more processors and including machine executable code that when executed by the one or more processors performs the steps of: a) presenting for a first defined amount of time a first stimulus at a first location on the visual display; b) storing first stimulus information associated with the first stimulus, the first stimulus information including: i. first stimulus location information associated with a location of the first stimulus on the visual display for the first predetermined amount of time; and ii. first stimulus time stamp information associated with the first stimulus location information; c) receiving in real time, from the eye-tracking device, for the predetermined amount of time, first tracking data comprising: i. first gaze point information associated with a first point on the visual display to which the eye is directed during the predetermined amount of time; ii. first position information associated with a 3D position of the eye over the predetermined amount of time; and iii. first gaze point time stamp information associated with the gaze point information and the position information; d) storing the first tracking data in the non-transitory memory associated with the first stimulus; e) determining, for the first stimulus, a dynamic evidence-of-visibility score and a dynamic evidence-of-trackability score based at least on the tracking data and the first stimulus information; f) storing in the non-transitory memory, associated with the first stimulus: i. the dynamic evidence-of-visibility score; and ii. the dynamic evidence-of-trackability score; analyzing the stored first tracking data to determine a presence of one or more of: i. fixation eye movement(s); ii. saccade eye movement(s); iii. smooth pursuit eye movement(s); and iv. blink(s); h) analyzing the first tracking data obtained via the eye-tracking device to identify for the eye, relative to the first stimulus: i. position-matched tracking eye movements; ii. trajectory-matched tracking eye movements; and iii. saccade-based tracking eye movements; i) updating, in real time, the dynamic evidence-of-visibility score and/or the evidence-of-trackability score associated with the first stimulus based on at least one of any eye movements detected in step g) and step h); and j) updating in real time the appearance of the first stimulus to provide a second stimulus based on at least one of the updated evidence-of-visibility score and the updated evidence-of-trackability score for the first visual stimulus.

In embodiments, a method for dynamically assessing a visual function of a subject is provided, comprising using a system as described herein.

BRIEF DESCRIPTION OF THE DRAWINGS

A further understanding of the invention can be obtained by reference to embodiments set forth in the illustrations of the accompanying drawings. Although the illustrated embodiments are merely exemplary of systems, methods, and apparatuses for carrying out the invention, both the organization and method of operation of the invention, in general, together with further objectives and advantages thereof, may be more easily understood by reference to the drawings and the following description. Like reference numbers generally refer to like features (e.g., functionally similar and/or structurally similar elements).

The drawings are not necessarily depicted to scale; in some instances, various aspects of the subject matter disclosed herein may be shown exaggerated or enlarged in the drawings to facilitate an understanding of different features. Also, the drawings are not intended to limit the scope of this invention, which is set forth with particularity in the claims as appended hereto or as subsequently amended, but merely to clarify and exemplify the invention.

FIG. 2A depicts a participant engaging with the Curveball task. An eye tracker 208 (e.g., the Tobii 4C) is attached to the bottom of an all-in-one computer (e.g., visual display 206), which may be held in front of the participant (e.g., subject 202) at 62 cm with an articulated arm. The noise depicted on the computer screen 206 is 1 cycle per degree (CPD). FIG. 2B is a screenshot in accordance with the Curveball task that demonstrates the size and Hann windowing of a noise target (e.g., stimulus 204-1). The noise target depicted is 1 CPD.

DETAILED DESCRIPTION OF THE INVENTION

Figure 1:
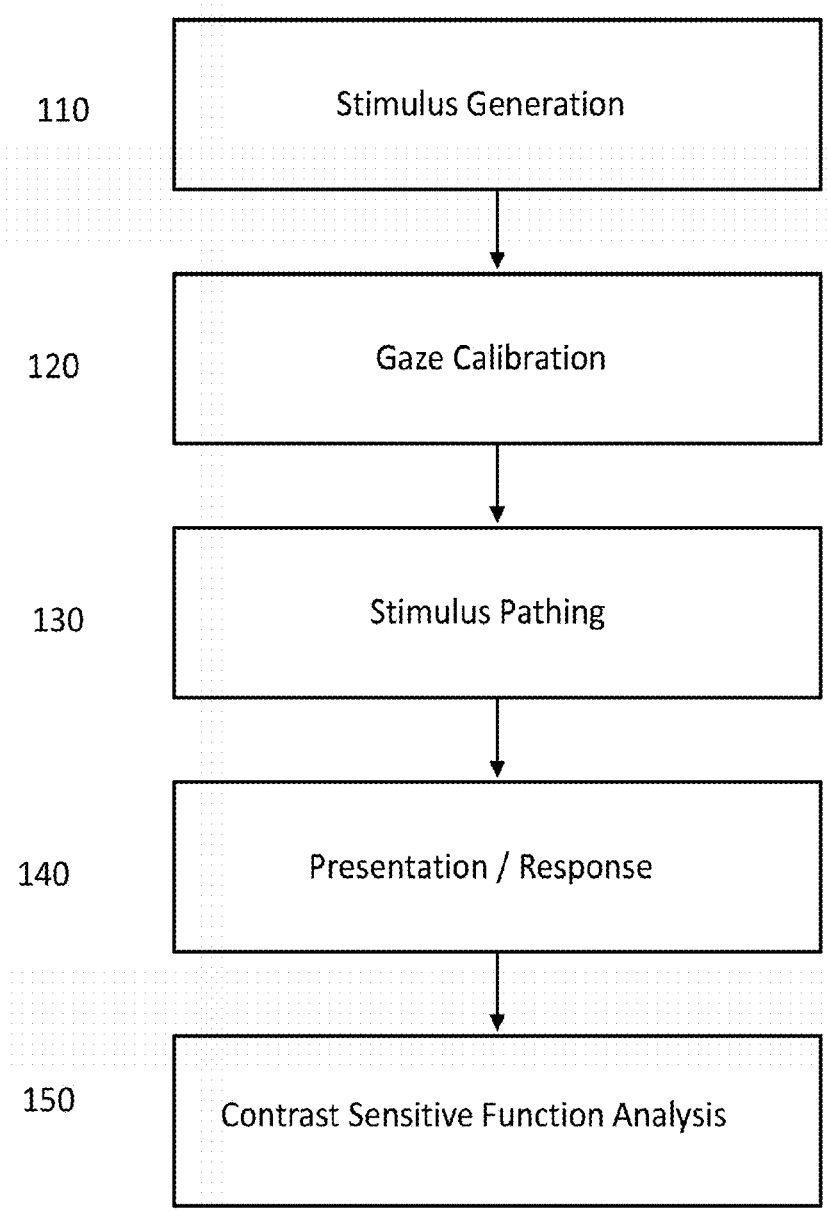
FIG. 1 is a flowchart depicting several steps in an illustrative embodiment of a method in which the method of the invention can be employed.

The invention generally relates to systems and methods for dynamically assessing a visual function of a subject are provided where the system and method account for fixation eye movement(s); saccade eye movement(s); smooth pursuit eye movement(s); optokinetic nystagmus eye movement(s); and/or blink eye movement.

The invention may be understood more readily by reference to the following detailed descriptions of embodiments of the invention. However, techniques, systems, and operating structures in accordance with the invention may be embodied in a wide variety of forms and modes, some of which may be quite different from those in the disclosed embodiments. Also, the features and elements disclosed herein may be combined to form various combinations without exclusivity, unless expressly stated otherwise. Consequently, the specific structural and functional details disclosed herein are merely representative. Yet, in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

A system in accordance with the present invention may include a computer device having a computer processor (CPU) and a non-transitory computer readable storage medium, a display, and an eye-tracking device. The computer device also preferably has a graphics-processing unit (GPU). An example computer device is the 27" widescreen LCD Lenovo Horizon 2 "all-in-one" computer. The memory of the computer device may store software to operate the computer and run the algorithms and other software used during each evaluation. The computer may also be used to process the data generated during each evaluation.

Preferably, the gamma function and the minimum and maximum luminance of the display screen are determined. Screen luminance of the display may, for example, be calibrated with the sRGB profile (gamma of approximately 2.2). Screen luminance may, for example, be measured with an ILT1700 radiometer and may range linearly, for example, from 0.1 (black) to 211.1 (white) cd/m.sup.2 with the room lights off (the "dark" condition) and, for example, 10.0 to 221.1 cd/m.sup.2 with the lights on (all other conditions). The display may be mounted on a wheeled stand with an articulated arm and equipped with a USB display-mounted eye-tracking device, such as the Tobii 4C eye tracker. The eye-tracking device may be capable of detecting the gaze position of one or of both eyes simultaneously. The Tobii 4C has an operating distance of 50 to 95 cm and samples mean gaze position at 90 Hz by combining data from both eyes.

Curveball

The present invention discloses novel systems and methods for rapidly estimating the contrast sensitivity function (CSF) using eye movements. The present invention, referred to herein as "Curveball", minimizes the influences of attention, motivation, and communicative ability on task performance without sacrificing the efficiency of conventional methods. The present invention may comprise five distinct steps as shown in FIG. 1 and described below. Numerous variations and combinations of these steps may be utilized in the preferred embodiment, including but not limited to the complete omission of one or more steps. Additional components of the invention are also described below.

Where the present disclosure refers to "gaze", "gaze data", "gaze samples", "gaze position", and other descriptions of data generated by the eye tracker hardware, the gaze data referred to may be one or both monocular streams of data (i.e. data that describes the 2D gaze position on the display and the 3D absolute position in space of a single eye) or a combined binocular stream computed from both monocular streams. In ideal circumstances, monocular data streams may be used, and each aspect of gaze data processing described below (e.g. saccade detection, blink detection) may be performed separately for each available monocular stream or may combine data from both monocular streams. The user may also elect to measure only one monocular stream by obscuring one of the subject's eyes or by manipulating the eye tracker hardware and/or data processing algorithms. The availability of monocular streams may depend on the available eye tracker hardware in different embodiments of the invention; where only a single binocular stream is available, the gaze data processing described below may be performed for that stream. In this case, binocular variants of the processing algorithms may be used.

At the Stimulus Generation Step (110), one or more "stimulus sweeps" may be created. A stimulus sweep may comprise an ordered sequence of one or more visual stimuli.

Each stimulus may be parameterized by a spatial frequency value and a contrast value. The stimuli may be sine wave gratings, band-filtered isotropic or anisotropic image textures (e.g. randomly generated noise), or a combination of both. If band-filtered textures are used, they may be produced by taking 1/f amplitude spectrum noise with a random phase spectrum and multiplied in the frequency domain with an annular band-pass filter centered on the target spatial frequency that has a width of 10% of the target spatial frequency. The sequences of spatial frequency and contrast configurations that make up each sweep may form a continuous trajectory through the CSF space (e.g. a straight or curved line) or may be arbitrary (e.g. a random sequence of parameter pairs).

The sequences may be predetermined in advance of the Presentation/Response Step (140) (described further below) or defined "on the fly" during the Presentation/Response Step (140) in response to participant input. Similarly, the stimulus textures may be generated in advance of the Presentation/Response Step (140) or created "on the fly" during the Presentation/Response Step (140). The stimuli may be windowed with a continuous function that reduces contrast as a function of radial distance from the center of the stimulus (e.g. a Hann window). The stimulus size may vary depending on the spatial frequency of the stimulus texture, the number of sweeps that will be presented simultaneously, the size of the physical display, and the measurement needs of the particular test being performed.

The stimuli may be filtered using an anisotropic bandpass filter to ensure that temporal aliasing does not occur during stimulus motion. For example, the filter may remove all components with horizontal spatial frequency greater than 2.85 cycles per degree (CPD), which is 95% of the Nyquist limit (3 CPD) of a stimulus moving at 10 degrees per second on a display with a refresh rate of 60 Hz. Different anisotropic filters may be applied at different stimulus speeds as the Nyquist limit changes. The orientation of the noise patch may be continuously steered into its direction of motion to keep the anti-aliased direction of this filter "facing forward" at all times.

Evidence of seeing on a particular place on the viewing screen can be used as a source of system calibration, particularly for subjects who are non-verbal. For example, for a subject who is determined to track the path of a moving object well on a restricted part of the screen, that is good evidence that the subject was looking at that part of the screen and not somewhere else. This information can be used to update the calibration of the tracker. In an example, if this is done rapidly in a session in which a subject tracked in various parts of the screen, it can act as methodology to calibrate, without a formal calibration step. This could be done with one or both eyes. Alternatively, formal calibration, e.g., against known or predetermined parameters, can be employed.

At the Gaze Pre-Calibration Step (120), a set of predetermined stimuli are presented on a uniform background on the display to calibrate the eye tracker. These stimuli may be small shapes (e.g. a disc with holes cut out of it) and their quantity and arrangement may depend on the mode of calibration desired for that particular participant and data collection session. The background may be, for example, black, or any other uniform color or shade.

In one-point calibration mode, a single stimulus is presented. The stimulus may be presented in the center of the display, or in another location on the display. For each updated display frame in which the participant's gaze falls within a certain radius of the stimulus (for example, 5 degrees of visual arc), the participant is presumed to be fixating upon the stimulus, and the difference vector between the gaze position and true stimulus position may be used to update a calibration translation vector. The final calibration vector may be used throughout the remainder of the steps to correct all gaze position data reported by the eye tracker for that participant.

In four-point calibration mode, four stimuli are presented instead, for example, one in each corner of the screen. A calibration translation vector may be updated independently for each corner's stimulus using the same method as the one-point calibration mode. The resulting four calibration vectors may be used to create an interpolated perspective mapping that may be used to correct all future gaze position data. The Gaze Pre-Calibration Step (120) may be omitted if calibration is unfeasible for the participant or if the existing calibration of the eye tracker is sufficient.

At the Stimulus Pathing Step (130), a determination may be made as to how the sine wave grating or band-filtered texture stimuli will move during the Presentation/Response Step (140). The stimuli may follow one or more predetermined paths that have been programmed and stored in memory in advance, or their paths may be procedurally generated by an algorithm. For example, the stimuli may move within an invisible grid, may avoid collisions with other stimuli by not moving to grid cells that are currently occupied, and may avoid repeating the same type of movement twice in a row and/or making the same type of concurrent movement as other active stimuli. The procedural generation may determine stimulus paths in advance of the Presentation/Response Step (140) and/or generate upcoming path segments "on the fly" during that step. The initial positions of the stimuli may be predetermined or random, with or without additional restrictions (e.g. preventing multiple stimuli from appearing at the same location).

Stimulus speed may change throughout the path and/or vary both between and within method applications as a function of participant responses or to facilitate different measurement needs or display devices. For example, stimuli may move at 10 degrees per second on a larger display when following a straight path, but decrease in speed to 8 degrees per second when following a curved path.

The Presentation/Response Step (140) comprises the core loop of the invention. One or more stimulus sweeps are selected to be presented to the participant. One or more stimulus sweeps may be presented simultaneously. At the beginning of the procedure, the first stimulus in each of these selected sweeps may be presented, or a number of stimuli at the beginning of the sweep sequence may be skipped (for example, if progress on that sweep has already been made in a previous session with that participant). While visible, the stimuli may move along one or more paths generated in advance of the Presentation/Response Step (140) and/or may move along a path determined "on the fly" during the Presentation/Response Step (140).

Each sweep has an "evidence-of-visibility" score, which indicates the current strength of evidence that the participant can see the currently active stimulus in that sweep. While a sweep is active during the Presentation/Response Step (140) (i.e. its current stimulus is displayed), this evidence-of-visibility score is monitored and updated. The evidence-of-visibility scores are used to determine when the current stimulus should be modified or exchanged for the next stimulus in that sweep, to calibrate the participant's gaze data, and to calculate the participant's visual function.

The Presentation/Response Step (140) also uses a "global evidence" score, which is continuously monitored and updated. This score indicates whether the current stimuli of any active sweeps are visible to the participant, and informs the stopping criterion for the Presentation/Response Step (140). If only one sweep is active, the global evidence score may simply be the evidence-of-visibility score of that sweep. If more than one sweep is active, the global evidence score may be computed from the combination of evidence-of-visibility scores of one or more active sweeps, or it may be computed independently of any sweeps (e.g. by determining if the participant is looking away from the display).

An algorithm continuously (e.g. at the same rate as the display refresh rate) monitors the participant's gaze response to all active stimuli and, in response to specific patterns of gaze input and stimulus attributes, may (a) update the evidence-of-visibility score of any active sweep, (b) update the global evidence score, and/or (c) start or stop presenting a novel audiovisual stimulus to provide feedback to the participant.

The patterns of gaze input that trigger these continuous responses may include fixations, saccades, smooth pursuits, target tracking, optokinetic nystagmus, and/or blinks. The algorithm that classifies these gaze responses may also detect "impossible" eye movements that suggest that the eye tracker is unable to obtain a reliable estimate of the participant's gaze, and alert the Curveball user accordingly. When the algorithm detects that the participant is not in front of the display, or detects that the participant's distance is too close to or too far away from the display, the task may be paused automatically until the participant is in front of the display within a permitted distance range (e.g. 400 to 800 millimeters).

The algorithms used to detect and classify different types of gaze responses may vary; some example algorithms are described below. Different algorithms, for example, may be required for different eye tracking hardware used in different embodiments of the invention. The statistics employed by these algorithms may be computed continuously while practicing the present invention and used for analytic and feedback purposes other than the exemplary classifications described herein.

Fixation events may be detected by analyzing the two-dimensional dispersion metric of the x/y gaze coordinates over a sliding time window of gaze samples (e.g. 0.15 seconds) each time a new gaze sample arrives. Gaze samples may be classified as part of an ongoing fixation event when the mean dispersion over this time window falls below a certain threshold. The mean position of the fixation event may be compared to the position of one or more active stimuli to determine which of those stimuli may be fixated ("target fixation").

Saccade events may be detected by analyzing gaze velocity over a sliding time window of gaze samples (e.g. 0.15 seconds) each time a new gaze sample arrives. Saccades may start when the magnitude of this velocity rises above a certain "start" threshold (e.g. 50 degrees per second) and persist through future gaze samples as long as the magnitude remains above a certain "end" threshold, which may differ from the start threshold (e.g. 30 degrees per second). False positives of this algorithm may be detected by additionally restricting the change in velocity direction from sample to sample below a certain angle (e.g. 90 degrees) after a saccade has started and/or ignoring detected saccades with a duration below a certain threshold (e.g. 50 milliseconds).

Smooth pursuit events may be detected by analyzing gaze velocity and acceleration over a sliding time window of gaze samples (e.g. 0.15 seconds) each time a new gaze sample arrives. Smooth pursuits may start when the magnitude of gaze velocity falls between certain minimum and maximum "start" thresholds (e.g. 5 degrees per second to 20 degrees per second) and the rate of change in the direction of gaze velocity is less than a certain angular value (e.g. 180 degrees per second), and persists as long as gaze velocity continues to fall within these thresholds.

Target tracking events may be detected by analyzing gaze position over a sliding time window of gaze samples (e.g. 0.15 seconds) each time a new gaze sample arrives, and comparing it to the position of a given target over the same time window. The algorithm may report that the participant is tracking that target if a sufficient proportion of gaze samples within that time window (e.g. at least 90%) fall within a certain distance of the position of the target at the same moment (e.g. 0.4 degrees of visual arc). The coordinates of the target to which gaze position is compared may be its absolute position on the display, or may first be corrected by subtracting the current gaze position from each target position sample so that any systematic offset between the target trajectory and gaze trajectory is ignored (e.g. the participant may not be tracking the exact center of the target). Target tracking may need to persist for some number of contiguous samples (e.g. five samples) before it is confirmed as a true positive classification.

In embodiments, target tracking events may be detected by monitoring "targeted" saccade eye movements. A targeted saccade, in embodiments, may be classified as a saccade that starts and ends within a predetermined distance and/or range of distance(s) from the target (e.g., five degrees of visual arc). For example, a targeted saccade may be classified as a saccade which starts within a first predetermined distance of the target (e.g. four degrees of visual arc) and ends within a second predetermined distance (which may be a smaller distance than the first predetermined distance (e.g. three degrees of visual arc)). In embodiments, target tracking may be determined when, for example, targeted saccades occur at and/or above a predetermined frequency (e.g., once per second). In embodiments, target tracking may be determined, as another example, when targeted saccades occur with sufficient frequency (e.g. twice per second) for a sufficiently long duration (e.g. two seconds). In embodiments, target tracking may be determined, as another example, when targeted saccades occur with sufficient frequency (e.g. three occurrences per second) for a sufficiently long duration (e.g. 1 second) without any non-targeted saccades. In embodiments, target tracking may be determined based on one or more of the following: the amount of occurrences of targeted saccades; the frequency of occurrences of one or more targeted saccades; the duration of occurrences of one or more targeted saccades; the occurrence of non-targeted saccades. Saccade-based target tracking, in embodiments, may be repeated one or more times. In embodiments, confirmation of a true positive classification may require more than one saccade-based target tracking sample. For example, saccade-based target tracking may need to persist for a predetermined number of contiguous samples (e.g. five samples) before a determination of a confirmed true positive classification can be made.

Optokinetic nystagmus events may be detected in a similar way to target tracking, but the trajectory of the participant's gaze may be required to be linear and interspersed with saccades whose velocity is in the opposite direction to the trajectory.

A blink is a movement of a skin membrane over the eye. Eye blinks can occur during tracking are a source of noise. In embodiments, blink(s) are identified and their impact on the algorithms that build evidence of seeing is removed or mitigated. Blink(s) can also be a source of information related to quality of tracking, however, because they may change in some circumstances, for example when tracking is more difficult or when attention lapses. Thus, blink(s) are identified and collected for signal-cleaning purposes, but the information can also be employed (e.g., blink number or blink pattern) as a source of information for determining evidence of tracking as evidence of seeing.

Blinks may be detected using an algorithm that varies with the exact eye tracker hardware used during the application of the method, as different eye trackers may produce different "signature" responses to blinks. For example, blinks may be classified by detecting periods in which no gaze data is reported by the eye tracker for no longer than a predetermined time (e.g. two seconds). Gaze samples immediately before and/or immediately after the detected blink (e.g. up to 0.5 seconds on each side) may be ignored to avoid the risk of using malformed gaze data during the blink.

The evidence-of-visibility score may be assigned a starting value prior to the Presentation/Response Step (140). The starting value may be zero, 100, or another value. During the Presentation/Response Step (140), different gaze responses may then affect the evidence-of-visibility score of one or more sweeps and/or the global evidence score in different ways. For example, responses that indicate that an active sweep stimulus is visible to the participant, such as fixations that match the position of a stimulus, saccades that start from another point on the display and end at the position of a stimulus, and persistent tracking of a stimulus as it moves, may add certain predetermined values to the evidence-of-visibility score for that stimulus's sweep. The value added may represent the weight of that response's evidence (e.g. 1 point per frame of target fixation, 5 points per saccade-to-target, and 10 points per frame of target tracking). Responses that indicate that an active sweep stimulus is not visible to the participant, such as "searching" saccade behavior (which may be classified as a series of repeated saccades to non-target positions in opposing directions) or looking away from the screen, may subtract certain predetermined values from the evidence-of-visibility score for all sweeps and/or the global evidence score (e.g. 5 points per searching saccade, 1 point per frame of looking off-screen). Evidence-of-visibility and/or global evidence scores may decrease by a certain value automatically per frame (e.g. 1 point).

The value of evidence from target tracking may be weighted by a continuous auto-correlation analysis of the target trajectory, e.g. so that tracking targets that follow less predictable trajectories (e.g. more curved, more frequency and more abrupt turns) adds less evidence-of-visibility to that target stimulus's sweep. The tracking evidence value, for example, may be multiplied by 1 minus the auto-correlation coefficient of the stimulus over a sliding time window of a certain duration (e.g. 1 second).

The system may determine whether a sweep's evidence-of-visibility score exceeds or falls below a certain threshold, or falls within or outside a certain range. The exact evidence threshold or range may vary both between and within method applications as a function of the parameters of the active stimulus in that sweep or to facilitate different measurement needs.

Whenever a sweep's evidence-of-visibility score exceeds a certain threshold or falls within a certain range, it may be inferred that the participant can see the active stimulus in that sweep, and the stimulus may have its appearance altered (for example, an increase or decrease in contrast, size, or speed), or may be swapped out entirely for the next stimulus in that sweep's sequence, at which point that sweep's evidence-of-visibility score is reset to the starting value. Whenever a sweep's evidence-of-visibility score falls below a certain threshold or falls outside a certain range, it may be inferred that the participant cannot see the active stimulus in that sweep, and the system may terminate display of the visual stimulus, and present on the display a visual stimulus of another sequence of visual stimuli. The sweep's evidence-of-visibility score would begin at the starting value. Prior to the Presentation/Response Step (140), an algorithm may be used to determine paths each visual stimulus will follow.

When the global evidence score falls below a certain threshold, it may be inferred that none of the currently active stimuli in the currently presented sweeps are visible to the participant, and the trial may be terminated. All evidence-of-visibility scores and stimulus changes that occurred within each sweep may be recorded to inform the CSF Analysis Step (150) and/or to skip some number of stimuli in future presentations of the same sweep. A new trial may then begin with new sweeps and/or repeated presentations of previous sweeps, possibly following an intermission phase where other stimuli are presented to provide a break and/or reward for the participant. If the method infers that sufficient data has been collected (e.g. a predetermined number of trials has been completed for each sweep), the Presentation/Response Step (140) may end.

A sweep's evidence-of-visibility score may also be used to continuously calibrate the eye tracker in real time as the current stimulus of that sweep and/or the participant's gaze move to different areas of the display. The eye tracker hardware used in a given embodiment of the invention may not be able to accurately calibrate a participant's gaze to the screen used in that embodiment, in which case the one-off calibration performed in the Gaze Pre-Calibration Step (120) may not be suitable for the entirety of the display. When a stimulus's evidence-of-visibility score is sufficiently high during the Presentation/Response Step (140) and the participant is determined to be fixating on a stimulus, the calibration parameters may be adjusted to improve the accuracy of gaze position data in the region of the display currently occupied by the stimulus. This improvement may change the parameters of a one-point calibration or a four-point calibration. In this way, evidence-of-visibility scores may be used as feedback to improve future computations of evidence-of-visibility scores.

Other types of data provided by the eye tracker hardware may also be used in the gaze processing algorithms of the invention's software. Eye distance, for example, may be used to monitor and act upon the participant's distance from the display and determine the true spatial frequency (in degrees of visual arc, relative to the participant's true distance from the display) of any stimuli being presented. Head pose data, where provided, may be used to continuously determine which of the participant's eyes are currently visible to the eye tracker and whether the participant is facing the display.

Additional images, animations, and/or videos may be presented in tandem with the stimuli or between trials to facilitate task attention or provide a reward or break to the participant. The images may be, for example, semi-transparent textures superimposed on the moving noise target to quickly draw a participant's attention to the noise target. For example, a cartoon ghost may appear on top of the stimulus at the start of each trial to draw the observer's gaze, and then disappears upon initial fixation. The assistive image may fade out as soon as the participant's gaze comes within, for example, 5 degrees of the image.

As a further example, one or more images or animations (e.g. animated fireworks) may, for example, appear as a visual reward for a predetermined amount of time (e.g. two seconds) at the end of a trial or when a certain duration or quality of gaze response is detected. As a further example, a video may be played on the computer screen between trials to provide the participant with temporary relief from the task. These images, animations, and videos may or may not include audio content.

At the Contrast Sensitivity Function (CSF) Analysis Step (150), the progress made on all sweeps in all completed trials is used to compute an estimate of part or all of the participant's CSF. The final configurations of spatial frequency and contrast that were presented for each sweep (the "sweep thresholds") may be interpreted as estimates of the boundary of the CSF, which separates visible combinations of spatial frequency and contrast from invisible combinations. A polynomial or other non-linear function may be fitted to these sweep thresholds to compute an interpolated estimate of the entire curve, or individual sweep thresholds may be used as individual measures of the CSF. For example, a sweep comprising stimuli of increasing spatial frequency and constant contrast may be interpreted as an estimate of the participant's high-contrast or low-contrast acuity. Alternatively, as another example, a sweep comprising stimuli of constant spatial frequency of 1 cycle per degree of visual arc and decreasing contrast may be interpreted as an estimate of the participant's peak contrast sensitivity.

Another component of the present invention includes an algorithm to analyze a data set of CSFs to determine the subset of one or more measured sweeps (the "basis sweeps") whose thresholds are, statistically, the most highly predictive of the CSF computed from the full set of sweeps in the same population. The predictive value of a subset of sweeps may be computed using a multivariate multiple regression with the full set of sweeps as the dependent variables. This algorithm may be used to reduce the number of sweeps required to robustly estimate the CSF in future Curveball sessions within that population. The single sweep whose threshold is most predictive of the entire CSF of a participant from that population is labeled as the "Concuity" sweep of that population. The empirical identification of the Concuity sweep is a novel feature of the present invention.

Variations of the present invention may be used to assess visual functions other than the contrast sensitivity function. The visual stimuli comprising the sweep sequences may be parameterized along dimensions other than spatial frequency and contrast, and may be generated in visual forms other than sine wave gratings or band-filtered noise textures. The Gaze Pre-Calibration Step (120), Stimulus Pathing Step (130), and Presentation/Response Step (140) may be otherwise identical for these varied applications. The evidence-of-visibility scores may be used to calculate visual functions relevant to the dimensions of any stimulus parameterization, by finding the threshold between stimulus visibility and stimulus invisibility along the dimensions that vary across the sweep sequence. Examples of such dimensions include, without limitation: stimulus orientation; stimulus color contrast; the speed and/or direction of stimulus motion; stimulus size; stimulus temporal frequency; and stimulus position relative to fixation. Any such stimulus dimensions can be combined in a given application of the present invention, and the methods of the invention can be used to estimate and describe the N-dimensional psychophysical threshold manifold separating combinations of stimulus parameters that are visible to the participant from combinations of parameters that produce invisible stimuli. Data sets of such thresholds measured in populations may then be used to statistically determine the subset of sweeps that are most predictive of those thresholds, in the same way as described above for contrast sensitivity.

Another aspect of the present invention is the physical hardware on which the above procedure is installed and run as software. Various configurations of displays, computers, and eye tracker components may be used to practice the present invention. For example, the invention may be practiced with an all-in-one computer, which may be attached to a mobile apparatus that allows the display to be positioned in front of an immobile participant at an appropriate distance, or stabilized in some other fashion (e.g. simply positioned on a flat surface). Alternatively, the present invention may be practiced using a device such as a tablet, a laptop, a mobile phone, a virtual-reality or augmented-reality display device, or a monitor attached to a desktop computer. The eye tracker used to measure the participant's gaze response may be a head-mounted eye tracker, such as the Tobii Pro Glasses, a display-mounted eye tracker, such as the Tobii 4C, or an eye tracker integrated into the display device itself, such as the Oculus Rift or Oculus Quest virtual-reality headset.

The Curveball algorithm may be programmed in any one of a variety of coding environments. For example, the stimulus behavior may be programmed in Python using the Shady graphics toolbox and may be updated and rendered at a frame rate of 60 Hz. Gaze data may be analyzed in real time using the Curveball algorithm, which measures the similarity between gaze and stimulus trajectories to infer stimulus visibility on a frame-by-frame basis.

Each evaluation may begin with a calibration phase, which may include the sudden presentation of an image in the center of the display. Alternatively, multiple images may be presented on the display. For example, one image in each corner of the screen. Each image may be, for example, a white disc with a plurality of dark circles. The image may be presented against a uniform gray background (e.g., value of 0.5), and that same background may be used for the subsequent trial phase. The image may be designed to draw the participant's gaze to a central calibration point without explicit instructions. The image may also be rotated, for example, with increasing angular velocity as the participant looks at the image (e.g., within 8.degree. of visual angle (hereafter simply .degree.) of its position). This calibration phase may calibrate for any small offset in gaze position, and may be used to ensure that the participant is looking at the display before launching the main task. After a predetermined period of time, such as 0.5 seconds of calibration, the disc may fade out and the trial phase may begin.

At the start of each trial, one or more stimulus images (also referred to herein as noise targets), such as a narrow-band frozen noise patch subtending 12.degree., may appear at a random location on the screen. The stimulus image may then move around the display. The stimulus image may continuously veer clockwise or counter-clockwise in a sequence of smooth random turns. Alternatively the stimulus image paths may be procedurally generated by an algorithm. For example, the stimuli may move within an invisible grid, may avoid collisions with other stimuli by not moving to grid cells that are currently occupied, and may avoid repeating the same type of movement twice in a row and/or making the same type of concurrent movement as other active stimuli. The initial positions of the stimuli may be predetermined or random, with or without additional restrictions (e.g. preventing multiple stimuli from appearing at the same location).

The stimulus image may maintain a fixed speed of, for example, 10.degree. per second, or the speed at which the stimulus image moves on the screen may vary. For example, the speed of the stimulus image may increase at a constant rate, or the speed of the stimulus image may decrease at a constant rate. The speed of the stimulus may change throughout the path and/or vary both between and within method applications as a function of participant responses or to facilitate different measurement needs or display devices. For example, stimuli may move at 10 degrees per second on a larger display when following a straight path, but decrease in speed to 8 degrees per second when following a curved path.

The stimulus image may be generated by applying a circular-symmetric Hann window to a filtered noise pattern that may be re-generated with a new random seed for each trial. The noise may start off with a 1/f amplitude spectrum in the frequency domain and a random phase spectrum. It may then be filtered with an annular band-pass filter centered on the target spatial frequency. The minimum and maximum bounds of the filter may be computed by multiplying and dividing the target spatial frequency by 0.9, respectively, which may gave the filter a width of approximately 0.34 octaves. The resulting noise would then have equal power at all orientations but may be limited to a narrow band of spatial frequencies.

Temporal aliasing at high spatial frequencies may be prevented by applying an additional anisotropic filter to the amplitude spectrum of the noise. This filter may remove all components with horizontal spatial frequency greater than 2.85 CPD, which is 95% of the Nyquist limit (3 CPD) of a stimulus moving at 10.degree. per second on a display with a refresh rate of 60 Hz. Different anisotropic filters may be applied at different stimulus speeds as the Nyquist limit changes. The orientation of the noise patch may be continuously steered into its direction of motion to keep the anti-aliased direction of this filter "facing forward" at all times.

Figure 2A:
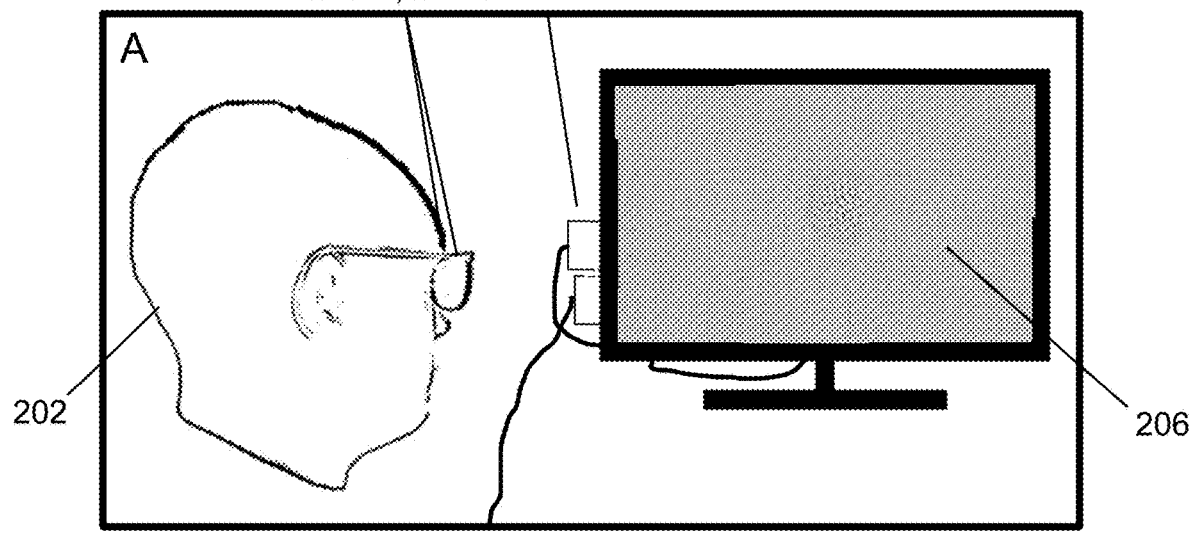
FIGS. 2A and 2B depict an example of the Curveball procedure, in which the method of the invention can be employed.
Figure 2B:
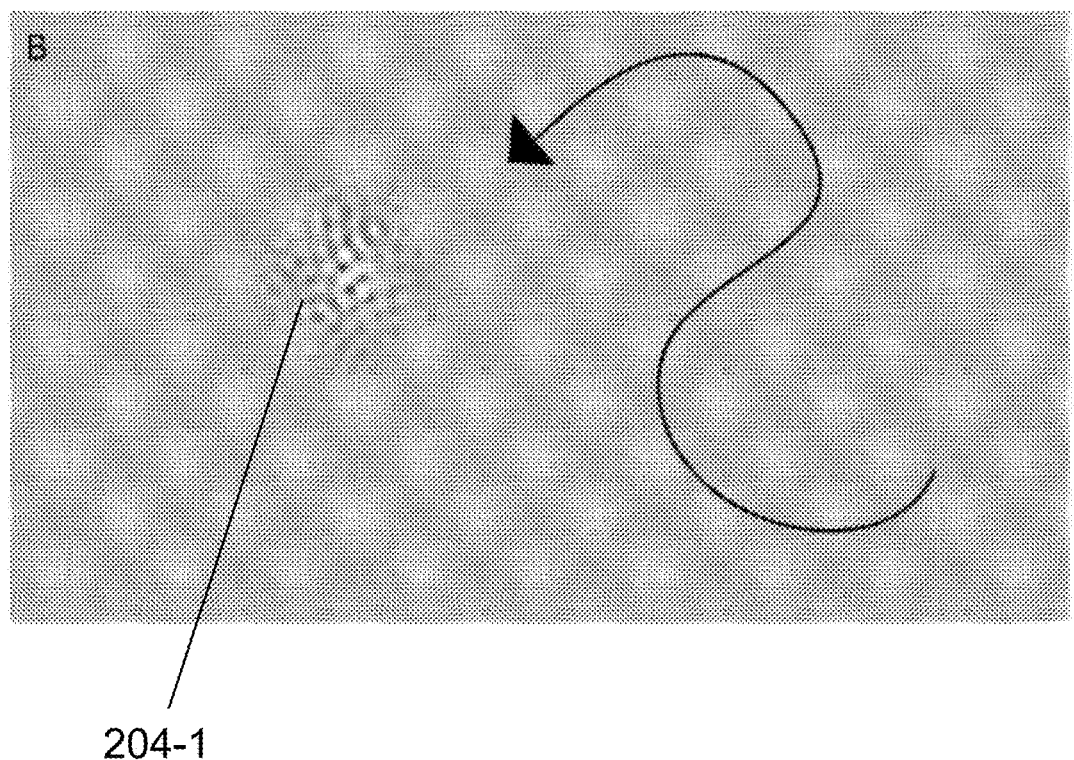

The noise target may sharply rebound whenever it collides with the edge of the screen and may be simultaneously rotated by 180.degree. to continue "facing forward." Rapid variation in stimulus position and rotation may also help ensure that it is presented at all orientations in all regions of the screen within a single trial. The stimulus image size (e.g. 12.degree.) may be chosen to make it large enough to display the lowest spatial frequency in the procedure (e.g., 0.25 CPD) whilst being small enough that its rotation does not interfere with the pursuit detection algorithm if a participant happens to fixate away from its center (where target rotations produce transient higher gaze velocities). Its size may be fixed across all spatial frequencies to avoid changing the difficulty of tracking. A screenshot with the target at high contrast is depicted in FIG. 2B.

At the start of each trial, one or more noise targets may be displayed. The noise target may be generated at the start of each trial. In the alternative, one or more noise targets may be generated and stored in memory in advance of the evaluation, and the software may retrieve the one or more noise targets from memory at the start of each trial.

Figure 2C:
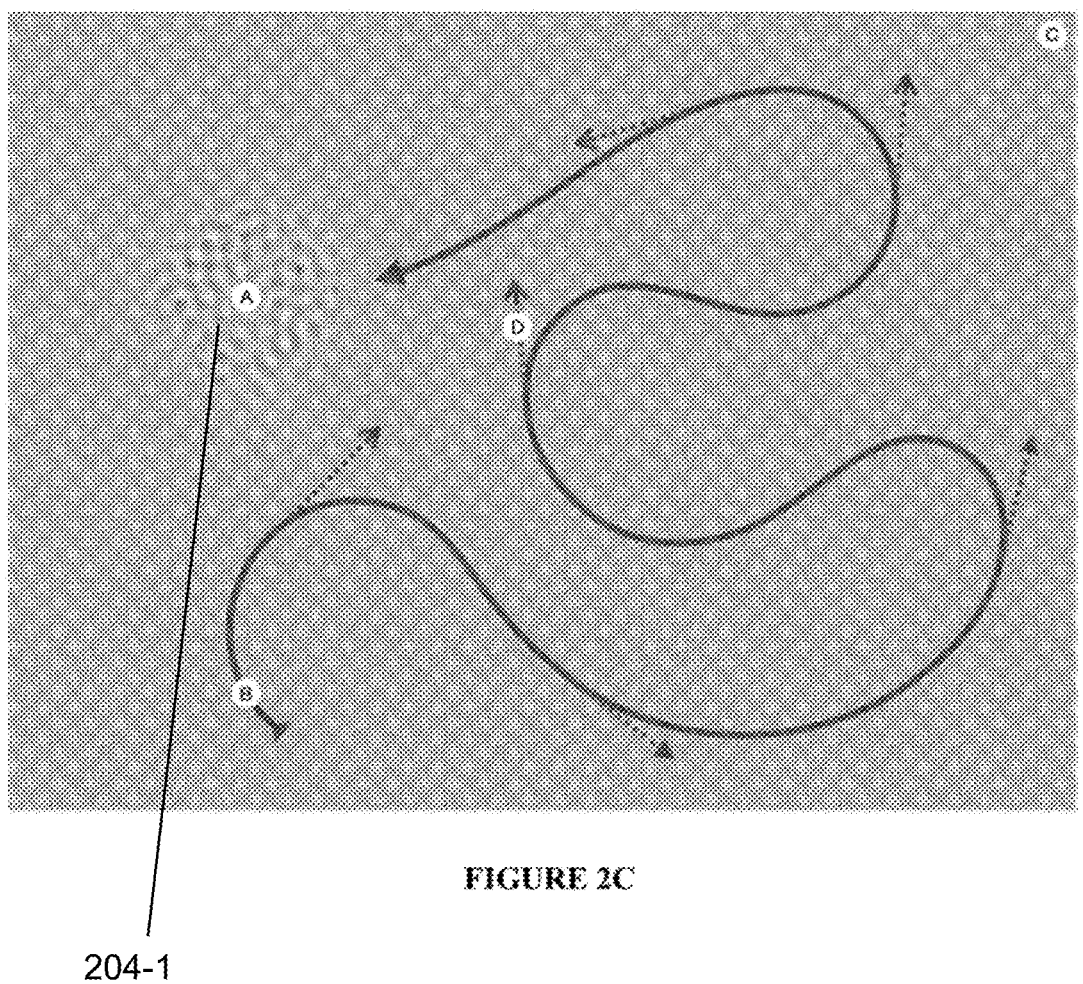
FIG. 2C depicts an exemplary Curveball stimulus presentation in which the method of the invention can be employed. In embodiments, the presentation may include at least one stimulus 204-1.

Referring to FIG. 2C, a circular noise stimulus (A) may move smoothly on a haphazard path (B) across a computer screen (C). Isolated circular patches of similarly band-filtered noise may be displayed as the stimulus. These 'curveball' stimuli (each with a single fixed spatial frequency) may be presented one at a time. The stimuli may drift randomly across the display in all directions. The stimuli may drift at constant speed or variable speed. The stimuli may rebound whenever they hit the edge. Eye movements that match the speed and direction of each stimulus with high adherence may provide evidence of stimulus visibility. Since such smooth eye movements are difficult to produce without the stimulus being present on the retina, eye movements that do not follow the stimulus in the course of testing (D) may provide evidence that the stimulus is not visible. Computer software comprising a computer algorithm may compare the recent trajectories of the stimulus and the observer's gaze to detect tracking, rather than relying solely on a velocity match. The software may require the observer to match the speed, direction, and approximate position of the stimulus at all times to satisfy the algorithm, which is next to impossible when the stimulus is not visible. Successful tracking may cause the contrast of the stimulus to continuously decrease in real time as long as the stimulus is tracked. The trial may terminate when the stimulus is no longer tracked. A threshold estimate may be provided from the trial.

Stimuli with higher spatial frequency may be filtered in one direction (while maintaining the specified contrast value) to avoid temporal aliasing caused by the texture's motion. Each stimulus may rotate as it changes direction to ensure that the direction of the anisotropic filter is always oriented to match the direction of motion.

Thresholds may be estimated one or more times at multiple different spatial frequencies. A curve may then be fitted to the final set of thresholds to estimate the observer's CSF. For example, four repeats may be performed for each of six spatial frequencies.

Figure 2D:
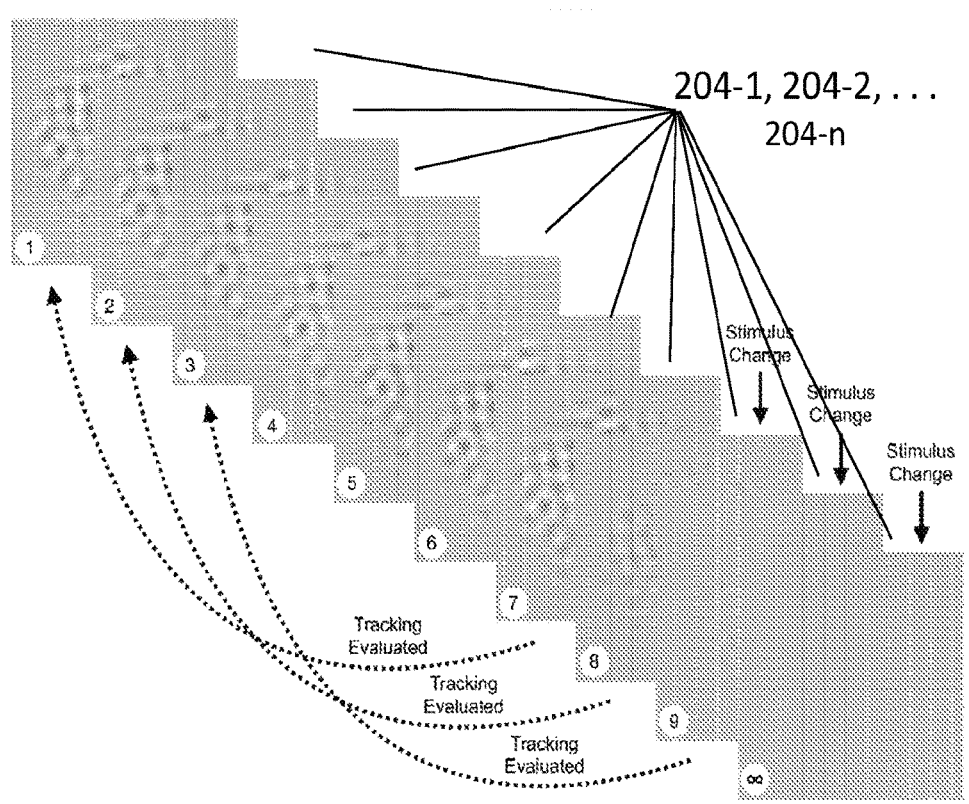
FIG. 2D depicts methodology for manipulating stimulus contrast based on stimulus tracking. In embodiments, the methodology may include a plurality of stimuli 204-$n$.

Referring to FIG. 2D, an algorithm running may infer or estimate stimulus visibility through smooth eye-tracking in a frame-by-frame manner with a gaze-stimulus trajectory match computed over a sliding time window. Based on the trajectory match computed over the past few frames (exemplary number of frames shown in the lower left corner of each frame), stimulus contrast may be lowered in real time using, for example, GPU shaders until a threshold is identified. For example, after evidence of compliant tracking over 7 sequential frames (line with arrow linking frame 7 and frame 1), contrast may be decreased on the 8th frame. If compliant tracking is again present since frame 2, stimulus contrast may be adjusted down on frame 9. That pattern may be followed until compliant eye movements are no longer present and the trajectory match continually fails over a short time interval. The final stimulus contrast provides a provisional estimate of minimal contrast visibility.

Figure 2E:
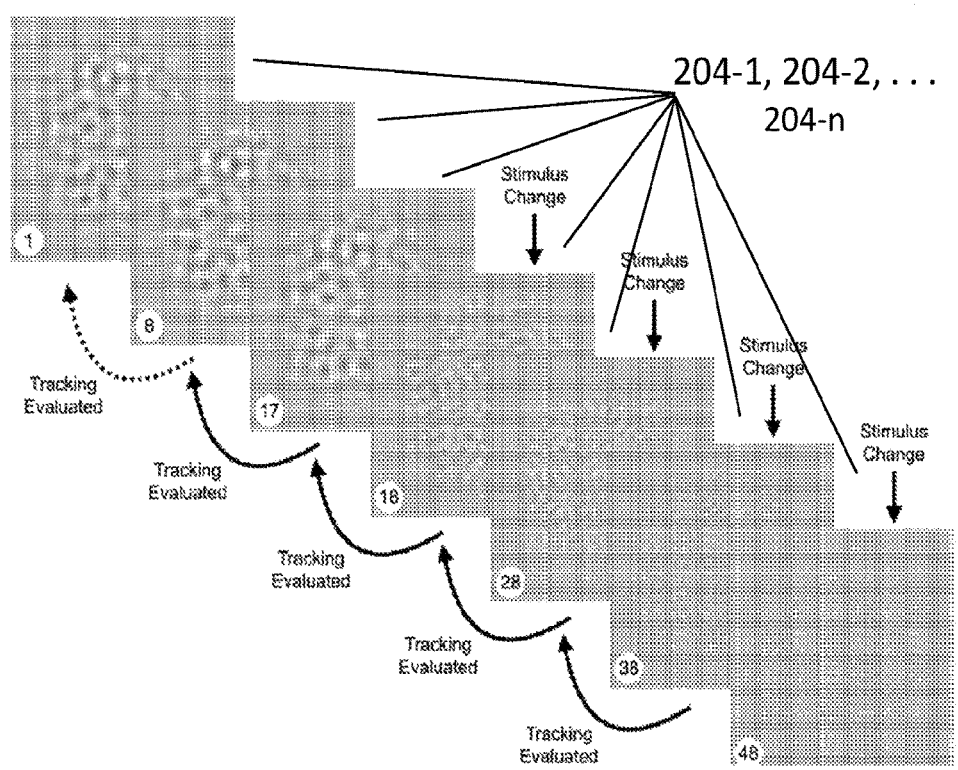
FIG. 2E depicts methodology for simultaneously manipulating stimulus contrast and spatial frequency based on stimulus tracking. In embodiments, the methodology may include a plurality of stimuli 204-$n$.

Referring to FIG. 2E, a software algorithm may infer or estimate stimulus visibility through smooth eye-tracking in a frame-by-frame manner with a gaze-stimulus trajectory match computed over a sliding time window. Compliant tracking may be detected based on a trajectory match computed over some number of most recent sequential frames (e.g. 8) that display the same originating stimulus (frames 1-8, dotted line with arrow). If this sliding-window algorithm detects compliant tracking for a sufficient number of frames in a row (e.g. 10; solid lines with arrows), stimulus visibility may be inferred, and stimulus contrast and spatial frequency are made less visible on the following frame (i.e. 18). This process of inferring stimulus visibility (and changing the stimulus properties) after a predetermined number of frames (e.g. 10 frames) of compliant tracking may continue until tracking is no longer detected by the sliding-window algorithm for a predetermined longer duration (e.g. 180 frames). If tracking is continuous as the stimulus changes, the initial build-up of tracking evidence (frames 1-8) may not re-occur. The final stimulus contrast/spatial frequency combination may provide a provisional estimate of stimulus visibility.

Additional images, animations, and/or videos may be presented in tandem with the noise target(s) or between trials to facilitate task attention or provide a reward or break to the participant. The images may be, for example, semi-transparent textures superimposed on the moving noise target to quickly draw a participant's attention to the noise target. For example, a cartoon ghost may appear on top of the stimulus at the start of each trial to draw the observer's gaze, and then disappears upon initial fixation. The assistive image may fade out as soon as the participant's gaze comes within, for example, 5.degree. of the image. As a further example, one or more images or animations (e.g., animated fireworks) may, for example, appear as a visual reward for a predetermined amount of time (e.g., two seconds) at the end of a trial or when a certain duration or quality of pursuit behavior is detected. As a further example, a video may be played on the computer screen between trials to provide the participant with temporary relief from the task. These images, animations, and videos may or may not include audio content.

After the semi-transparent image fully disappears, the Curveball algorithm may begin searching for smooth pursuits by continuously comparing the recent 2D trajectories of the participant's gaze and the positions of the noise target on the screen. This may be accomplished by examining the trajectory of the target over a number of recent frames (e.g., eight frames) and translating this trajectory to the current gaze position on the screen, which will generate an expected gaze trajectory. Gaze position may first be filtered with a real-time noise removal algorithm that detects and discards estimates of gaze position from the eye tracker that are not consistent with the known limits of human behavior, such as eye movements that are impossibly fast. A tracking 'hit' may be recorded if the most recent gaze position is within some allowed distance (e.g., 1.degree.) of the stimulus center and each point in the recent gaze trajectory is within some allowed distance (e.g., 0.4.degree.) of the corresponding point in the expected trajectory. The algorithm's precise trajectory length and error tolerance may be determined through empirical analysis of the particular eye tracker used (e.g., the Tobii 4C). After a predetermined number of frames (e.g., five frames (83 ms)) of consecutive smooth pursuit "hits" (i.e., the gaze of the participant matches the movement of the noise target), the root mean-square (RMS) contrast of the noise target may decrease, for example, logarithmically. The contrast may decrease as long as smooth pursuit hits continue.

The starting RMS contrast of the noise may be, for example, 0.317; this contrast may be above the maximum contrast (−0.22) that can be displayed on a particular monitor without clipping, but it may be chosen for maximum initial visibility. Every frame of ongoing pursuit may cause its RMS contrast to be multiplied by a predetermined amount, such as 0.97. If a participant stops pursuing the target for a predetermined number of consecutive frames (e.g., one frame, five frames, or 10 frames), the contrast reduction may be halted. The algorithm may then wait for a predetermined number of consecutive frames of pursuit (e.g., one frame, five frames, or 10 frames) before resuming the trial. Contrast may increase and decrease during a trial. In the alternative, contrast may never increase during a trial. Participants may instinctively follow the target's motion on each trial until it fades beyond their threshold, which typically takes up to ten seconds, depending on a participant's sensitivity to a particular spatial frequency and the consistency of their smooth pursuits.

The trial may be terminated according to a continuously updated deadline. For example, every trial may start with a trial duration (i.e., "lifespan") of three seconds starting from the moment the semi-transparent image fully disappears. The lifespan may be increased by six frames (0.1 seconds) every time a frame of smooth pursuit occurs. Participants may therefore need to pursue the target for at least one in every seven frames, on average, to prevent the trial from terminating. When the lifespan expires, the reciprocal of the noise target's final RMS contrast in each trial may be recorded as a sample of the contrast sensitivity threshold at that target's spatial frequency. If the final RMS contrast value is above the value where the stimulus pixel intensities went out of range (e.g., .about.0.22), no threshold may be recorded. Less than 0.25 seconds of tracking may be needed to reduce the target's contrast below this value. The next trial may immediately begin with full contrast, a new noise target, and/or semi-transparent image.

Each participant may, for example, complete four repeats of six spatial frequencies in a full Curveball run. The spatial frequency values may be equally spaced in log units: 0.25, 0.5, 1, 2, 4, and 8 CPD. The lowest two contrast thresholds for each spatial frequency may be averaged to determine the final threshold estimates. This may account for participants 'dropping' trials due to false negatives, which could be caused by inattention, poor or infrequent tracking, or other reasons. In lieu of a systematic way of detecting these false negatives, the worst (highest) threshold estimates (e.g., the worst 50% of threshold estimates) may be discarded to remove them. The twenty-four noise patches required may be generated on the CPU as the task is initialized, but their visibility, contrast, windowing, gamma-correction, 'noisy-bit' dithering and position may be processed in real time, for example, with a GPU using the Shady graphics toolbox. The efficiency of the GPU operations may ensure that the task runs at a consistent frame rate of 60 Hz. In total, a full run of Curveball may take an average time of 5 minutes and 15 seconds (standard deviation of 37 seconds) across all observers and conditions.

The Curveball algorithm requires participants to smoothly pursue the noise target, and this pursuit behavior must be of sufficient quality to be distinguished from other eye movements (such as saccades) that provide much weaker evidence about target visibility. If a participant cannot pursue a given target smoothly enough to meet the algorithm's minimum requirement, the trial will end prematurely and their sensitivity to that target's spatial frequency will be underestimated (a false negative).

Figure 3:
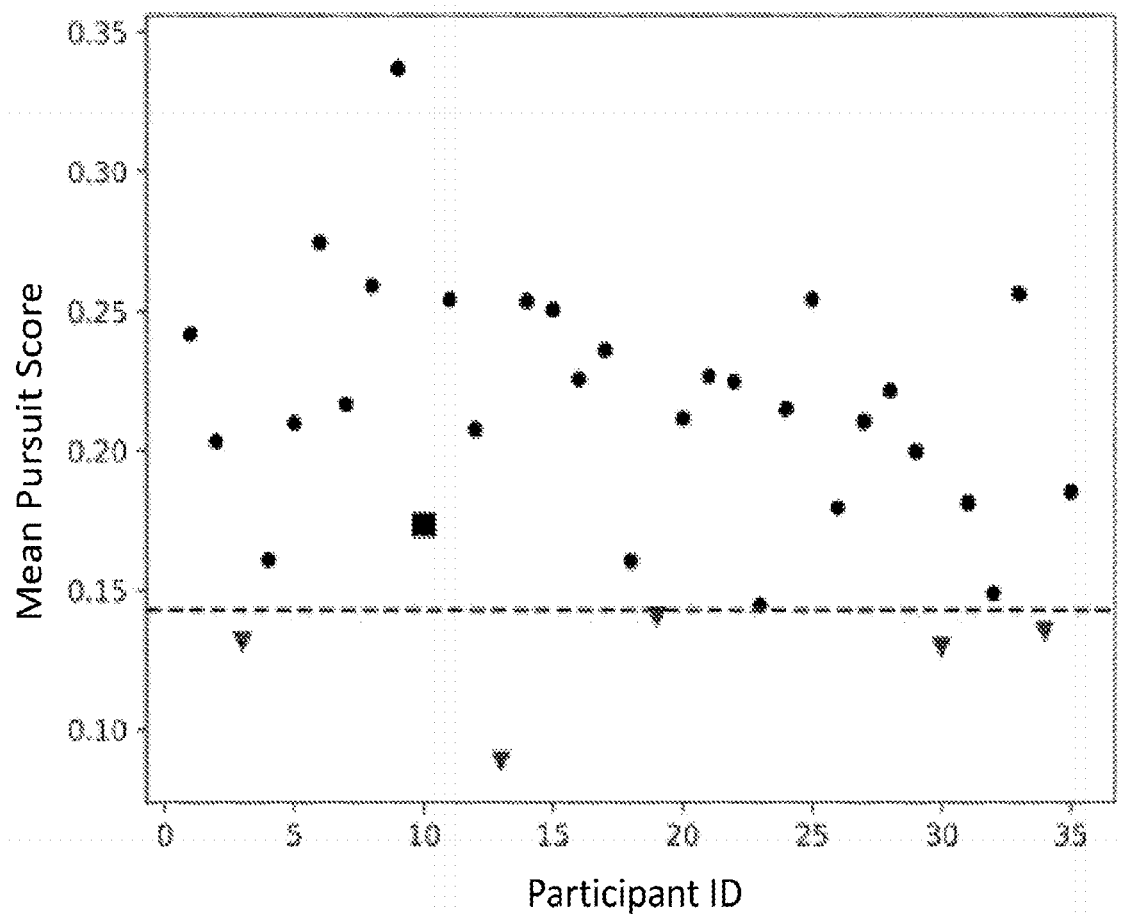
FIG. 3 depicts Scatterplot of Curveball mean pursuit scores. The dashed line (pursuit score=0.143) depicts the minimum pursuit score required for inclusion in the CSF results. Participants marked by red triangles fell below this threshold and were excluded from all analyses. The red dot represents a participant who was independently excluded due to an incompatibility between their asymmetric corrective lenses and the eye tracker.

Curveball's analysis protocol may account for 'dropped' trials by discarding the worst half of thresholds obtained for each spatial frequency (two out of four). Some participants, however, may still track the target too poorly overall to compute any accurate or consistent estimate of sensitivity. These participants may be identified by calculating the overall proportion of frames in which each participant met the Curveball criterion for smooth pursuits over all runs and conditions of the task (the "pursuit score" for that participant). Sample overall mean pursuit scores for participants are depicted in FIG. 3. Five participants were excluded due to having an overall mean pursuit score below 0.143, i.e. one out of seven frames (triangles below the dashed line in FIG. 3). This was a predetermined minimum tracking score required to prevent the Curveball trial from terminating. These additional exclusions are noted in the analyses below and the excluded threshold data are faded in corresponding figures. The reliance of Curveball on smooth pursuit ability is discussed in further detail below.

One additional participant (square in FIG. 3) was excluded because the eye tracker had difficulty integrating the gaze estimates from the participant's left and right eyes, which was likely due to strong asymmetric correction for a large astigmatism (cylindrical power of OD −1.25, OS −5.75). This problem can be avoided by only taking monocular measurements for participants with incompatible eyewear. Other participants with smaller correction for astigmatism or bifocal lenses are not affected.

The Curveball procedure depends on a minimum quality of smooth pursuit ability, but the contrast sensitivity thresholds it produces should not be strongly dependent on the precise quality of each participant's smooth eye movements beyond the required amount. This would suggest that the Curveball task was effectively only measuring smooth pursuit ability. This possibility was tested by regressing mean sensitivity across the standard Curveball runs on pursuit ability.

Figure 4:
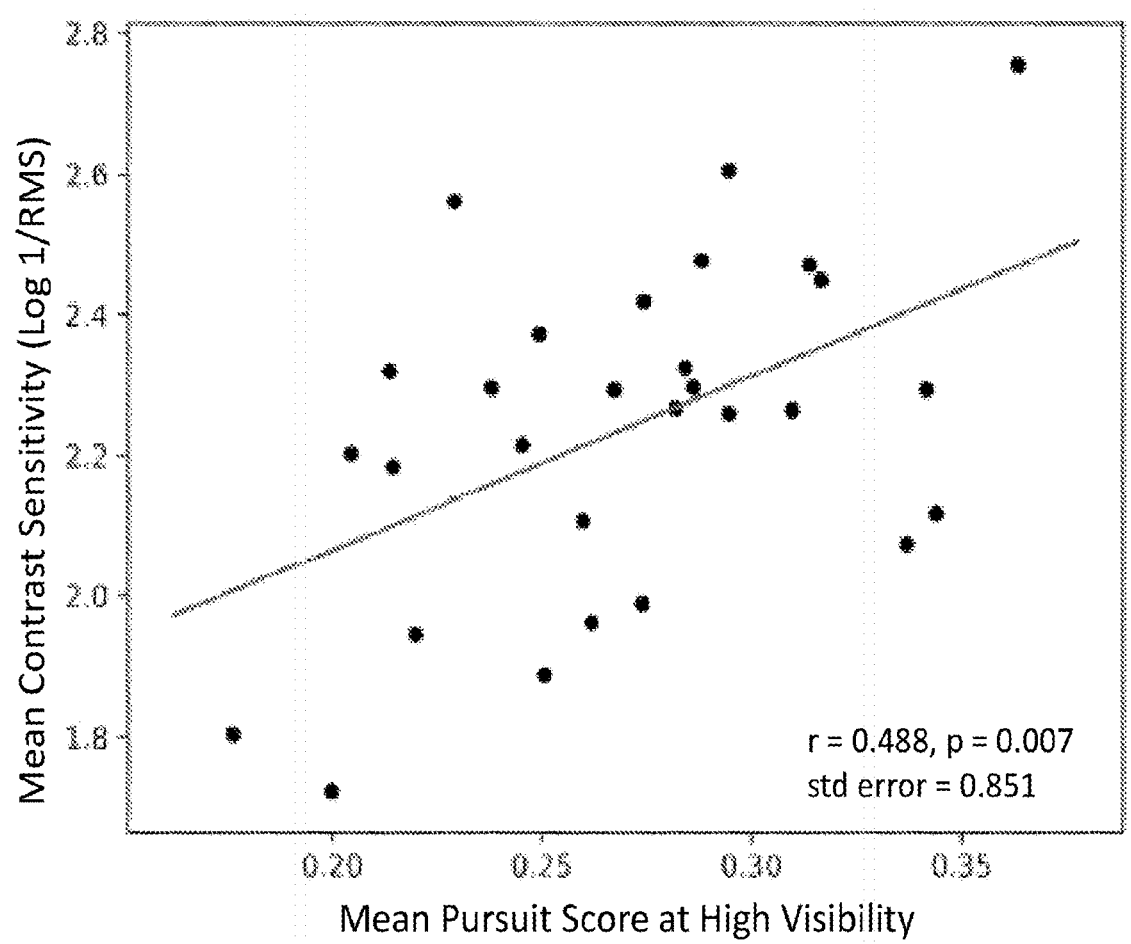
FIG. 4 depicts a regression plot of mean contrast sensitivity against mean pursuit score for high-visibility stimuli. Each point represents a different participant. Sensitivity and general pursuit-ability were moderately correlated. The methods of the invention can be applied to these embodiments.

Mean sensitivity will naturally be related to overall pursuit score, as participants with better contrast sensitivity spend a greater proportion of time tracking the noise target instead of waiting for trials to terminate. This conflating factor may be accounted for by only examining pursuit scores from periods in which the noise target was likely to be visible to all participants: a spatial frequency of 1 CPD (the peak sensitivity for most participants) and RMS contrast of 0.01 or greater (log sensitivity of 2). FIG. 4 depicts mean contrast sensitivity over three standard Curveball runs (vertical axis) against this high-visibility pursuit score (horizontal axis) for each participant. A linear regression revealed that mean sensitivity was weakly but significantly predicted by this tracking score, r=0.488, p=0.007, with a large standard error of 0.851 log units of sensitivity (approximately half the height of a typical CSF curve). This indicates that participants who were better at smoothly tracking a highly visible target tended to achieve better contrast thresholds, but not to a strong degree. Participants who were better at tracking the target may have been slightly more likely to continue tracking for a short interval after its contrast was reduced below threshold (but before the target could change direction). Alternatively, smooth pursuit ability and mean contrast sensitivity may be inherently related through some measure of general visual function.

Figure 12:
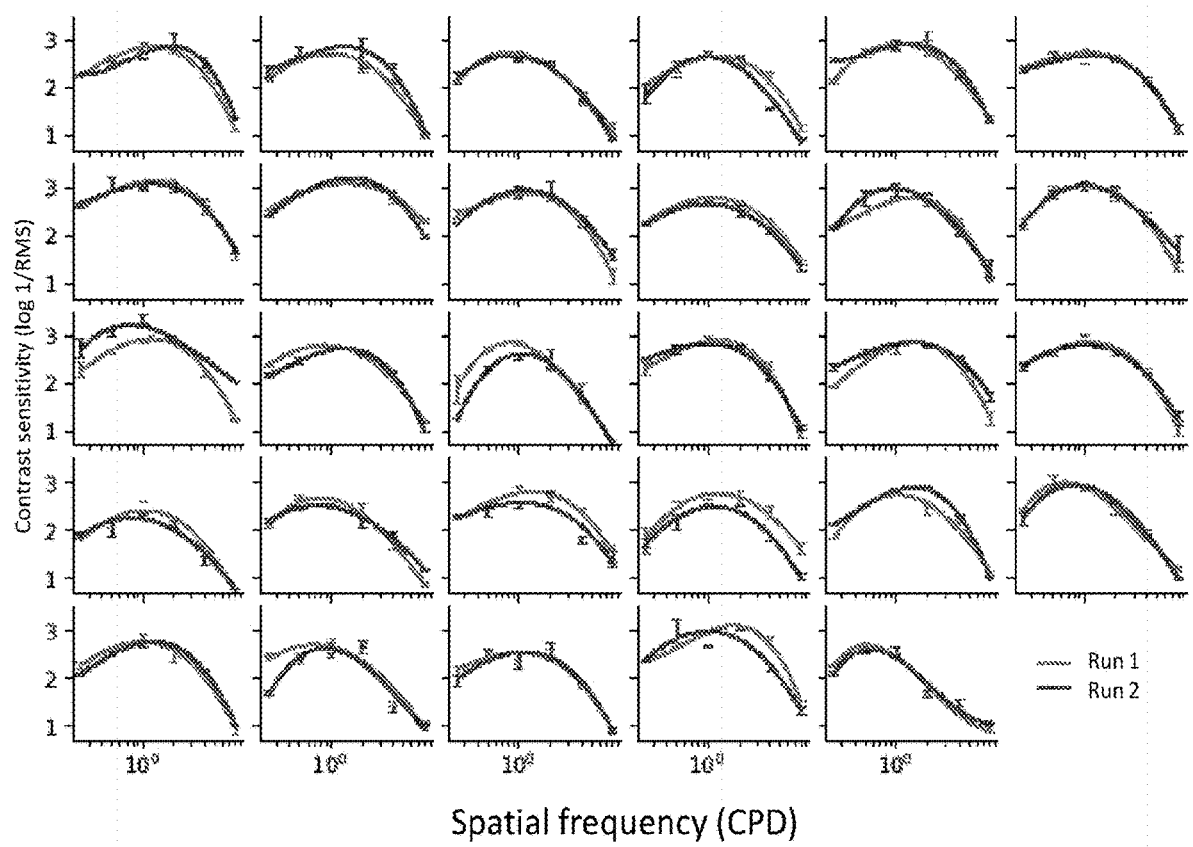
FIG. 12 depicts same-day repeatability of Curveball mean thresholds. Each subplot depicts the CSFs for a participant obtained from the first (blue) and second (purple) Curveball runs within the first testing session. Horizontal axes represent spatial frequency in log scale and vertical axes represent log units of RMS contrast sensitivity. In this and subsequent figures, error bars represent .+-0.1 SEM and the smooth curves correspond to the optimal cubic polynomial fits. The methods of the invention can be applied to these embodiments.

The same-day repeatability of the standard Curveball task was analyzed by comparing thresholds estimated during a first Curveball run (performed before the 4AFC staircases) and a second (performed after) in the first experimental session. These thresholds are plotted together for each of the twenty-nine included participants in FIG. 12. The horizontal axis in each subplot represents spatial frequency on a log scale and the vertical axis shows log 10 units of RMS contrast sensitivity. The limits and scale of the axes are identical in each subplot. All future figures of CSF data have the same layout and axes as FIG. 12.

Figure 5A:
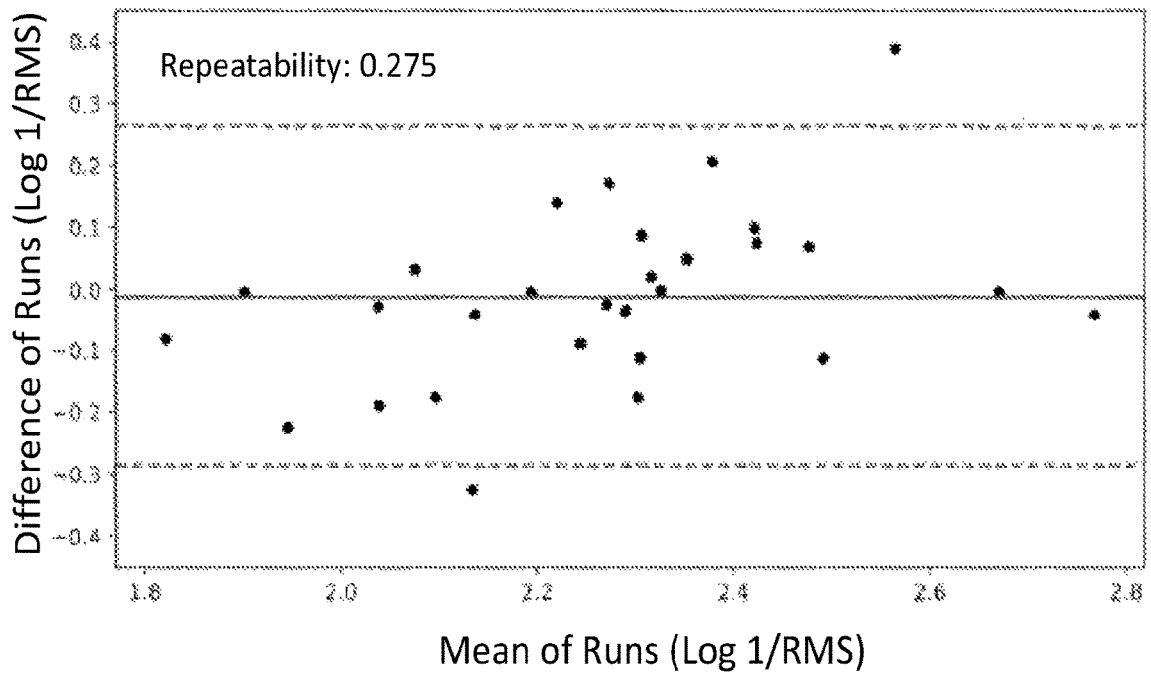
FIGS. 5A and 5B depict Bland-Altman plots for same-day and different-day repeatability, respectively. The first standard Curveball run from the first testing session has been compared with the second run from the same session (FIG. 5A) and the standard run from the second session on a different day (FIG. 5B). The vertical and horizontal axes represent the difference and mean of the two conditions compared in each case. The coefficient of repeatability in log units of sensitivity is depicted in the top-left of each plot. The solid black line marks the mean difference and the dashed lines represent the 95% limits of agreement (mean.+-.coefficient of repeatability). The methods of the invention can be applied to these embodiments.

Same-day repeatability can be visualized in the Bland-Altman plot depicted in FIG. 5A. This figure depicts the difference in mean sensitivity between Curveball runs for each participant plotted against the mean of the two runs. The horizontal lines represent the 95% limits of agreement. The same-day coefficient of repeatability was 0.275 log units of RMS contrast sensitivity. A substantial proportion of the same-day variance was contributed by one participant who performed much better on their second run of the task (uppermost data point in FIG. 5A). The coefficient of repeatability decreases to 0.236 if this outlying participant is discounted.

Figure 5B:
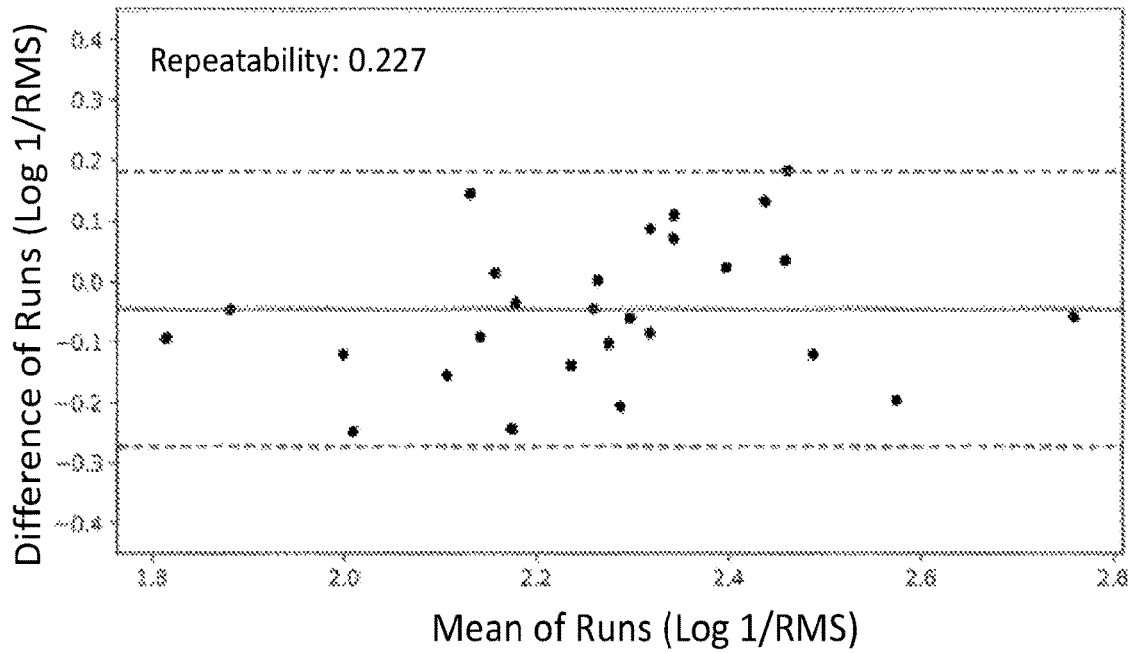
Figure 13:
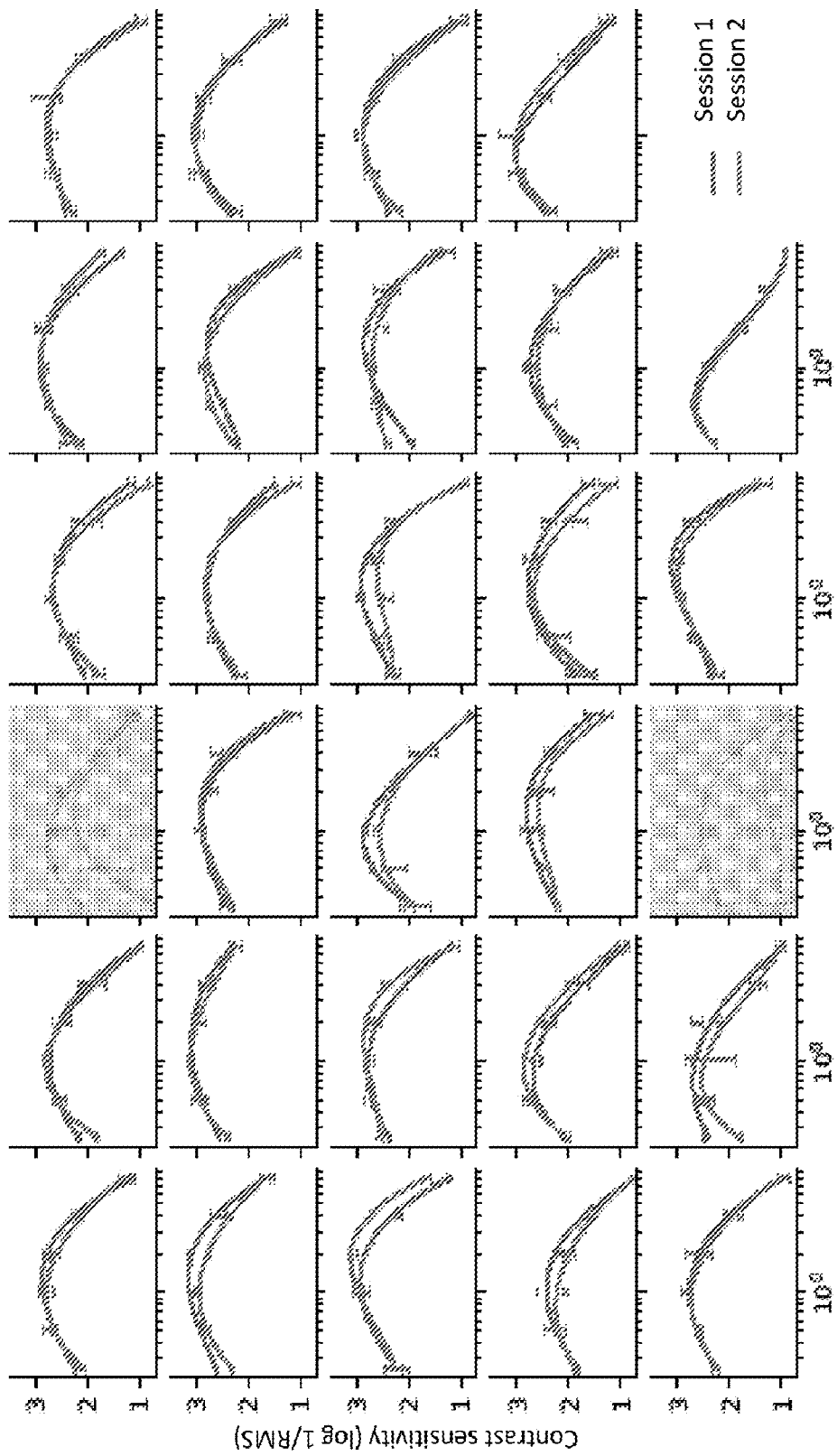
FIG. 13 depicts different-day repeatability of Curveball mean thresholds. The layout is identical to FIG. 4, but the lines now represent mean sensitivity in the first (blue) and second (green) testing sessions. The faded subplots represent two participants whose pursuit scores were below the exclusion threshold in the second session's standard Curveball run. The methods of the invention can be applied to these embodiments.

Different-day repeatability was analyzed in an analogous way to same-day repeatability. Thresholds from the first Curveball run in the first session were compared against thresholds from the standard Curveball run in the second experiment for each participant (FIG. 13). The faded subplots indicate two participants whose ability to smoothly pursue the stimulus fell below the exclusion threshold in the second session, which led us to exclude them from this analysis. The coefficient of repeatability was 0.227 log units of sensitivity, as shown in the Bland-Altman plot depicted in FIG. 5B, which is similar to the same-day repeatability. There was no significant correlation between mean sensitivity in the second session's run and the run's position (from first to fourth) in the random ordering of conditions in the second session, r=0.025, p=0.897, which suggests that participants did not become noticeably fatigued during the second session. Overall, our analysis indicates that Curveball is a highly repeatable measure of contrast sensitivity, both within a single testing session and across different days.

If Curveball is a valid measure of contrast sensitivity, the CSFs formed from its thresholds at different spatial frequencies should correspond closely to the CSFs assessed using conventional report-driven psychophysics. This relationship was tested by comparing CSFs estimated using Curveball with CSFs obtained from the traditional 4AFC staircase task completed in the same session. Separate analyses were conducted for the static and moving gratings in the 4AFC task. One participant was excluded from the comparison with the static 4AFC thresholds due to a sensitivity outlier at 2 CPD, which was likely produced by a run of false positives from correct sub-threshold guesses.

Figure 14:
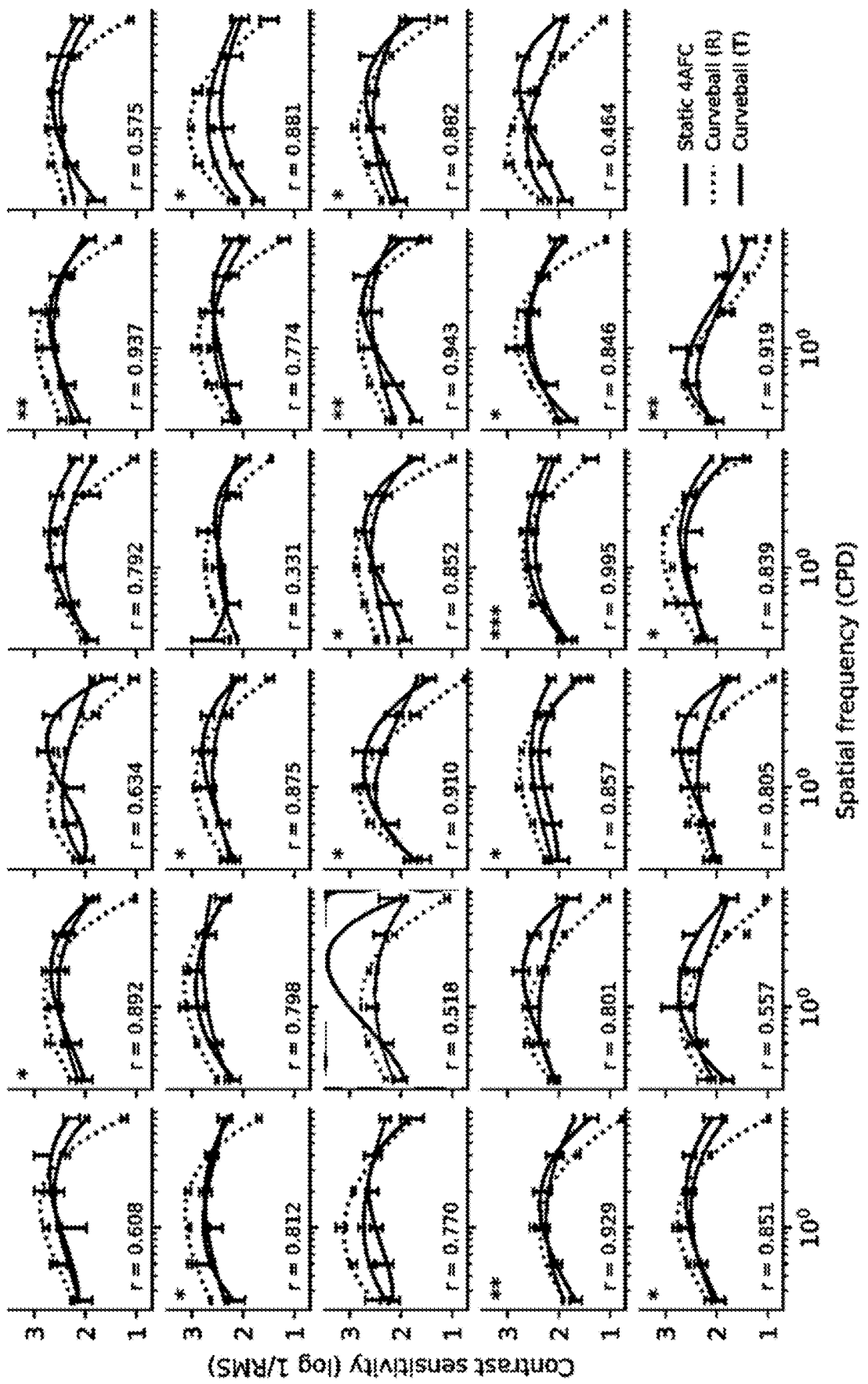
FIG. 14 depicts Curveball thresholds vs. static 4AFC thresholds. The layout and axes are identical to FIG. 12. The dotted and solid blue lines represent the raw and transformed Curveball CSFs, respectively, and the black lines represent the CSFs estimated from the static gratings in the 4AFC staircase task. The faded subplot in the third row denotes one excluded participant who achieved an impossible threshold at 2 CPD in the staircase task. This excluded data was not used to optimize the free transformation parameters for the other participants. Error bars in the 4AFC data here and in FIG. 8 represent .+-0.1 SEM, which was computed using the last four between-reversal runs of each contrast staircase. The methods of the invention can be applied to these embodiments.

The correlations between the raw Curveball thresholds and static 4AFC thresholds are only moderate (mean correlation of 0.681.+−0.0.170), but this is not surprising: past work has shown that the CSF elicited by moving stimuli is shifted down in spatial frequency (i.e. horizontally to the left) relative to the CSF for static stimuli. This shift in peak sensitivity may be accounted for by allowing the Curveball thresholds to differ by up to an affine transformation. The scaling, shearing, and vertical offset parameters of the transformation for each participant were optimized over the pooled thresholds from the remaining twenty-seven participants (i.e. a 'leave one out' model). The raw (dotted blue) and transformed (solid blue) Curveball thresholds are plotted together with the static 4AFC thresholds (black) in FIG. 14. The affine transformation significantly improved the mean correlation across participants to 0.790.+−0.0.154, t(27)=4.044, p<0.001. This indicates that the global affine transformation captured a large systematic difference in threshold estimates between the Curveball task and static 4AFC task, and that this difference comprised a large proportion of the between-task variance.

Figure 15:
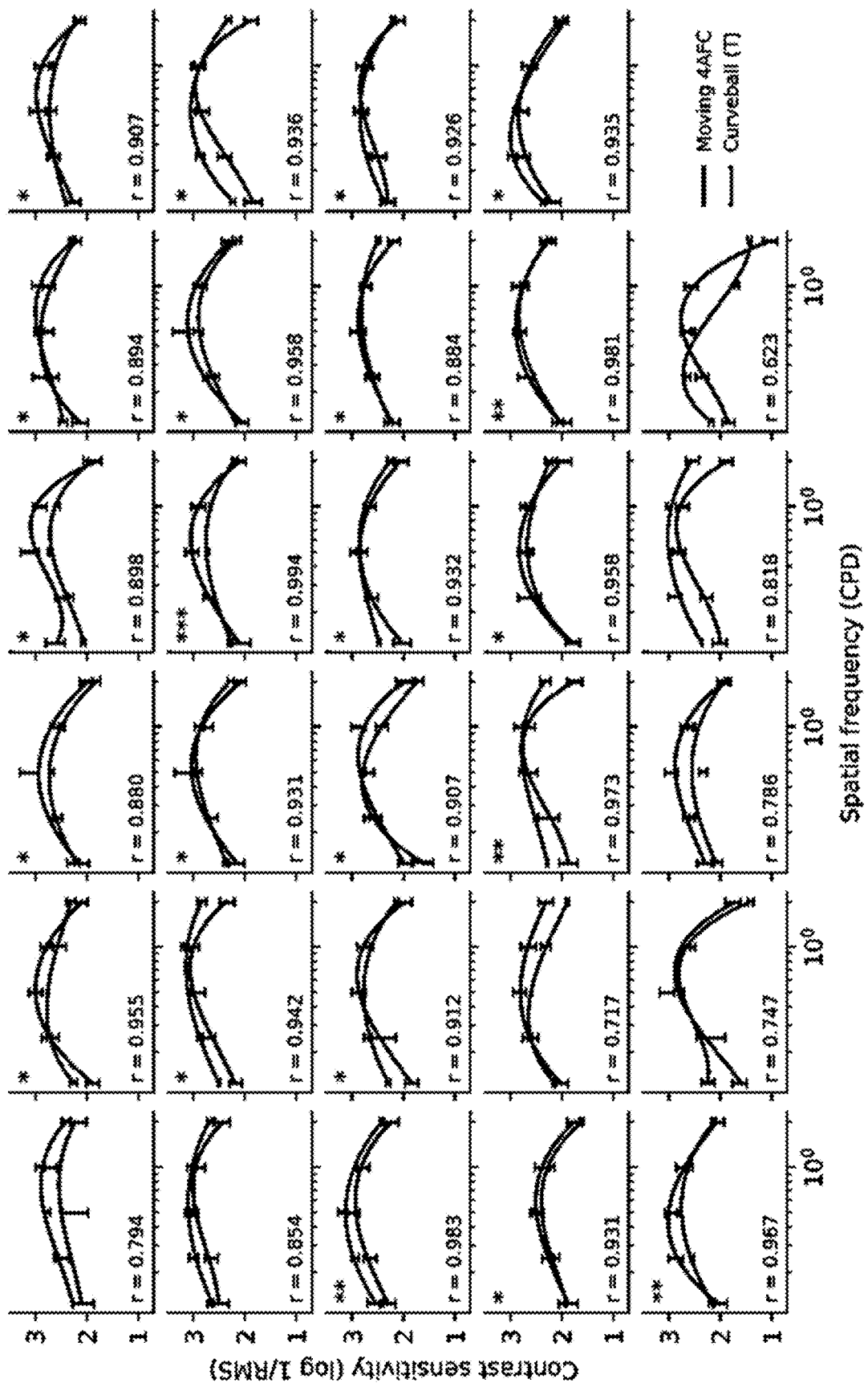
FIG. 15 depicts Curveball thresholds vs. moving 4AFC thresholds. The layout is identical to FIG. 7, but the horizontal axis of each subplot has been shifted to accommodate the lower range of spatial frequencies. The black and blue lines represent the CSFs estimated from moving gratings in the 4AFC staircase task and noise patches in Curveball, respectively. The Curveball spatial frequencies have been reduced by one octave, and the highest value removed, to account for the systematic horizontal shift in the CSF between tasks. No additional participants were excluded from this analysis. The methods of the invention can be applied to these embodiments.

The moving gratings in the 4AFC task were necessarily from a lower and more restricted range of spatial frequencies than the static gratings in the same task (which were not aliased by motion) or Curveball noise patches (which were filtered to avoid temporal aliasing). We accounted for this difference before comparing the moving 4AFC thresholds and Curveball thresholds by simply translating the Curveball thresholds to the left by one log unit (i.e. halving each spatial frequency) and dropping the highest Curveball spatial frequency. This transformation alone was sufficient to determine that the shapes of the Curveball CSFs were highly correlated with the CSFs estimated from the moving gratings in the 4AFC (FIG. 15). The mean correlation was 0.907.+−0.0.074 and was significant at the 0.05 level for nineteen out of twenty-nine participants. Allowing for an additional global affine transformation in the same way as the static gratings had no significant impact on these correlations, t(28)=−1.116, p=0.274.

Overall, these analyses indicate that CSFs obtained using Curveball are well matched by thresholds obtained from both static and moving gratings in a 4AFC task after the systematic shift in the CSF is considered, which in turn suggests that Curveball is a valid measure of contrast sensitivity. Notably, Curveball's CSFs appear to fall between the curves elicited by static and moving stimuli in conventional discrete psychophysics.

Figure 16:
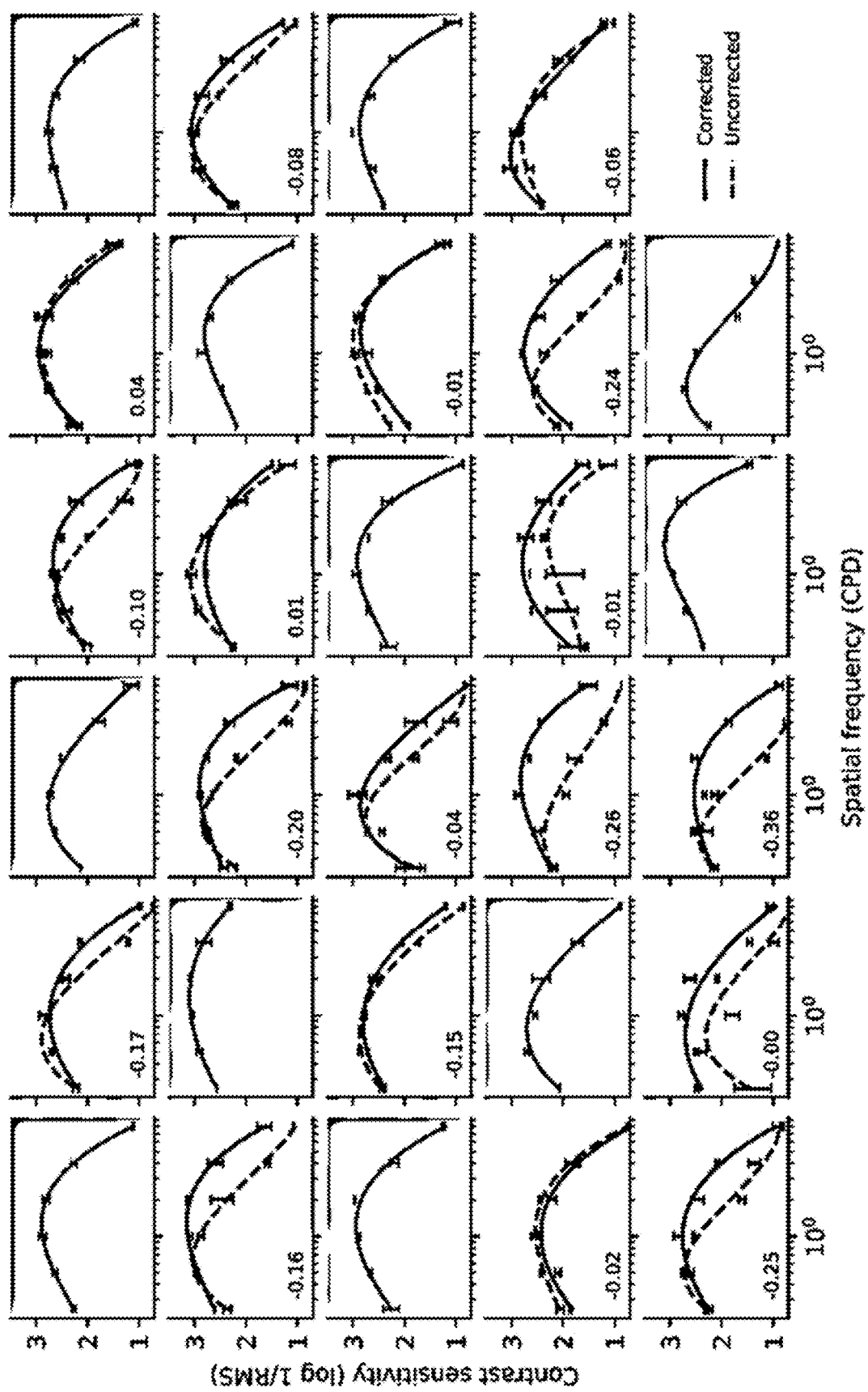
FIG. 16 depicts Curveball thresholds measured with and without visual correction. The layout and axes are identical to FIG. 12. The solid blue and dashed red lines represent Curveball CSFs obtained with and without corrective eyewear, respectively. The shear in the uncorrected CSF curve relative to the corrected curve is given in the bottom-left corner of each subplot. The standard Curveball thresholds for participants who did not complete the uncorrected condition have been left grayed out in this figure to permit easy comparison across figures. No other participants were excluded. The methods of the invention can be applied to these embodiments.

The CSFs produced by Curveball should be sensitive to the differences in visual acuity induced by refractive correction. Specifically, participants' contrast sensitivity should decrease more rapidly as a function of spatial frequency as their acuity worsens (i.e. when they remove their corrective lenses). If this is true, we would expect to find a relationship between the magnitude of the leftward shift in the CSF peak and the difference in eye chart acuity measured with and without visual correction. This relationship was examined for the eighteen participants with corrected-to-normal vision who performed an additional standard Curveball run without their corrective eyewear. The uncorrected Curveball CSFs for these participants are depicted together with their standard corrected Curveball CSFs in FIG. 16.

Figure 6:
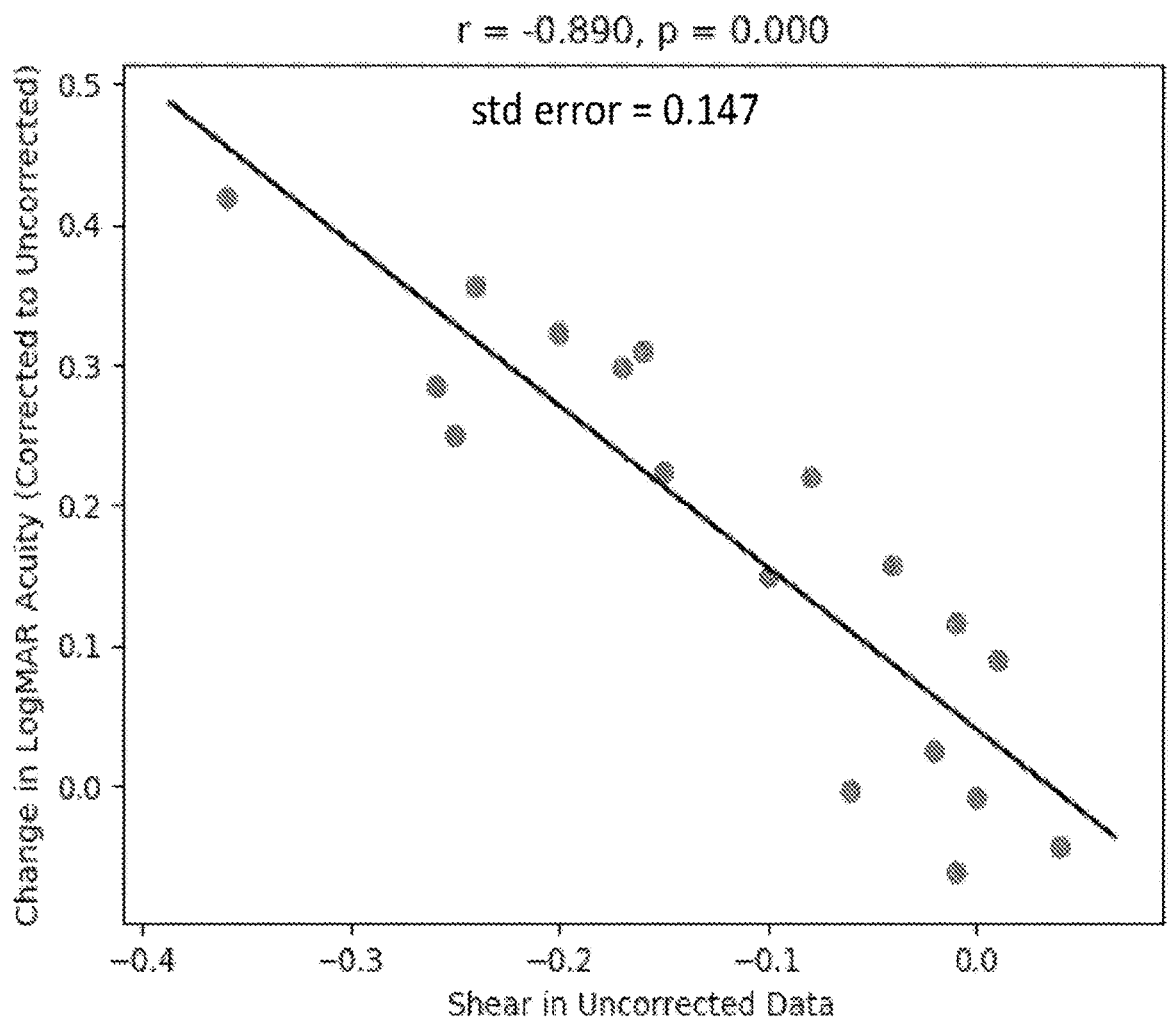
FIG. 6 depicts Regression plot of uncorrected change in Log MAR acuity against uncorrected CSF shear. Each point represents one of the eighteen participants who completed a Curveball run without their corrective eyewear. The change in acuity was significantly predicted by the shear of the uncorrected CSF relative to the corrected CSF in Curveball, in that larger shear values were associated with a greater loss of acuity (i.e. a more positive Log MAR value). The coefficient, p-value, and standard error of the correlation are depicted in the top-right corner and the gray line represents the line of best fit. The methods of the invention can be applied to these embodiments.

The effect of visual correction on the CSF was quantified with an affine transformation similar to that applied when comparing Curveball data to the 4AFC task, but in this case, separate transformations were optimized to account for the difference in corrected and uncorrected CSFs for each participant. The shear parameter of this transformation was then used as a measure of the change in the CSF curve: more negative shear indicates that the peak of the CSF shifted further to the left in the uncorrected condition relative to the corrected condition. A linear regression analysis revealed that uncorrected shear was highly and significantly predictive of the change in Log MAR acuity measured with the Tumbling 'E' chart, r=−0.890, p<0.001, in that more negative shear was associated with a larger loss of acuity from lack of corrective eyewear (as more positive Log MAR values represent worse vision). These data are shown with the line of best fit in FIG. 6. Interestingly, the line of best fit was approximately y=−x (slope of −1.153 and intercept of 0.041). These results indicate that Curveball is highly sensitive to changes in visual acuity and refractive correction, which is expected of a useful measure of spatial visual function. It may be possible to estimate an individual's acuity from a single Curveball CSF, but this would require an empirical investigation of their absolute relationship.

Figure 17:
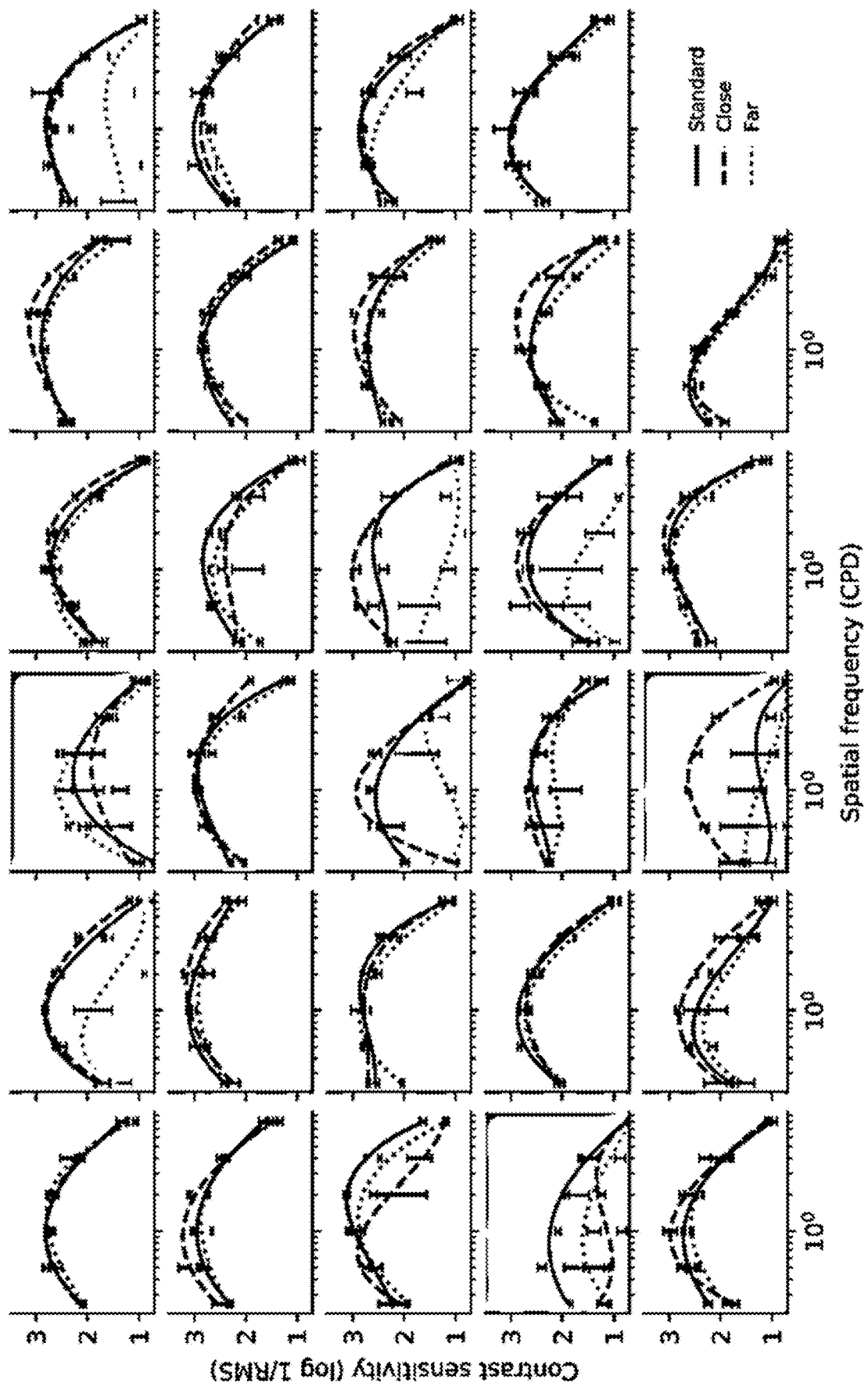
FIG. 17 depicts Curveball thresholds measured at different distances. The layout and axes are identical to FIG. 12, but correlations are not shown. The solid green, dashed blue, and dotted orange lines represent CSFs measured at standard (62 cm), close (47 cm), and far (77 cm) distances, respectively. Note that the spatial frequency units on the horizontal axis are only correct for the standard distance of 62 cm. The semi-grayed subplots indicate participants who were excluded from the far condition analysis due to an insufficient pursuit score in that condition; the fully-grayed subplots indicate participants who were excluded from both distance analyses due to insufficient pursuit scores in at least two of the three conditions. The methods of the invention can be applied to these embodiments.

If Curveball is to be a useful measure of vision in a range of clinical settings, it is helpful to have an understanding about how dependent the procedure is on participant distance. The task's reliance on distance was assessed by comparing the thresholds and pursuit scores measured from the standard (62 cm), 'close' (47 cm), and 'far' (77 cm) Curveball conditions in the second testing session (FIG. 17). The data suggest that deviations from the optimal eye tracker distance resulted in a greater number of 'dropped' trials for several participants. Pursuit ability fell below the exclusion threshold for two participants in the close condition and seven participants in the far condition. When these participants were excluded from the appropriate conditions, paired comparisons revealed that there was no significant difference in pursuit score between the standard and close conditions, t(25)=−0.790, p=0.437, but there was a significant decrease of 0.018 in pursuit score in the far condition relative to the standard condition, t(21)=3.536, p=0.002. This suggests that the increase in distance in the far condition added enough noise to their gaze data to push multiple participants' pursuit ability below the level required for the Curveball algorithm to accurately estimate sensitivity. Note that these findings apply specifically to the Tobii 4C eye tracker used in the experiment.

A repeated measures ANOVA revealed no change in mean sensitivity between the standard and close distance conditions, F(1,26)=0.499, p=0.486, but did reveal a significant interaction between distance and spatial frequency, F(5, 130)= 3.036, p=0.013. A linear trend contrast found that the difference between the standard and close conditions became significantly more positive as a function of increasing log spatial frequency, t(26)=2.221, p=0.035. This is expected: moving closer to the display increases the actual spatial frequency of each stimulus in degrees of visual angle and should shift the CSF to the right, as the presented stimuli are identical.

An analogous repeated measures ANOVA found a significant decrease of 0.135 log units of RMS sensitivity in the far condition relative to the standard condition, F(1,20)= 38.981, p<0.001, but unlike in the close condition, there was no interaction between this distance change and spatial frequency, F(5,100)=0.592, p=0.706. The expected leftward shift in the CSF may have been masked by the increase in eye tracker noise at greater distances. Participants may have also found it more difficult to attend to the task in the far condition due to the screen's reduced presence in their field of view, which could explain the reduction in mean sensitivity.

Together, these results suggest that Curveball (when using the Tobii 4C) is more tolerant of decrements in user distance than increments relative to the optimal distance of 62 cm. This is likely a permanent limitation of display-mounted eye trackers, but its effect on the task may decrease as technology improves. For many participants, however, the task appears to remain reliable at a range of distances compatible with the display-mounted eye tracker.

Two participants were excluded from analysis of the 'dark' condition due to a tracking score below the exclusion threshold in that condition. A subsequent repeated measures ANOVA revealed that turning off the room lights had a small significant positive effect on mean sensitivity relative to the standard lights-on Curveball run conducted in the same testing session, F(1,26)=4.670, p=0.040, but no significant interaction between the change in illumination and spatial frequency, F(5,130)=0.944, p=0.455. These results suggest that a large change in room illumination (a decrease of 10 cd/m.sup.2) has a minimal effect on Curveball performance. CSFs for the 'dark' condition are not depicted due to their high similarity to the curves from the standard conditions.

The findings provide strong evidence that Curveball is a reliable, accurate, and efficient objective measure of contrast sensitivity at working distance. Task repeatability was high, both within the same session (coefficient of repeatability 0.275) and across different days (coefficient of repeatability 0.227), and its consistency across changes in room illumination suggest that it is suitable for practical clinical settings. The procedure produces CSFs that are (a) systematically related to the CSFs obtained from both static and moving stimuli in a conventional staircase task and (b) highly predictive of the difference between corrected and uncorrected eye chart acuity. Curveball contrast sensitivity estimates are distorted in a predictable way as the user moves closer to the screen and the algorithm's ability to detect smooth tracking appears to degrade only gradually as distance from the eye tracker varies between the optimal and maximum distance allowed by the hardware. This suggests that the participant's distance can be continuously monitored using the eye tracker and used to compute the true spatial frequencies being measured in each trial when estimating the CSF. The display-mounted eye tracker used here required only half a second of one-point calibration at the start of the task for our smooth pursuit detection algorithm to perform well.

Critically, Curveball requires no volitional perceptual report and can potentially be administered with no instruction. Many participants reported that it was easier and more engaging than the conventional staircase task and indicated that they preferred the second Curveball-only testing session. Most importantly, the task is no less efficient than the best existing procedures based on perceptual report—even those that use Bayesian statistics and CSF curve parameterization—and is potentially more efficient due to its allowance of a flexible number of repeats per threshold. A single threshold estimate for one spatial frequency takes less than ten seconds to obtain, and the precision of that estimate rapidly improves as additional repeats are conducted and dropped trials discarded. These dropped trials are likely to cause the trial to end much earlier than it otherwise would, and future implementations of Curveball could potentially detect these false negatives and respond by adapting the number of repeats needed for that spatial frequency in real time. For example, participants who exhibit a sufficiently low difference between the first two repeats of a given threshold, in addition to a sufficiently high pursuit score, could skip the third and fourth repeats at that spatial frequency.

Another advantage of Curveball (and gaze-based tasks in general) is the ability to extract other information about the participant's visual function from the eye tracking data collected during the procedure. This could make the task even more useful for testing participants with brain injury or other cognitive impairments, as these individuals are likely to exhibit low-level ocular or cortical dysfunction that can be measured from Curveball even if accurate contrast thresholds cannot be obtained. The ability to smoothly pursue a target, for example, is a useful dimension of visual function that Curveball already exploits to determine stimulus visibility. Curveball data could be further leveraged to determine how pursuits and saccades depend on stimulus orientation, movement direction, and location in the visual field, all of which naturally vary as the target moves around the display. Catch-up saccade latency could be inferred from the participant's response when the target appears at the start of a new trial or abruptly rebounds off the edge of the display. Specific dysfunctions, such as pathological nystagmus, could also be detected and quantified from the gaze data. It may even be possible to quantify aspects of attention based on high-level responses (e.g. patterns of visual search across the display).

A system according to the present invention may include a display; an eye-tracking device configured to detect the gaze position of one or both eyes; and a pursuit detector executed by at least one processor. The pursuit detector may be configured to (1) display one or more variable-contrast stimuli, each of which moves from a first location on the display to a second location on the display; (2) receive, from the eye-tracking device, the gaze position signal detected from one or both eyes as each variable-contrast stimulus moves from the first location to the second location; (3) calculate a set of trajectory-match scores by comparing the gaze position signal to the position of each stimulus over a time window; (4) identify, based upon the set of trajectory-match scores, the visual function of a subject; and (5) display additional audiovisual stimuli coincident with or between the movements of the variable-contrast stimuli to facilitate attention, provide a break to the participant, or provide feedback on performance.

The pursuit detector may further be configured to produce real-time, frame-by frame inferences about stimulus visibility based on the similarity between gaze and stimulus trajectories, to determine a trajectory-match score for each stimulus on every frame by, for example, (1) identifying and discarding samples of gaze position that are not consistent with the known limitations of the human eye and/or human visual system; (2) computing a stimulus trajectory function from each variable-contrast stimulus position signal on each frame as that stimulus moves from the first location to the second location; (3) constructing an expected gaze trajectory function for each stimulus trajectory function based on the most recent value of the gaze position signal on each frame; (4) computing an actual gaze trajectory function on each frame from the gaze position signal over the same time window as the stimulus trajectory function; and (5) calculating a trajectory-match score for each variable-contrast stimulus based on the quantitative spatiotemporal agreement between that stimulus's expected gaze trajectory function and the participant's actual gaze trajectory function on each frame. Sixty trajectory-match scores may be produced per stimulus per second.

A method in accordance with the present invention may include the steps of (1) displaying, on a computer screen, one or more variable-contrast stimuli that each move from a first location to a second location; (2) generating, by an eye-tracking monitor, a gaze position signal as each visual stimulus moves from its first location to its second location, the gaze position signal detecting a position of one or both eyes; (3) filtering the gaze position signal by discarding samples that are not consistent with known limitations of the human eye and/or human visual system; (4) calculating a trajectory-match score from comparison of the gaze position signal and stimulus position over a time window; (5) identifying the visual function of the subject based upon the trajectory-match score; and (6) displaying additional audiovisual stimuli during or between the movements of the variable-contrast stimuli to facilitate attention, provide breaks, or provide performance feedback. The variable-contrast stimulus may increase in contrast or decrease in contrast. The stimulus contrast change may be perceptually continuous. The variable-contrast stimulus may change in a step-wise manner by multiplying the current contrast by a variable between 0.5-1.5 on each frame.

In an alternative embodiment, a plurality of Curveball stimuli may be depicted and move smoothly in a pattern on the display, rather than stimuli randomly drifting around the display one at a time. For example, a predetermined number of Curveball stimuli (e.g., six stimuli) may move smoothly in a circle in the center of the display or may follow a path through an invisible grid or other geometry. When the observer begins to track one of the stimuli, a number of the other stimuli may temporarily disappear to disrupt global motion cues that could allow the observer to continue tracking a (perceptually) featureless local region. For example, if six Curveball stimuli are depicted as moving smoothly in a circle in the center of the display, the four stimuli closest to the stimuli that the observe begins to track (i.e. all but the stimulus directly opposite the tracked stimulus) may temporarily disappear. The stimuli may reappear when the observer stops tracking. The ongoing presence of the opposite stimulus ensures that the observer is always provided with a new stimulus to track upon losing the first; the observer may return to a stimulus later if they have not yet pursued it to threshold.

In this embodiment, rather than continuously fading, tracked stimuli may change in both contrast and spatial frequency simultaneously after each discrete burst of tracking. The progression of each stimulus may follow a sequence of combinations of spatial frequency and contrast (a "sweep") through the 2D CSF space, rather than varying only contrast (i.e. a vertical vector) or only spatial frequency (i.e. a horizontal vector). The variation of both contrast and spatial frequency may ensure that the stimulus continually refreshes its appearance, which counteracts the tiresome nature of extended tracking.

These sweep sequences may take the form of line segments or vectors through the CSF space that may share a common origin, which may be chosen empirically to be maximally visible to the widest range of observers with different visual ability (e.g. high contrast and low-medium spatial frequency). These vectors may "puncture" various points along the observer's CSF curve at a more perpendicular angle than conventional horizontal or vertical sweeps, which reduces any negative effects of measurement error on curve estimation.

Progress along each sweep sequence may "spill over" into progress along nearby sweep sequences (e.g. adjacent sweep vectors following similar angles away from the origin), which is an optimization made possible by conservative, empirically-justified assumptions about the continuity and curvature of the CSF. Sweep sequences that have been indirectly progressed this way may start further along their sequence (e.g. away from the shared vector origin) than they normally would, which removes redundant trials from the task and saves time. The subset of sweep sequences ("basis sweeps") whose threshold is the most empirically informative about the overall CSF and sensitivity to disease may be identified through testing and may be tested first, to ensure that information is collected in the most efficient manner given the limited time of many hospitalized participants. The single most informative sweep vector is referred to herein as the Concuity sweep. Also, eye movement kinematics generated as part of the evidence-of-visibility score computations, such as tracking accuracy, direction, duration, and saccade interspersion, may be collected and analyzed as metrics of visuomotor function.

Figure 7:
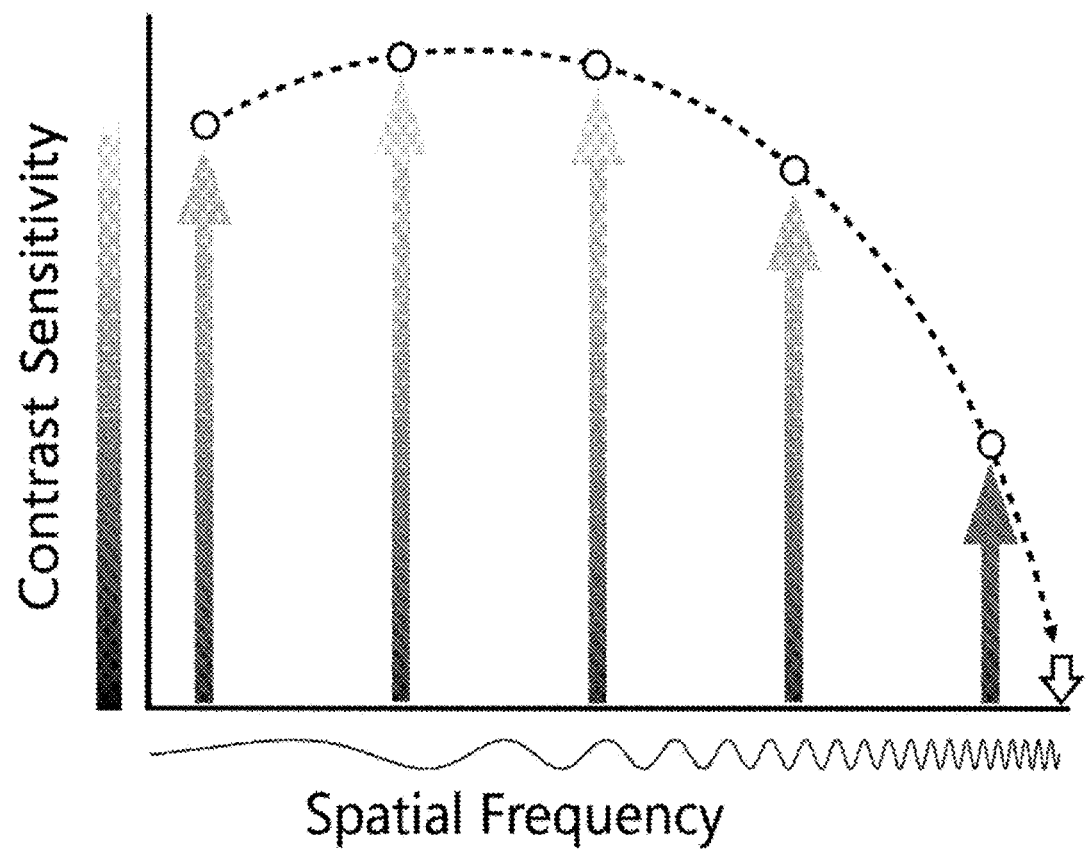
FIG. 7 is a graph showing an assessment of acuity and generation of a contrast sensitivity function (CSF).

As shown in FIG. 7, spatial vision can be specified as a 2D stimulus visibility space, with spatial frequency varying on the X-axis (sinusoidally-undulating line), and contrast varying on the Y-axis (vertical rectangle with changing contrast relative to the white background). Acuity may be defined as the highest spatial frequency that is visible at maximal stimulus contrast (e.g. open arrow). A contrast sensitivity function (CSF), shown as a dotted line, may be estimated from the measurement of minimal contrast visibility over a range of spatial frequencies (vertical arrows and open circles). The CSF intersects with the X-axis (closed arrow) at acuity. The Curveball approach to measuring a CSF proceeds through multiple stimulus variations much faster than approaches that use discrete trials, and spends less time (trials) near the limit of ability, which reduces the fatigue of testing.

Figure 8:
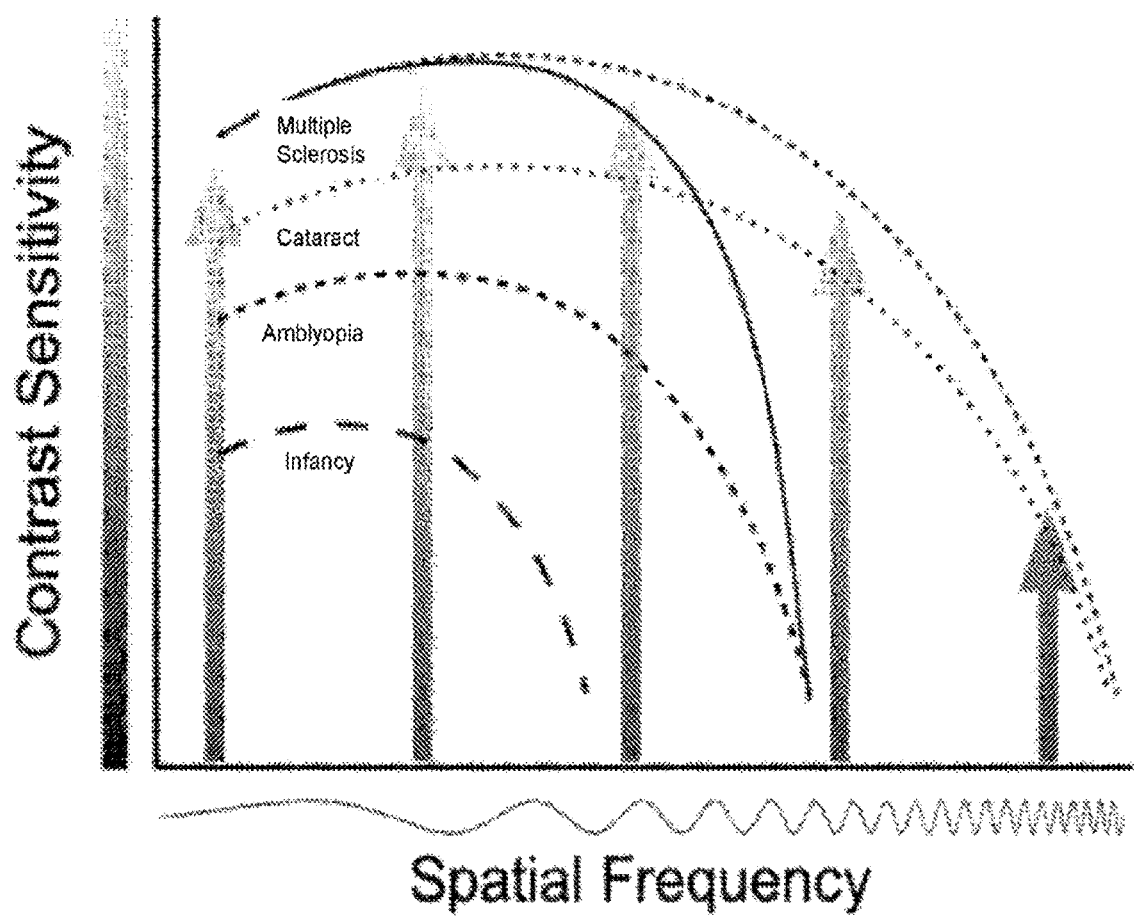
FIG. 8 is a graph depicting limits of measuring acuity and CSFs.

Referring to FIG. 8, acuity may be used as a simple and fast measure of spatial visual health and disease, but it has limited sensitivity to detect small, but meaningful variation in brain-related visual function. Measures of contrast sensitivity are often superior to acuity in detecting spatial visual abnormalities, but the time and expertise required to generate CSFs is substantial, and thus, contrast measures are not generally used for such diagnostic purposes. Moreover, no typical single measure of contrast sensitivity (e.g., one of the vertical arrows) would satisfactorily define the interaction between spatial frequency and contrast, nor capture the type of variation that typically distinguishes visual disorders and age-related change in visual function (illustrated with idealized overlaid example CSFs). Using idealized sample data, FIG. 8 depicts how conventional testing trajectories that are strictly vertical or horizontal may entirely fail to intersect the CSF at any point.

Figure 9:
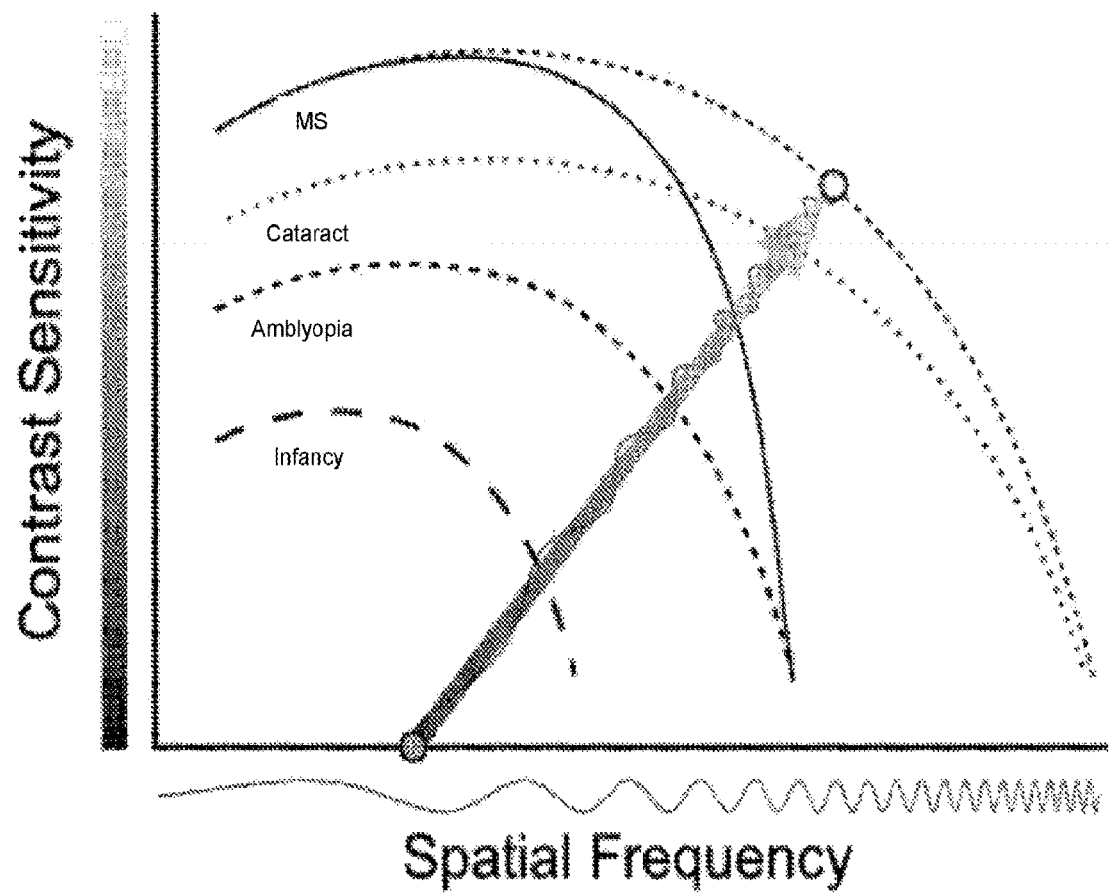
FIG. 9 is a graph depicting a sweep vector approach to obtaining a single measure of spatial visual function.

Unlike defining a single point on the CSF through the manipulation of contrast only, or through measuring visual acuity, as is typically done, as shown in FIG. 9, the most informative single point on the CSF (open circle on outer dashed line) may be measured by simultaneously varying contrast and spatial frequency during a single gaze-driven sweep through the 2D stimulus visibility space (angled arrow with gradated luminance and spatial frequency variation) using the present invention's algorithm. This approach holds promise to identify a visual deficit that single measures of contrast sensitivity would miss. The vector would intersect with CSFs that vary widely in their shape as a function of disease and age. The optimal position of the sweep's origin (gray-filled circle on the X-axis), as well as the angle of the vector that defines the optimal proportion of spatial frequency variation to contrast variation, may be estimated and refined empirically through the statistical analysis of a large database of CSFs.

Figure 10:
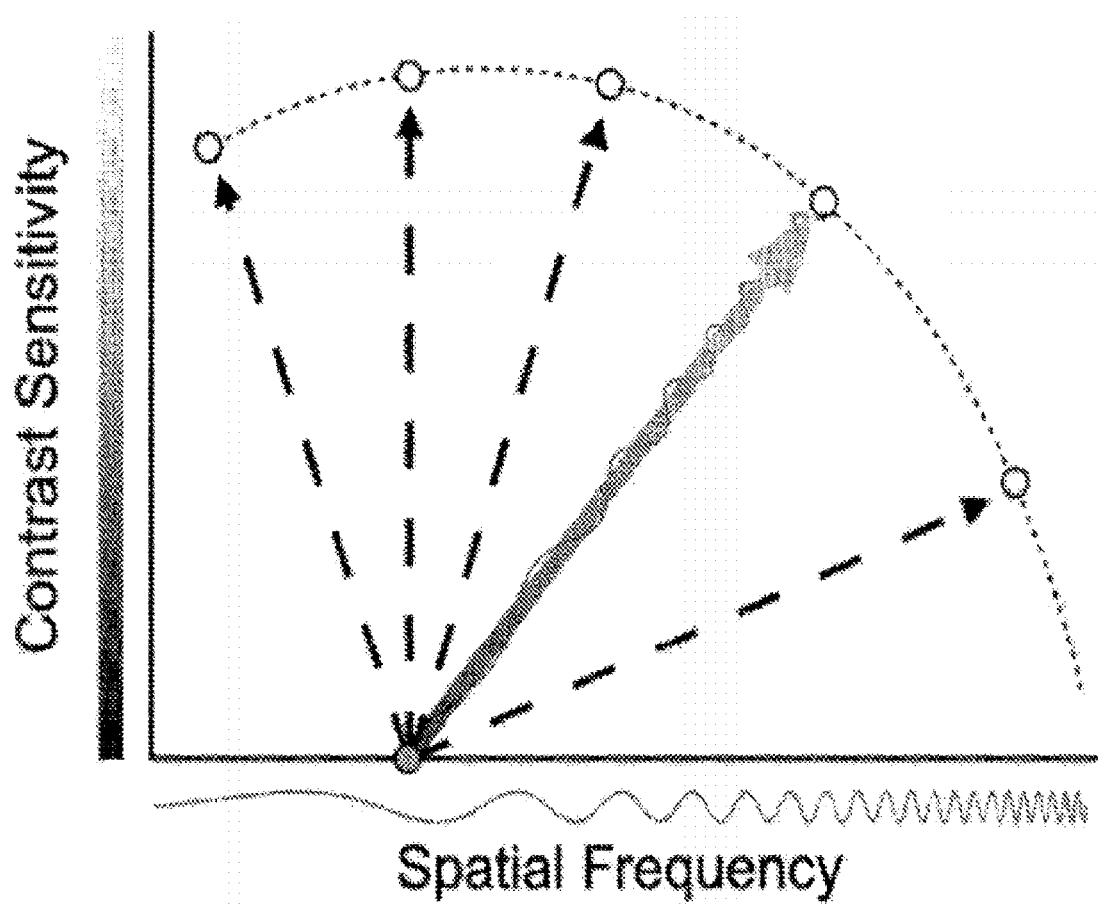
FIG. 10 is a graph depicting a "sweep trajectory" approach to measuring the Concuity point on the CSF.

Referring to FIG. 10, the "sweep" approach to measuring the Concuity point on the CSF can be generalized to the measurement of the rest of the CSF. The simultaneous manipulation of contrast and spatial frequency (dotted lines with arrows) is an efficient way to generate the points that define a CSF (open circles) because (a) the stimulus at the origin is common to all vectors, and is optimally visible to the widest range of viewers, and (b) the simultaneous manipulation of contrast (a continuous variable) and spatial frequency (a discrete variable) makes the stimulus more interesting and more easily tracked compared to stimuli that vary in contrast alone. In other applications, sweep sequences other than vectors may be useful. For example, sweep sequences that "skate" along an existing estimate of a participant's CSF could be used to make detailed refinements to that CSF.

Figure 11A:
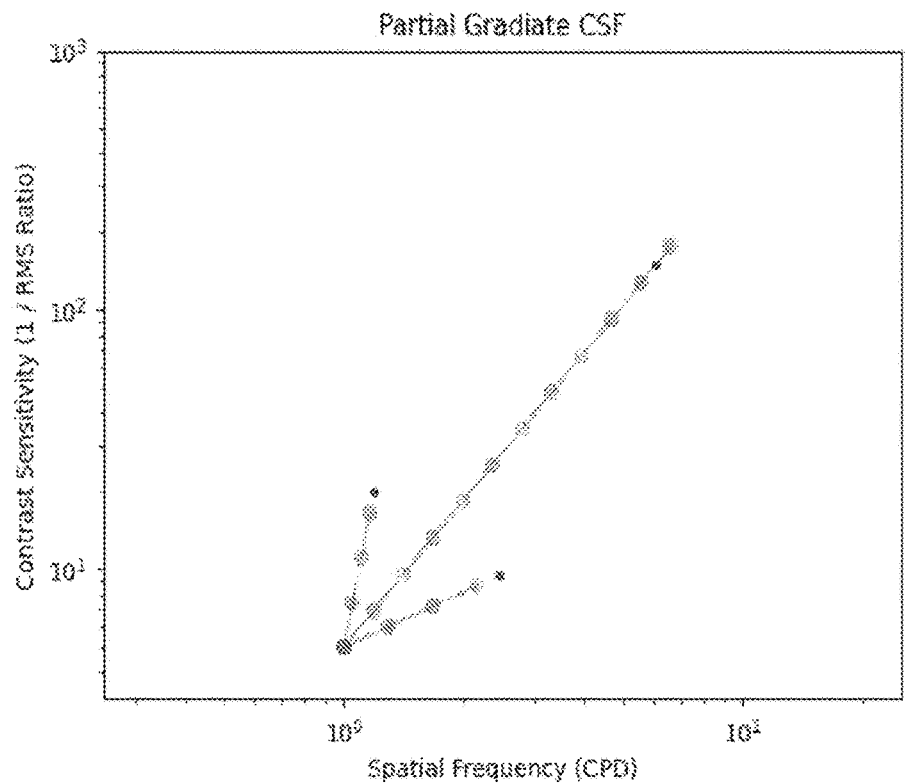
FIGS. 11A and 11B are graphs depicting a "sweep trajectory" approach to measuring CSFs.
Figure 11B:
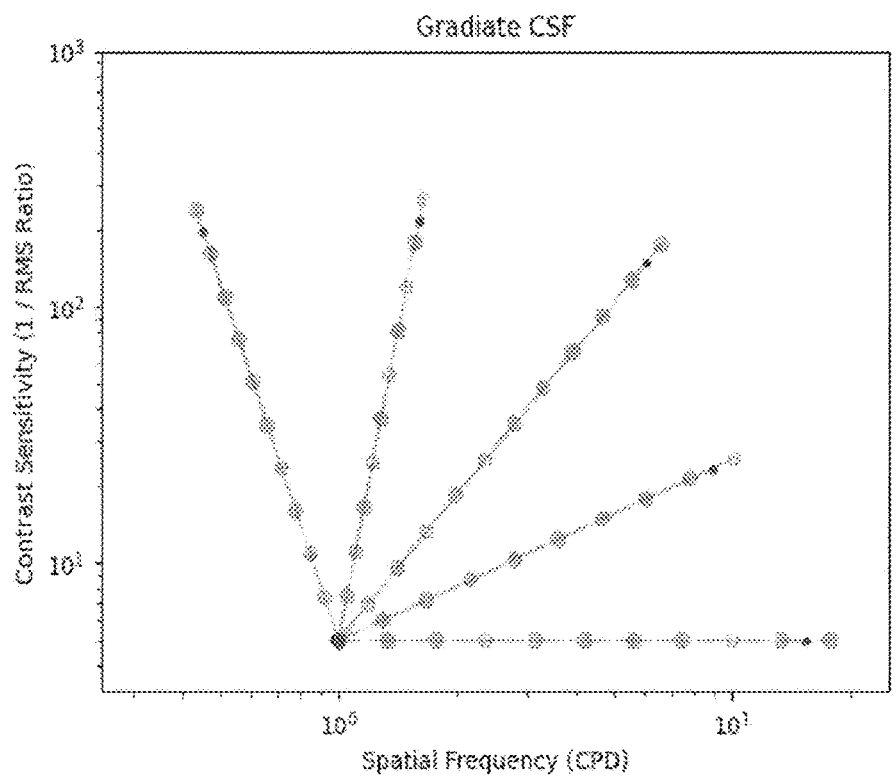

Referring to FIGS. 11A and 11B, the "sweep vector" approach to measuring CSFs also enables a way to predict the visibility of stimuli on adjacent vectors, which can be used to improve the efficiency of the task. The visibility of stimuli on sweep vectors adjacent to (i.e. a small angular difference away from) the sweep vector currently being measured can be predicted with high confidence, because (a) human CSFs generally approximate a continuous arc regardless of disease and age, (b) the sweep vectors used to measure a CSF emanate from the same origin, and (c) each vector intersects the CSF at an approximately perpendicular angle. The graphs of a Curveball CSF experiment in progress (FIG. 11A) and at completion (FIG. 11B) show how the procedure works. Each straight line of dots represents a single sweep vector. Each dot in the sequence represents a single stimulus that was successfully tracked, causing the next stimulus in the sweep to appear. The final dot in each sequence was not successfully tracked, which terminates the sweep and defines one point of the CSF. As progress is directly made along the tested vector via successful tracking, indirect progress is also made (but to a lesser degree) along adjacent vectors (shorter lines on either side) even though they will not be directly tested until later. Thus, when each of those adjacent sweep vectors are subsequently tested, the initial stimulus conditions do not have to be those at the origin (central dot), but instead can begin at the limit of inferred indirect progress already made within that sweep (final dots on the short vectors). This is because there is a high probability that the participant can easily see the stimulus, even though the specific stimulus conditions were never tested. This process of generalizing the visibility of stimuli from one sweep vector to another reduces the time required to measure a CSF because highly visible stimuli do not need to be repeatedly assessed. The exact degree to which progress along one vector can be inferred from progress on another (for example, inference weight as a function of relative sweep angle and relative sweep progress) may be empirically determined by sampling the natural range of CSFs within specific populations.

A system in accordance with the present invention may include a display, an eye-tracking device configured to detect the gaze position of one or both eyes of the person, a non-transitory memory having a machine-readable medium comprising machine executable code; and one or more processors coupled to the memory, said one or more processors configured to execute the machine executable code. Execution of the machine executable code may cause the one or more processors to (1) generate an ordered sequence of a set of one or more visual stimuli; (2) present at a first area of the display a first visual image; (3) receive from the eye-tracking device data indicating a second area of the display to which the person's gaze is directed; (4) pre-calibrate the eye-tracking device based on the location of the first area and the location of the second area; (5) store in the non-transitory memory a software algorithm that sets a path for each of the visual stimuli to follow on the display; (6) present on the display a first visual stimulus of the set of one or more visual stimuli, wherein the first visual stimulus moves in a path on the display as set by the software algorithm for a first period of time; (7) receive from the eye-tracking device data indicating a gaze position and an eye position of one or both eyes of the person for the first period of time; (8) calculate an evidence-of-visibility score by comparing the gaze position and eye position of one or both eyes of the person during the first period of time to the position on the display of the first visual stimulus during the first period of time; (9) modify, based upon the evidence-of-visibility score, the contrast or spatial frequency of the first visual stimulus; (10) calibrate the eye-tracking device based on the data indicating a gaze position and an eye position of one or both eyes of the person and the position of first visual stimulus over the first period of time; and (11) determine, based upon the evidence-of-visibility score, a visual function of the person.

Calculating the evidence-of-visibility score may produce real-time, frame-by frame inferences about stimulus visibility based on the relationship between gaze and stimulus trajectories, to determine an evidence-of-visibility score for each stimulus on every frame. The method of calculating the evidence-of-visibility score may include (1) identifying and discarding samples of gaze position that are not consistent with the known limitations of the human eye and/or human visual system; (2) identifying and discarding samples of gaze position that are malformed by blinks, failure to attend to the display, and/or invalid person position relative to the display; (3) identifying fixation events by analyzing the 2D dispersion metric of gaze position and comparing gaze position to the positions of all presented stimuli; (4) identifying saccade events by detecting high-velocity, high-acceleration, near-linear eye movements and comparing the endpoint of the saccade to the positions of all presented stimuli; (5) identifying smooth pursuit events by detecting mid-velocity, low-acceleration eye movements; and/or (6) identifying optokinetic nystagmus events by detecting smooth pursuit events interspersed with saccade events occurring in near-opposing directions.

Additionally, the method of calculating the evidence-of-visibility score may comprise: (a) computing a stimulus trajectory function from each variable-spatial-frequency variable-contrast stimulus position signal on each frame as that stimulus moves from the first location to the second location; (b) constructing an expected gaze trajectory function for each stimulus trajectory function based on the most recent value of the gaze position signal on each frame; (c) computing an actual gaze trajectory function on each frame from the gaze position signal over the same time window as the stimulus trajectory function; (d) identifying target-tracking events for each presented stimulus based on the quantitative spatiotemporal agreement between that stimulus's expected gaze trajectory function and the person's actual gaze trajectory function on each frame; (e) calculating and applying both automated time decay penalties and added penalties from the absence of target-correlated gaze events; (f) computing evidence weights for each type of gaze event using the geometric statistics of the paths and appearance of the presented stimuli; and (g) computing an evidence-of-visibility score for each presented stimulus by calculating a weighted sum of evidence from all computed gaze events and penalties. Between 30-120 evidence-of-visibility scores may be produced per presented stimulus per second, depending on the refresh rate of the display.

Gradiate

Observers: Sixty healthy observers (34 female) participated. Observer age ranged from 11 to 74 years, with a mean of 34.95 and standard deviation of 13.85. Observers were recruited as volunteers from employees at the Burke Neurological Institute and their families and friends. Thirty-eight observers had corrective eyewear and were tested both with and without it. All observers provided informed consent under an approved institutional review board protocol and were not financially compensated. Experimental data were secured and managed with the REDCap database (Harris et al., 2009).

Apparatus: A 27-in. widescreen LCD Dell (Round Rock, TX, USA) Optiplex all-in-one computer was mounted on a wheeled stand with an articulated arm and outfitted with a Tobii 4C eye tracker (operating distance of 50-95 cm; sampling rate of 90 Hz) with a professional-level license (Tobii Technology, Stockholm, Sweden). Eye-tracker data were accessed with the Tobii Stream Engine library, which computes the gaze point on the display using one or both eyes (as detected in real time) and applies a small amount of smoothing to the data stream. The exact parameters of this smoothing are not accessible or modifiable with the Stream Engine library but resemble a simple sliding average over approximately 10-15 frames. Real-time control of stimulus behavior was programmed in Python using the Shady graphics toolbox (Hill, Mooney, Ryklin, & Prusky, 2019), which was also used to calibrate screen gamma. Minimum and maximum values of screen luminance were measured under the experimental illumination conditions with an ILT1700 radiometer (International Light Technologies, Peabody, MA, USA) as 10.0 cd/m2 and 221.1 cd/m2, respectively. Head movements were not restrained, and observers were given no specific instruction to keep their head still during the task. The Tobii 4C tolerates head movements well, and no observer experienced difficulty with the task due to their idiosyncratic preference for head versus eye tracking. The software was configured to blank out the screen and display a warning message whenever the eye tracker detected that the observer's eyes were closer than 520 mm or further than 720 mm from the screen.

Figure 19:
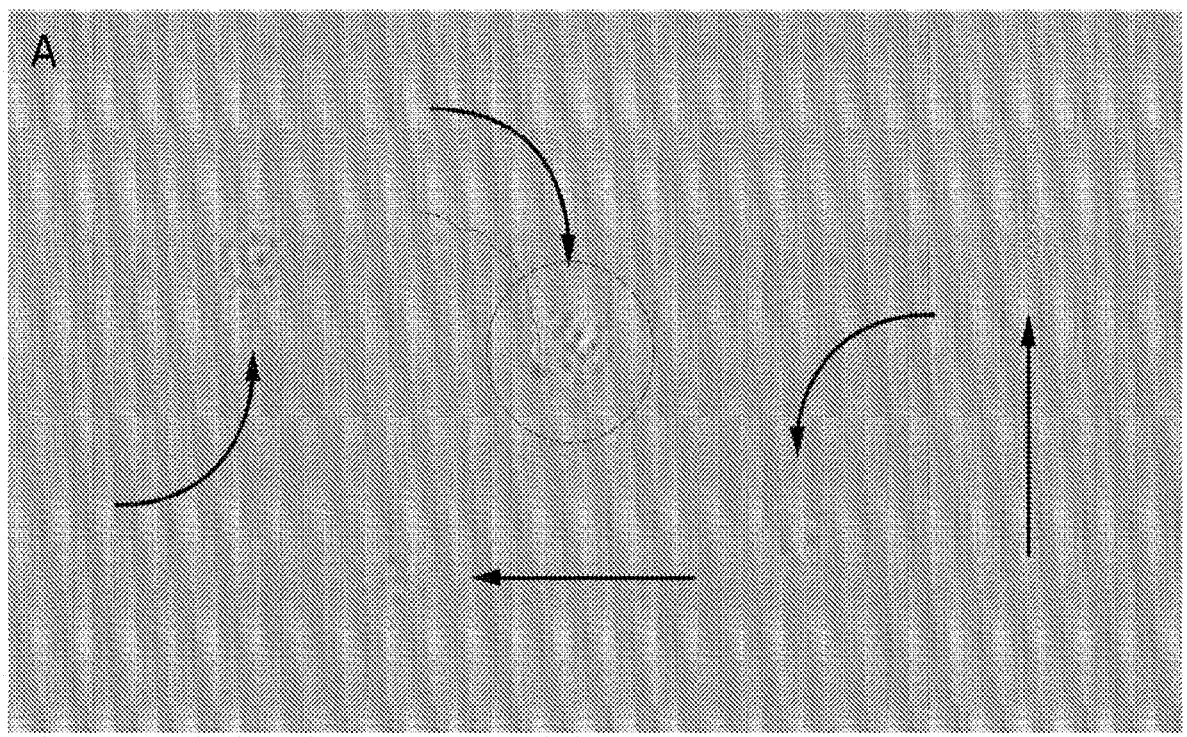
FIG. 19(A)-(B). (A) Screenshot from one trial of the Gradiate task, which measures thresholds along five radial sweeps in one presentation (see FIG. 18). Background and mean stimulus luminance are 0.5 normalized display luminance. Stimuli move around the screen randomly, as shown by the example arrows, making smooth turns as often as possible while avoiding collisions and synchronous movements. The Gradiate algorithm collects evidence about the visibility of each stimulus from the observer's eye movements and advances that stimulus by changing its spatial frequency and/or contrast as soon as visibility is inferred. The trial ends, and final thresholds are computed, after a period of no successful tracking of any stimulus. In this frame, the observer is currently tracking the central stimulus, as their gaze (green dot) both falls within its positional tolerance radius (red circle) and closely matches its recent trajectory (blue line vs. black arrow). See also Supplementary Movie S1 for a video of one complete trial. (B) Gaze (green) and target (black) X and Y traces in degrees of visual angle for one stimulus in another example trial. Timeline segments highlighted in red and blue indicate periods when position-based tracking and trajectory-based tracking were detected, respectively. The tracking types appear purple when overlapping. The vertical black dotted lines indicate when the stimulus was tracked enough to progress along its sweep. The dotted lines always have white backgrounds because the gaze sample buffers used to detect tracking are cleared whenever the stimulus changes appearance. In this example, the observer responds to a sharp change in target movement direction at 4.5 s and loses the ability to track the target at 7.5 s after the last dotted line. Brief periods of coincidental position-only tracking at 9.5 and 12.5 s are ignored while the observer makes saccades across the now perceptually empty display.
Figure 19:
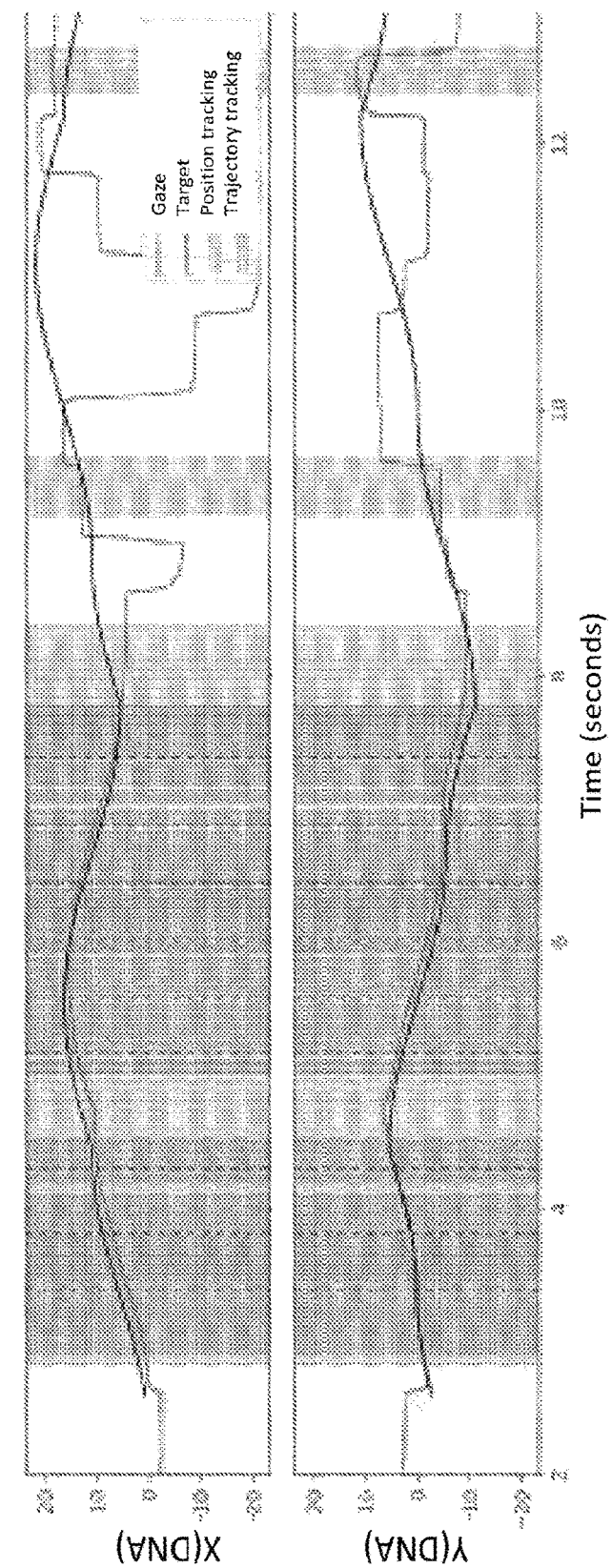

"Gradiate" task: Observers were presented with a set of filtered noise patches—each defined by a combination of spatial frequency and root-mean-square (RMS) contrast—that moved around the screen on a uniform gray background of normalized luminance 0.5 (FIG. 2A). An algorithm continuously inferred the visibility of each target in real time by updating an evidence counter based on the relationship between the observer's gaze and the changing position of that target. Positive evidence required the observer to exhibit tracking that fell within a position-based tolerance radius and a trajectory-based tolerance radius simultaneously, which was determined continuously at 60 Hz (i.e., every video frame). Position-based tracking error was calculated by summing the distances between target position and gaze position over the last eight frames. The error threshold was set to the radius of the stimulus (3°) plus an additional 2° and is depicted by the red circle around the central stimulus in FIG. 19A. Trajectory-based tracking error was calculated by summing gaze-target distances over the same eight frames after subtracting the most recent gaze-target deviation vector from each of those eight gaze samples. This component of the algorithm had a much stricter error threshold of 0.4°; it was therefore only satisfied when an observer's gaze closely matched the trajectory of the target but was not sensitive to any systematic deviation in position. This combination of a generous position-based tracking detector and strict trajectory-nased tracking detector was designed to reduce reliance on perfect eye-tracker calibration, which cannot always be obtained in clinical populations. Eye trackers that are miscalibrated by up to ~5° in any direction can be used without precluding either component of the tracking detection algorithm, provided that the eye tracker is calibrated to the correct display size. Blinks and other interruptions to the eye-tracker data stream were not classified or handled explicitly; tracking analysis required an additional eight frames of buffered samples to resume after any such data stream interruption occurred. Example gaze versus target position traces in the horizontal (X) and vertical (Y) screen dimensions are depicted in FIG. 19B, with periods of position-based and trajectory-based tracking highlighted in red and blue, respectively.

Gaze samples that satisfied both conditions were classified as smooth tracking and progressed the evidence counter of that stimulus by 5 units per frame. Samples that satisfied only the position-based tracking condition caused the evidence counter to remain unchanged, which allowed observers who tend to mix short bursts of smooth pursuit with frequent catch-up saccades ("saccadic trackers") to make progress. Samples that satisfied neither condition caused the evidence counter to decay at a rate of 1 unit per frame (to a minimum of zero evidence). When enough evidence of a target's visibility was collected (100 units), that target instantaneously updated its appearance by altering its spatial frequency and/or contrast by one step along a predetermined sweep through CSF space. The evidence counter for that target was then reset to zero and the process repeated. At the same time, a separate global evidence counter determined when no stimuli were visible to the observer and terminated the trial when it fell to a sufficiently negative value (−300 units). This global evidence counter was similarly increased when any target was tracked and decayed at a constant rate when neither tracking condition was met for any stimulus but was further penalized by saccades away from the display or into empty screen space by an amount proportional to the amplitude of the saccade. Saccade events were initially detected using a velocity threshold of 25°; false positives caused by eye-tracker noise were then filtered out by ignoring saccades that (a) were shorter than 50 ms, (b) included an instantaneous angle change of 450 or more, or (c) exceeded 900°/s in instantaneous speed. A threshold was recorded for each target halfway along the interval (in log-log space) between the point representing the last spatial frequency/contrast combination that was successfully tracked and the current (untracked) point. RMS contrast sensitivity (hereafter referred to as CS) was computed as the inverse of the RMS contrast ratio.

The trajectories of the Gradiate sweeps were defined as radial vectors with a common origin, equal magnitude, and directions separated by equal angles in a linear transformation of the log-log CSF space. This transformation was chosen through pilot testing such that a normative CSF was approximately mapped onto a circle of radius 0.5. The log-log values of the point (0.25 cpd, 0.5*101 CS) were mapped to (0, 0) and the log-log values of the point (12 cpd, 103.5 CS) to (1, 1). This box also encompassed the range of CSF curves we observed in our previous study (Mooney et al., 2018). Fifteen sweep vectors were defined in this space with unit magnitude and an origin corresponding to a spatial frequency of 1 cpd and 0.5*101 CS (i.e., a starting RMS contrast ratio of 0.2). The 15 sweeps were spread evenly between polar angles 109.703° and 0° (by an angular interval of 7.836°). These sweeps are depicted in log-log CSF space in FIG. 18.

Each of the 15 sweeps were divided into 16 steps, with each step determining the spatial frequency and contrast of a single narrow-band noise stimulus. Step size was determined such that a single sweep threshold took approximately 10 s to complete in pilot testing. These stimuli were generated by applying a circular-symmetric Hann window to a filtered noise pattern (1/f amplitude spectrum and random phase) subtending 6° of visual arc at the viewing distance of 620 mm. Each noise pattern was filtered with a band-pass filter centered on the target spatial frequency with a constant width of 0.34 octaves. Temporal aliasing at high spatial frequencies was prevented with an additional anisotropic filter, which removed all Fourier components with horizontal spatial frequency greater than 5.7 cpd (95% of the 6-cpd Nyquist limit of a stimulus moving at 5° per second on a 60-Hz display).

Figure 18:
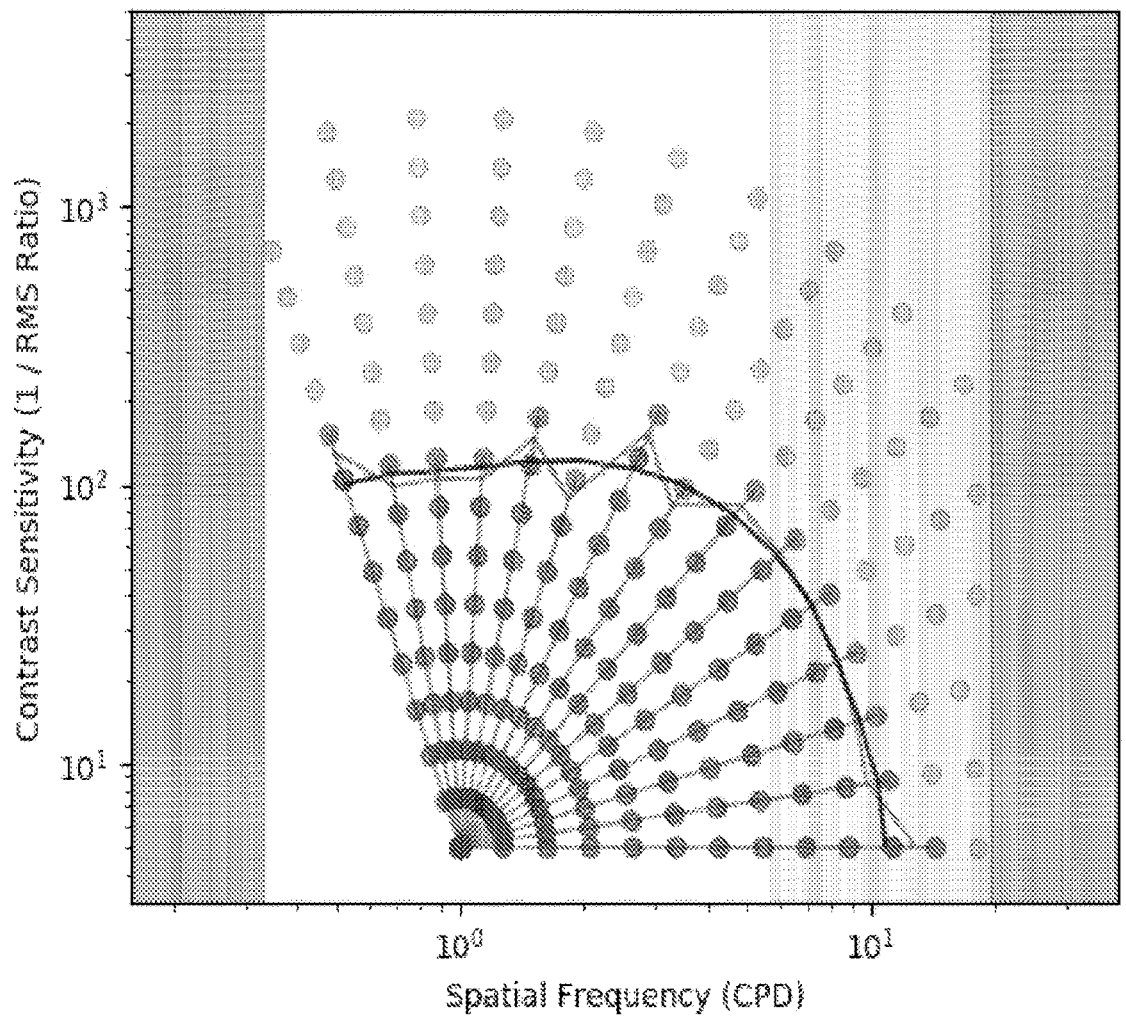
FIG. 18 is an example of a detailed CSF measured with Gradiate, with spatial frequency on the horizontal axis and contrast sensitivity on the vertical axis (log-log scale). Each dot represents one stimulus in a single radial sweep from a common origin, which observers make progress along through successful target tracking. The blue, red, and gray dots represent stimuli that this observer successfully tracked, failed to track, and never reached, respectively. Thresholds halfway between the final success and first failure are joined to form the CSF (gray line), with the black curve depicting a smoothed version. The dark gray regions to either side of the plot indicate spatial frequencies that could not be displayed due to stimulus size (at the low end) and screen resolution (at the high end), which truncated the leftmost and five rightmost sweeps. The light gray region indicates spatial frequencies that, when multiplied by the stimulus speed, put individual pixel fluctuations above the screen's temporal Nyquist limit; to render these stimuli, additional anisotropic spatial filtering was required to remove Fourier components close to the orientation of stimulus motion. This CSF was generated in about 2 min.

The orientation of each stimulus was yoked to its movement direction to ensure that the antialiased direction of the texture always matched the direction of motion. Stimuli with a target frequency above 19.416 cpd were not permitted to appear in the task: After antialiasing, these stimuli contain no power at any orientations that deviate up to 720 from the direction of motion, making them too difficult to track in our pilot testing. Similarly, spatial frequencies below 0.4 cpd could not be displayed with at least two full cycles in a texture subtending 6° of visual arc and were not permitted to appear. Excluding these stimuli truncated several sweeps that would otherwise broach very low or very high spatial frequency values, as shown in FIG. 18. In order to keep tracking error thresholds consistent, stimulus envelope size did not vary with spatial frequency, and higher spatial frequency stimuli consequently exhibited more cycles. Prior work with sine gratings has found that holding envelope size constant rather than number of cycles can have a small influence on the CSF (Savoy & McCann, 1975), but as this occurs predominantly at low frequencies, we determined that the trade-off with consistent error thresholds was worthwhile.

Five targets were presented to the observer simultaneously in each Gradiate trial, with their movements coordinated using a grid motion system. Each target moved from node to node in an invisible diamond grid along straight lines, making smoothed 90° turns at pseudo-random intervals. Movement rules prevented the targets from colliding, making synchronous movements, or repeating the same movement multiple times. If no movement in any direction was possible for a given target (e.g., because it was surrounded), it remained motionless until movement was possible, and any tracking of that target was ignored until movement had resumed. However, the most recently tracked stimulus always received priority for finding a valid movement.

LCA was measured with a variant of the Gradiate task that employed a single horizontal sweep with constant RMS contrast 0.06. The sweep comprised 16 steps of spatial frequency between 0.5 and 16.0 cpd, spaced evenly in the same linear transform of the log-log space as the radial CSF sweeps. For this task, the five targets presented were all separate instances of the same sweep, allowing five repeated measurements of the LCA threshold to be collected within one trial.

Conventional staircase task: Six observers (five with refractive error) also had their CSFs assessed using a conventional four-alternative forced-choice staircase task. Eight of the 15 radial sweeps used in the Gradiate task were measured, with every second Gradiate sweep left out. Stimuli were generated and progressed in the same way as Gradiate. In each trial, a filtered noise patch appeared just upward, rightward, downward, or leftward of a central black fixation point on the same mid-gray background as Gradiate. Each noise patch was again 6° in diameter and, to better emulate Gradiate's effects of motion on sensitivity, scrolled within its fixed envelope at 5° per second. Scrolling direction was randomly set to leftward or rightward in each trial. Observers indicated their best guess of the target's position by pressing the corresponding arrow on the keyboard. If their response was correct, a green dot flashed in the center of the screen, and that sweep was progressed by 0.05 normalized units outward along that radial trajectory in log-log CSF space, which determined its spatial frequency and contrast on its next appearance (i.e., became harder to see). If their response was incorrect, a red dot flashed, and that sweep was regressed by 0.05 units inward (i.e., became easier to see). All eight sweeps were randomly interleaved and, as in Gradiate, began at a common origin point with a spatial frequency of 1 cpd and RMS contrast ratio of 0.2. Each sweep continued until five reversals had occurred, and the final threshold of that sweep was computed by taking the four midpoints (in log-log space) between each pair of consecutive reversals, discarding the lowest and highest estimates, and averaging the remaining two. The eye tracker was used to pause the task before each trial until the observer returned to the central fixation point (with a tolerance radius of 2°). Observers were given a break after every 100 trials.

Procedure: A single experimental session comprised a calibration step using the standard Tobii Eye Tracking software suite, two repeats of a complete 15-point CSF measurement with Gradiate, and one trial (containing five repeated measurements) of the LCA variant of Gradiate. Each repeat of the complete CSF measurement was conducted by randomly dividing the 15 sweeps into three subsets of 5 sweeps, with those 5 sweeps being presented simultaneously. A random selection of background music was played during the task. Whenever a stimulus was advanced by the observer's eye movements, a musical note was played as helpful feedback for the observer. All audio was controlled using the Audiomath sound toolbox for Python (Hill, Mooney, & Prusky, 2020). When all three sweep sets were completed, the screen showed how many notes had been played. The LCA trial had the same feedback features and was conducted between the two repeats of the full CSF. Finally, Log MAR acuity was measured using a Tumbling "E" eye chart at a viewing distance of 620 mm. In total, a full experimental session took observers approximately 5 min. Observers completed two such sessions on different days or on the same day after a break and were instructed to follow each ball with their eyes until they could no longer see it. All observers with refractive correction completed two additional sessions without their eyewear on the same or different day. Six observers returned at a later date to complete the conventional 4AFC staircase task as described above. Five of those observers required refractive correction and completed sessions with and without their glasses on the same day.

Results

Observers were able to push the stimulus parameters up to their allowable limits on only 10 sweeps out of a total of 5,880 (0.17%) in the main CSF measurement task. These occurred on one of the three rightmost sweep vectors and no more than once per observer. For consistency, thresholds for these sweeps were computed as one half-step beyond the final point. Only 22 sweeps had no successes at all, most likely from momentary distraction, and were excluded from the computation of within-session means. None of the 490 LCA sweeps reached the highest possible spatial frequency or had no successes. There was a small but significant correlation between sweep success count and the order in which sweeps were initially tracked (from first to fifth) within each of the 1,176 total trials, $r=0.107$, $p<0.001$. Upon closer examination, this effect was driven entirely by a small deficit in mean success count for the first sweep tracked (7.67 stimuli as opposed to 8.47, 8.41, 8.37, and 8.36 stimuli for the second through fifth sweeps). The correlation is not significant when the first sweep is excluded ($r=-0.02$, $p=0.063$). It is not clear why the first sweep to be tracked exhibited this slight deficit, but as there was no correlation between sweep tracking order and sweep angle ($r=0.001$, $p=0.94$), it is unlikely to have biased the thresholds. The average time taken to complete a 15-point CSF was 2 min and 14 s with a standard deviation of 22.6 s.

Figure 20:
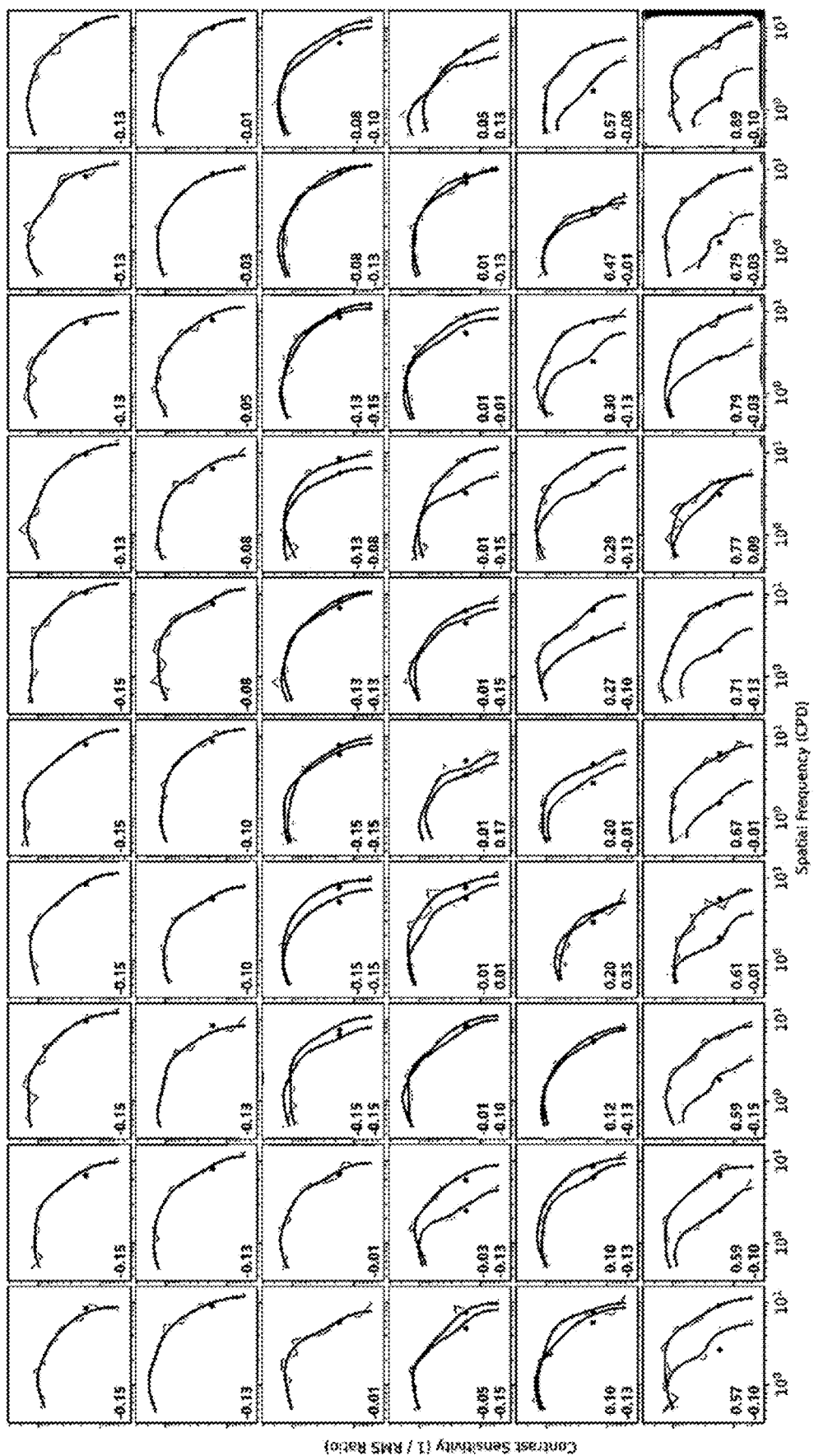
FIG. 20 CSFs for all observers. Normal or corrected-to-normal CSFs are depicted in blue, and impaired uncorrected CSFs are in red. The darker lines show the smoothed functions, and the numbers in each plot indicate normal (blue) and impaired (red) Log MAR acuity. The background of each plot becomes darker as impaired acuity gets worse. The singular blue (normal) and red (impaired) dots in each panel of FIG. 3 represent the LCA thresholds estimated with horizontal sweeps at an RMS contrast ratio of 0.06, averaged over all 10 repeats of that sweep for each correction type. Observers are sorted from top-left to bottom-right first by their need for corrective lenses and second by either their normal or (where applicable) impaired eye-chart acuity.

FIG. 20 depicts the CSFs for each observer averaged over all four repeats of Gradiate's 15-point measurement. Blue lines represent CSFs from observers with normal or corrected-to-normal vision, and red lines represent uncorrected CSFs from observers who wear corrective lenses. For simplicity, these two conditions will be referred to hereafter as "normal vision" (blue) and "impaired vision" (red), although not all observers who use refractive correction exhibit impaired CSFs at a 620-mm viewing distance. The lighter lines connect the raw thresholds and the darker lines show the same data smoothed with a Hann window. The red and blue numbers in the bottom left of each plot indicate impaired and normal Log MAR eye chart acuity, respectively.

Figure 21:
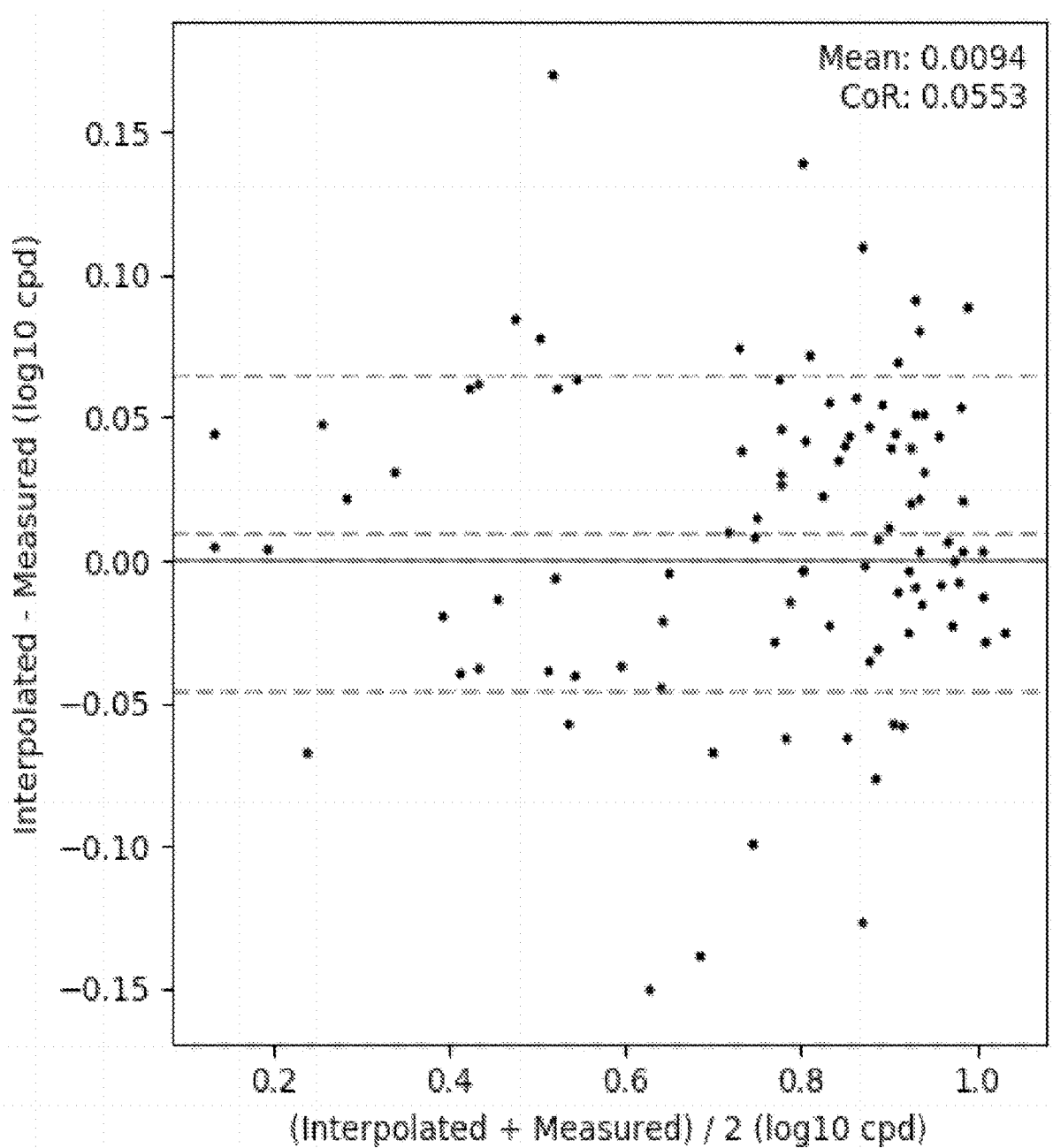
FIG. 21 Bland-Altman plot comparing all samples of measured LCA and interpolated LCA. The mean of these measures is shown on the horizontal axis and their difference (interpolated minus measured) on the vertical axis, both in log 10 cpd units of spatial frequency. The mean difference and CoR are shown in log 10 cpd in the top-right corner. The mean difference and 95% confidence interval are shown by the gray and red dotted lines, respectively, and the solid black line represents a difference of zero.

To allow straightforward comparisons across observers and conditions, all CSF analysis was conducted in the space of radial sweep lengths, which are values between 0 and 1 computed from the progress made along each sweep (as n−1/15, where n is the number of successfully tracked stimuli in that sweep). These "polar coordinates" of the CSF were reliable across the two separate experimental sessions conducted for each observer, with a Bland-Altman coefficient of repeatability (CoR) of 0.0562. FIG. 21 depicts a Bland-Altman comparison of the measured LCA thresholds (horizontal sweeps) with estimates computed by linearly interpolating the unsmoothed Gradiate CSF measured for that observer and correction (i.e., the point where each horizontal LCA sweep would intersect each smoothed curve in FIG. 3). The CoR was 0.055 log 10 cpd, which is almost identical to the CoR of the CSF sweeps and less than 5% of the log 10 interval between successive spatial frequency values in the LCA task (1.281). This indicates that the two measures were in close agreement, as can be seen directly in FIG. 20.

Gradiate Factor Analyses

We performed two factor analyses to identify variables that account for the variance in all CSFs: one analysis of the raw (not smoothed) sweep lengths and one analysis after normalizing the mean sweep length of each CSF to the grand mean (0.528). The second analysis was conducted to identify factors that account for variation in CSF shape rather than size. All mean sweep lengths from the normal and impaired CSFs of all observers were included in both analyses for a total of 98 CSFs. Factors were identified using the principal component method and an orthogonal equamax rotation. Two factors with an eigenvalue greater than 1 were retained in each analysis. The factor loadings on all 15 sweeps are shown in the top row of FIG. 5 and are immediately interpretable. In the raw analysis (left), Factor 1 explained variance in overall CSF radius (79.35%), weighted more heavily toward the high-spatial-frequency end of the curve, while Factor 2 explained some remaining variance (9.49%) in CSF radius at the low-spatial-frequency end. Notably, Factor 1 was highly correlated with both peak contrast sensitivity ($r=0.833$) and peak spatial frequency ($r=0.978$). Factor 2, however, was moderately correlated with peak contrast sensitivity ($r=0.519$) but only weakly and negatively correlated with peak spatial frequency ($r=-0.127$, all $p<0.001$). Both factors explained 96.4% of the variance in peak contrast sensitivity and 97.3% of the variance in peak spatial frequency when combined in linear regression models. We labeled these factors as "CSF radius" and "CSF slope," respectively. Note the results of this factor analysis do not substantially change if the impaired curves are excluded from the analysis, indicating that the same underlying factors account for variation in CSFs among observers with normal or corrected-to-normal refraction. Similarly, performing the same factor analysis on the smoothed CSFs yielded nearly identical results, except that the two factors instead account for a total of 97.56% of the variance in the smoothed sweep lengths. In the normalized analysis (right), Factor 1 explained 55.41% of the total variance and can be interpreted as the "aspect ratio" of the CSF. Higher scores on this factor indicate a greater width-to-height ratio in the CSF; conversely, lower scores indicate a smaller width-to-height ratio, as is the case for CSFs that drop off rapidly from their peak sensitivity. Predictably, this factor was significantly correlated with both CSF radius ($r=0.828$) and slope ($r=-0.532$) from the raw analysis, both $p<0.001$. Factor 2 accounted for 10.84% of the variance and can be interpreted as the "curvature" of the CSF. Higher scores on this factor indicate that the CSF has a greater radius along the central (more diagonal) sweeps relative to the low-end and high-end sweeps, while lower scores are typical of CSFs that peak earlier and are more buckled in the center. Curvature was correlated positively and moderately with both CSF radius ($r=0.321$) and slope ($r=0.291$), both $p<0.001$.

In the normalized analysis (right column), Factor 1 explained 55.41% of the total variance and can be interpreted as the "aspect ratio" of the CSF. Higher scores on this factor indicate a greater width-to-height ratio in the CSF; conversely, lower scores indicate a smaller width-to-height ratio, as is the case for CSFs that drop off rapidly from their peak sensitivity. Predictably, this factor was significantly correlated with both CSF radius ($r=0.828$) and slope ($r=-0.532$) from the raw analysis, both $p<0.001$. Factor 2 accounted for 10.84% of the variance and can be interpreted as the "curvature" of the CSF. Higher scores on this factor indicate that the CSF has a greater radius along the central (more diagonal) sweeps relative to the low-end and high-end sweeps, while lower scores are typical of CSFs that peak earlier and are more buckled in the center. Curvature was correlated positively and moderately with both CSF radius ($r=0.321$) and slope ($r=0.291$), both $p<0.001$.

Figure 22:
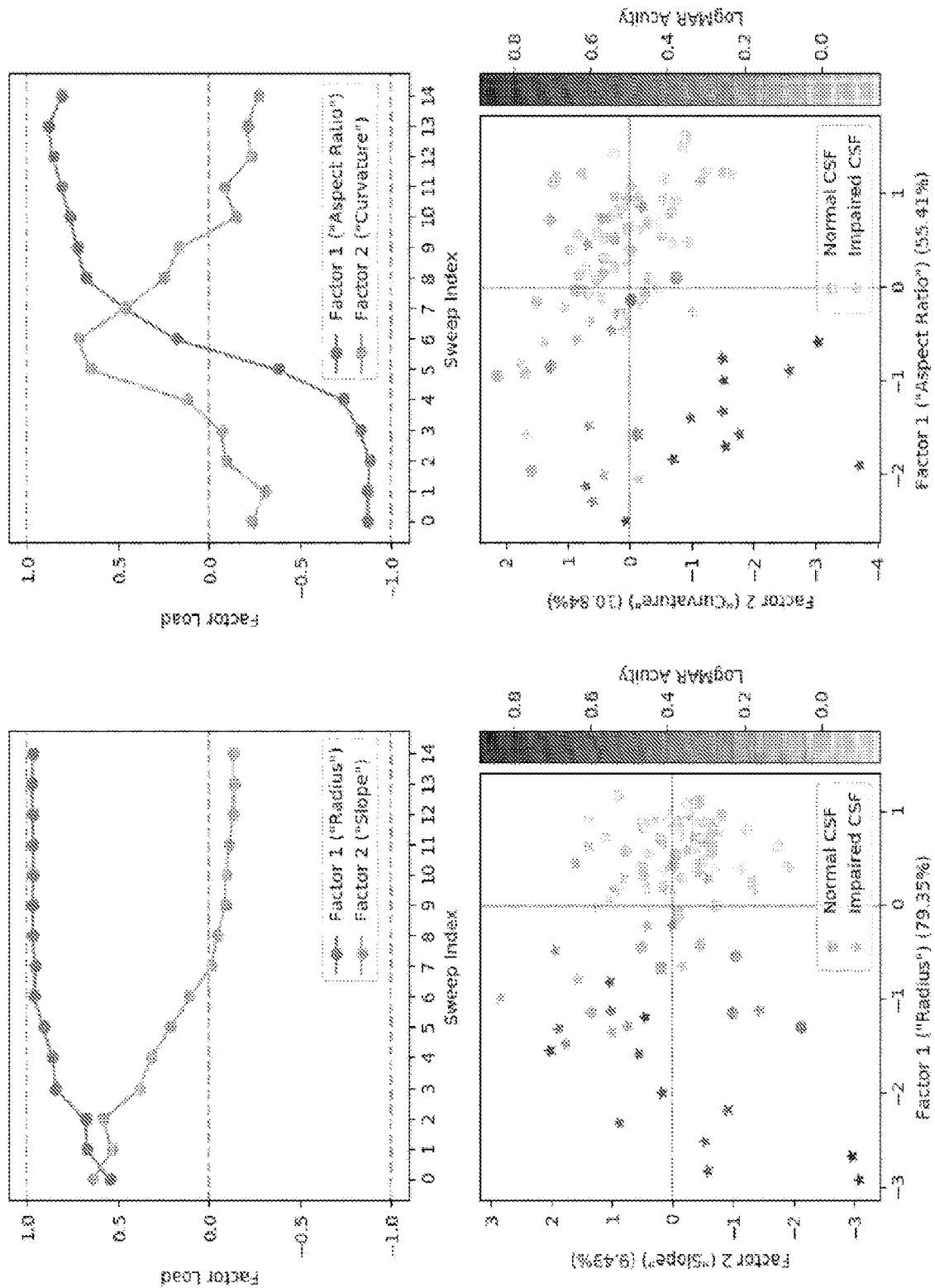
FIG. 22 Raw factor analysis (left column) and size-normalized factor analysis (right column) of overall CSF variance. Two factors were retained from each analysis. The plots in the top row depict the loadings of these factors on (i.e., correlations with) the 15 radial sweeps, indexed from 0 to 14. The plots in the bottom row depict the distributions of all CSFs in each two-factor space, with points colored by eye-chart acuity. In these plots, circles represent normal/corrected-to-normal CSFs and stars represent uncorrected CSFs.
Figure 23:
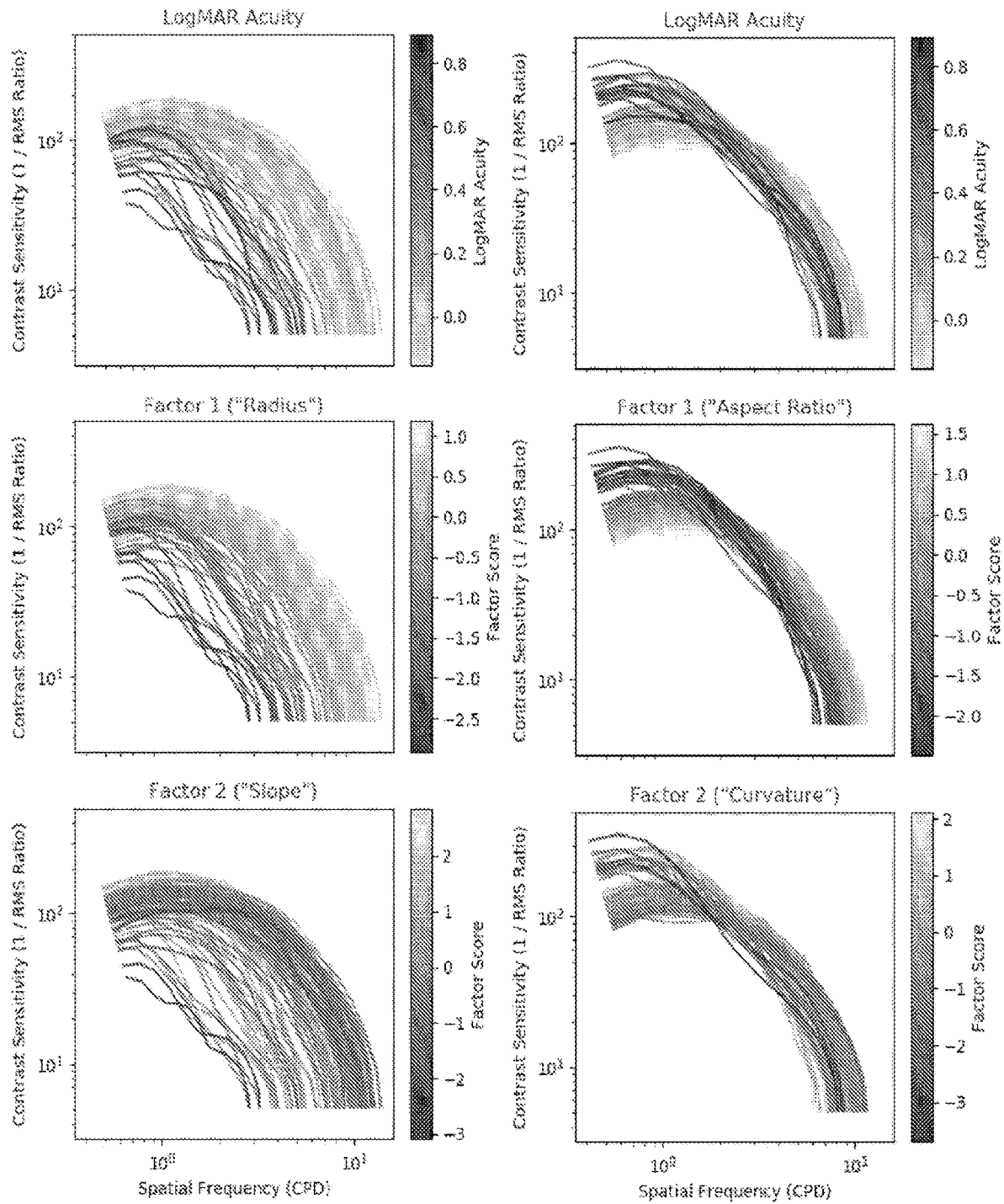
FIG. 23 Visualization of the relationship between the identified factors and CSFs. All CSFs from FIG. 20 (both normal and impaired) are superimposed in each panel and have additionally had their mean sweep length normalized in the right column. In the top row, the CSFs are colored by acuity, as in the bottom row of FIG. 22. In the middle and bottom columns, the CSFs are colored by the first and second factors of the raw (left column) and normalized (right column) factor analyses.

The scatterplots in the bottom row of FIG. 22 reveal how each pair of factors (on the axes) relates to Log MAR eye chart acuity (point color). Each point represents a normal (circles) or impaired (stars) CSF. In the raw analysis (bottom left panel), almost all normal CSFs had positive radius scores. Impaired CSFs, however, were spread out over negative scores on the radius axis. In a linear regression, CSF radius accounted for 73.6% of the variance in Log MAR acuity ($r=-0.858$, $p<0.001$) among all 98 CSFs. CSF slope accounted for a mere additional 0.1% of variance when added to this regression model, as indicated by the absence of any apparent relationship between acuity and CSF slope in the scatterplot. The scatterplot for the normalized analysis (bottom right panel) resembles the raw analysis but is rotated in this factor space, indicating that better acuity scores are predicted by both greater CSF aspect ratio and greater curvature. Together, the two orthogonal shape factors account for 67.0% of the variance in Log MAR acuity ($r=0.818$, $p<0.001$), which is only 6.6% less than the variance explained by CSF radius in our previous factor analysis. CSF radius, aspect ratio, and curvature together account for 77.8% of the variance in acuity when combined in one linear model ($r=0.882$, $p<0.001$), which is 4.2% more than radius alone. FIG. 23 provides a visualization for how the raw (left column) and normalized (right column) CSFs relate to Log MAR acuity and their two-factor models, which are used to color the curves in each of the three rows.

Figure 24:
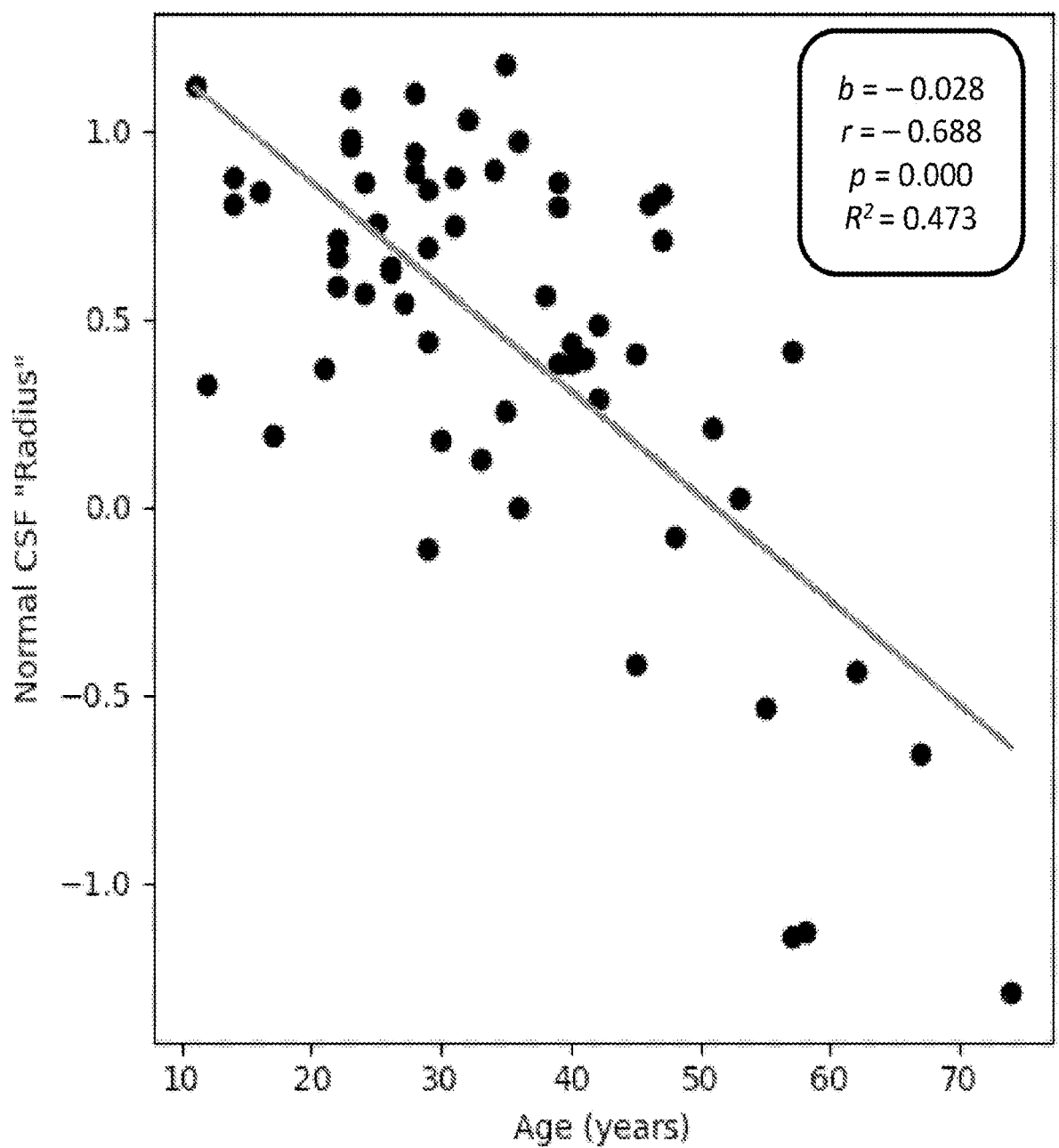
FIG. 24 Plot of CSF "radius" score (vertical axis) against observer age in years (horizontal axis) for normal and corrected-to-normal CSFs only. The regression statistics are shown in the top-right and the line of best fit depicted in red.

Finally, we examined the relationship between observer age and the two pairs of CSF components identified above by inspecting which combinations of factors best predicted age. CSF radius accounted for 47.3% of the variance in age across the 60 mean normal CSFs ($r=-0.688$, $p<0.001$), as shown in the linear regression plot in FIG. 24. CSF aspect ratio accounted for 26.6% of variance in age on its own ($r=-0.516$, $p<0.001$) but only an additional 0.5% of variance when combined with radius. Neither CSF slope nor curvature were significantly correlated with age. When CSF radius was regressed upon both age and corrected-to-normal acuity, rather than age alone, the regression coefficient of age as a predictor of CSF radius decreased from −0.028 radius score change per year of age to −0.019 (still $p<0.001$), indicating that the relationship between CSF radius and age was only partially mediated by acuity.

Saccadic & Other Tracking

In embodiments, the described method or system can be employed on or combined with Curveball and/or Gradiate methods/systems as described herein.

Arbitrary visual stimuli may be presented to an observer on a display. An eye tracker can be mounted to the display, the observer's head, or an intermediate stand. An algorithm continuously (e.g., at the same rate as the display refresh rate) monitors the participant's gaze response to all active stimuli and, in response to specific patterns of gaze input and stimulus attributes, may update the evidence-of-visibility score and/or evidence-of-trackability score of any active stimulus. Multiple stimuli may be presented simultaneously, and one stimulus may be nested within another; in particular, all stimuli are nested within the display, which is a stimulus in its entirety. These scores may be used to control future stimulus behavior, trigger audio events, or determine when the experience should end. A measure of gaze data reliability is also maintained, which indicates potential problems with the eye tracker, the observer's position, or their head pose.

The patterns of gaze input that are used to update these scores may include fixations, saccades, smooth pursuits, target tracking, optokinetic nystagmus, and/or blinks. Other arbitrary patterns may also be used, such as predictable noise patterns specific to a particular eye tracker model that decrease the current estimate of gaze data reliability. When the algorithm detects that the participant is not in front of the display, or detects that the participant's distance is too close to or too far away from the display, the task may be paused automatically until the participant is in front of the display within a permitted distance range (e.g., 400 to 800 millimeters). The permitted distance range may have a minimum distance range of 200 to 599 millimeters, and a maximum distance range of 601 to 900 mm.

The algorithms used to detect and classify different types of gaze responses may vary; some example algorithms are described below. Different algorithms, for example, may be required for different eye tracking hardware used in different embodiments of the invention. The statistics employed by these algorithms may be computed continuously while practicing the present invention and used for analytic and feedback purposes other than the exemplary classifications described herein. Different eye movement types may also have different effects on the evidence and reliability scores, according to the psychological research that underpins their relationship to visibility and trackability.

One way of detecting fixation events is by analyzing the two-dimensional dispersion metric of the x/y gaze coordinates over a sliding time window of gaze samples (e.g., 0.15 seconds) each time a new gaze sample arrives. The sliding time window of gaze samples may have a range of 0.03 seconds to 1 second. Gaze samples may be classified as part of an ongoing fixation event when the mean dispersion over this time window falls below a certain threshold. The mean position of the fixation event may be compared to the position of one or more active stimuli to determine which of those stimuli may be fixated ("target fixation").

```
dispersion = hypot(mean(get_gaze_dx( )), mean(get_gaze_dy( ))
if dispersion <= max_fixation_dispersion:
    FIXATION_ACTIVE = True
elif FIXATION_ACTIVE:
    FIXATION_ACTIVE = False
```

One way of detecting saccade events is by analyzing gaze velocity over a sliding time window of gaze samples (e.g., 0.15 seconds) each time a new gaze sample arrives. The sliding time window of gaze samples may have a range of 0.03 seconds to 1 second. Saccades may start when the magnitude of this velocity rises above a certain "start" threshold (e.g., 50 degrees per second) and persist through future gaze samples as long as the magnitude remains above a certain "end" threshold, which may differ from the start threshold (e.g., 30 degrees per second). The "start" threshold may have a range of 10 degrees per second to 70 degrees per second. The "end" threshold may have a range of 10 degrees per second to 70 degrees. False positives of this algorithm may be detected by additionally restricting the change in velocity direction from sample to sample below a certain angle (e.g., 90 degrees) after a saccade has started, ignoring saccades that return to a previous location, and/or ignoring detected saccades with a duration below a certain threshold (e.g., 10 milliseconds). The threshold angle may range from 45 degrees to 135 degrees. The threshold time duration may range from 1 millisecond to 20 milliseconds.

```
if min_saccade_speed <= get_gaze_speed( ) <= max_saccade_speed:
    if get_gaze_point( ) in get_previous_saccade_path( ):
        SACCADE_ACTIVE = False
    elif get_gaze_angle_change( ) > max_saccade_angle_change:
        SACCADE_ACTIVE = False
    else:
        SACCADE_ACTIVE = True
else:
    SACCADE_ACTIVE = False
```

One way of detecting smooth pursuit events is by analyzing gaze velocity and acceleration over a sliding time window of gaze samples (e.g., 0.15 seconds) each time a new gaze sample arrives. The sliding time window of gaze samples may have a range of 0.03 seconds to 1 second. Smooth pursuits may start when the magnitude of gaze velocity falls between certain minimum and maximum "start" thresholds (e.g., 5 degrees per second to 20 degrees per second) and the rate of change in the direction of gaze velocity is less than a certain angular value (e.g., 180 degrees per second), and persists as long as gaze velocity continues to fall within these thresholds. The minimum "start" threshold may range from 2 degrees per second to 10 degrees per second. The maximum "start" threshold may range from 15 degrees per second to 100 degrees per second. The threshold angular value may range from 90 degrees per second to 360 degrees per second.

```
if min_pursuit_speed <= get_gaze_speed( ) <= max_pursuit_speed:
    if get_gaze_angle_change( ) > max_pursuit_angle_change:
        PURSUIT_ACTIVE = False
    elif hypot(get_gaze_dx( ), get_gaze_dy( )) >= max_pursuit_delta:
        PURSUIT_ACTIVE = False
    else:
        PURSUIT_ACTIVE = True
else:
    PURSUIT_ACTIVE = False
```

One way of detecting target tracking events is by analyzing gaze position over a sliding time window of gaze samples (e.g., 0.15 seconds) each time a new gaze sample arrives and comparing it to the position of a given target over the same time window. The sliding time window of gaze samples may have a range of 0.03 seconds to 1 second. The algorithm may report that the participant is tracking that target if a sufficient proportion of gaze samples within that time window (e.g., at least 90%) fall within a certain distance of the position of the target at the same moment (e.g., 0.4 degrees of visual arc). The threshold proportion of gaze samples within the time window may range from 50% to 100%. The threshold distance of the position of the target may range from 0.1 degrees to 2.0 degrees. The coordinates of the target to which gaze position is compared may be its absolute position on the display or may first be corrected by subtracting the current gaze position from each target position sample so that any systematic offset between the target trajectory and gaze trajectory is ignored (e.g., the participant may not be tracking the exact center of the target). Target tracking may need to persist for some number of contiguous samples (e.g., five samples) before it is confirmed as a true positive classification. The threshold number of contiguous samples may range from 1 sample to 60 samples.

```
hits = 0
misses = 0
for gaze_point, target_point in get_recent_gaze_and_target_points( ):
    if dist(gaze_point, target_point) <= max_position_distance:
        hits += 1
    else:
        misses += 1
if hits / (hits + misses) >= min_hit_proportion:
    POSITION_TRACKING_ACTIVE = True
else:
    POSITION_TRACKING_ACTIVE = False
hits = 0
misses = 0
gaze_adjust = get_target_point( ) - get_gaze_point( )
for gaze_point, target_point in get_recent_gaze_and_target_points( ):
    gaze_point += gaze_adjust
    if dist(gaze_point, target_point) <= max_position_distance:
        hits += 1
    else:
        misses += 1
if hits / (hits + misses) >= min_hit_proportion:
    TRAJECTORY_TRACKING_ACTIVE = True
else:
    TRAJECTORY_TRACKING_ACTIVE = False
```

Target tracking events may alternatively be detected by monitoring "targeted" saccade eye movements. A targeted saccade may be classified as a saccade that starts within some distance of the target (e.g., four degrees of visual arc) and ends within some smaller distance of the target (e.g., three degrees of visual arc). The starting distance of the target may range from 1 degree of visual arc to 15 degrees of visual arc. The smaller end distance of the target may range from 1 degree of visual arc to 10 degrees of visual arc. Target tracking may be inferred when targeted saccades occur with sufficient frequency (e.g., twice per second) for a sufficiently long duration (e.g., two seconds) without any non-targeted saccades. The threshold frequency of targeted saccade occurrence without any non-targeted saccades may range from once per second to 4 times per second. The threshold time duration of the frequency of targeted saccade occurrences without any non-targeted saccades may range from 1 second to 3 seconds. Saccade-based target tracking may need to persist for some number of contiguous samples (e.g., five samples) before it is confirmed as a true positive classification. The threshold number of contiguous samples may range from 1 sample to 60 samples.

```
for second in get_time_frames(seconds):
    saccades = get_saccades_in_time_frame(second)
    if saccades.count( ) < min_saccade_frequency:
        SACCADE_TRACKING_ACTIVE = False
        return
    for saccade in saccades:
        start_distance = dist(get_target_point( ), saccade.start( ))
        end_distance = dist(get_target_point( ), saccade.end( ))
        if start_distance <= end_distance:
            SACCADE_TRACKING_ACTIVE = False
            return
SACCADE_TRACKING_ACTIVE = True
return
```

Optokinetic nystagmus events may be detected in a similar way to target tracking, but the trajectory of the participant's gaze may be required to be linear and interspersed with saccades whose velocity is in the opposite direction to the trajectory.

Blinks may be detected using an algorithm that varies with the exact eye tracker hardware used during the application of the method, as different eye trackers may produce different "signature" responses to blinks. For example, blinks may be classified by detecting periods in which no gaze data is reported by the eye tracker for no longer than a predetermined time (e.g., two seconds). Gaze samples immediately before and/or immediately after the detected blink (e.g., up to 0.5 seconds on each side) may be ignored to avoid the risk of using malformed gaze data during the blink. The threshold time for ignoring gaze samples immediately before and/or immediately after the detected blink may range from 0.25 seconds to 1 second, respectively.

In embodiments, target tracking events may be detected by monitoring "targeted" saccade eye movements. A targeted saccade, in embodiments, may be classified as a saccade that starts and ends within a predetermined distance and/or range of distance(s) from the target (e.g., five degrees of visual arc). For example, a targeted saccade may be classified as a saccade which starts within a first predetermined distance of the target (e.g. four degrees of visual arc) and ends within a second predetermined distance (which may be a smaller distance than the first predetermined distance (e.g. three degrees of visual arc)). The starting predetermined distance of the target may range from 1 degree of visual arc to 15 degrees of visual arc. The smaller ending predetermined distance of the target may range from 1 degree of visual arc to 10 degrees of visual arc. In embodiments, target tracking may be determined when, for example, targeted saccades occur at and/or above a predetermined frequency (e.g., once per second). The predetermined frequency of targeted saccade occurrence may range from once per second to 4 times per second. In embodiments, target tracking may be determined, as another example, when targeted saccades occur with sufficient frequency (e.g. twice per second) for a sufficiently long duration (e.g. two seconds). The threshold frequency of targeted saccade occurrence may range from once per second to 4 times per second. The threshold time duration of the frequency of targeted saccade occurrences may range from 1 second to 3 seconds. In embodiments, target tracking may be determined, as another example, when targeted saccades occur with sufficient frequency (e.g. three occurrences per second) for a sufficiently long duration (e.g. 1 second) without any non-targeted saccades. The threshold frequency of targeted saccade occurrence without any non-targeted saccades may range from once per second to 4 times per second. The threshold time duration of the frequency of targeted saccade occurrences without any non-targeted saccades may range from 1 second to 3 seconds. In embodiments, target tracking may be determined based on one or more of the following: the amount of occurrences of targeted saccades; the frequency of occurrences of one or more targeted saccades; the duration of occurrences of one or more targeted saccades; the occurrence of non-targeted saccades. Saccade-based target tracking, in embodiments, may be repeated one or more times. In embodiments, confirmation of a true positive classification may require more than one saccade-based target tracking sample. For example, saccade-based target tracking may need to persist for a predetermined number of contiguous samples (e.g. five samples) before a determination of a confirmed true positive classification can be made. The predetermined number of contiguous samples may range from 1 sample to 60 samples.

In embodiments, a system for dynamically assessing a visual function of a subject is provided, comprising: i) a visual display; ii) an eye-tracking device configured to detect a gaze position of at least one eye of the subject; iii) one or more processors operably connected to the visual display and the eye-tracking device; iv) a non-transitory memory operably connected to the one or more processors and including machine executable code that when executed by the one or more processors performs the steps of a) presenting for a first defined amount of time a first stimulus at a first location on the visual display; b) storing first stimulus information associated with the first stimulus, the first stimulus information including: i. first stimulus location information associated with a location of the first stimulus on the visual display for the first predetermined amount of time; and ii. first stimulus time stamp information associated with the first stimulus location information; c) receiving in real time, from the eye-tracking device, for the predetermined amount of time, first tracking data comprising: i. first gaze point information associated with a first point on the visual display to which the eye is directed during the predetermined amount of time; ii. first position information associated with a 3D position of the eye over the predetermined amount of time; and iii. first gaze point time stamp information associated with the gaze point information and the position information; d) storing the first tracking data in the non-transitory memory associated with the first stimulus; e) determining, for the first stimulus, a dynamic evidence-of-visibility score and a dynamic evidence-of-trackability score based at least on the tracking data and the first stimulus information; f) storing in the non-transitory memory, associated with the first stimulus: i. the dynamic evidence-of-visibility score; and ii. the dynamic evidence-of-trackability score; analyzing the stored first tracking data to determine a presence of one or more of: i. fixation eye movement(s); ii. saccade eye movement(s); iii. smooth pursuit eye movement(s); and iv. blink(s); h) analyzing the first tracking data obtained via the eye-tracking device to identify for the eye, relative to the first stimulus: i. position-matched tracking eye movements; ii. trajectory-matched tracking eye movements; and iii. saccade-based tracking eye movements; i) updating, in real time, the dynamic evidence-of-visibility score and/or the evidence-of-trackability score associated with the first stimulus based on at least one of any eye movements detected in step g) and step h); and j) updating in real time the appearance of the first stimulus to provide a second stimulus based on at least one of the updated evidence-of-visibility score and the updated evidence-of-trackability score for the first visual stimulus.

In embodiments of the system, the performing step includes presenting in real time for the first defined period of time a second stimulus at a second location on the visual display.

In embodiments of the system, the first stimulus information comprises contrast, spatial frequency, color, and size.

In embodiments of the system, the first gaze point information indicates a position of the first point on the visual display to which the eye is directed in units of degrees of visual angle relative to the center of the visual display.

In embodiments of the system, the first gaze point information indicates a direction of the point on the visual display to which the eye is directed relative to the center of the visual display.

In embodiments of the system, the first position information indicates a distance between the eye and the visual display.

In embodiments of the system, the receiving in real time is effected at the device sampling frequency.

In embodiments of the system, the machine executable code, when executed by the one or more processors, performs the step of calibrating the eye-tracking device for the eye based on the gaze point information and the stimulus information associated with the first stimulus on the visual display.

In embodiments of the system, the calibrating step is repeated periodically.

In embodiments of the system, the calibrating step is repeated aperiodically.

In embodiments of the system, the dynamic evidence-of-visibility score indicates a percentage of likelihood that the first stimulus is visible to the eye.

In embodiments of the system, the dynamic evidence-of-trackability indicates a percentage of likelihood that the first stimulus is tracked by the eye.

In embodiments of the system, the analyzing step further comprises determining a mean gaze point value over a sliding time window during the first defined amount of time.

In embodiments of the system, the analyzing step further comprises determining a gaze point velocity, including a magnitude and angle, over the sliding time window during the first amount of time.

In embodiments of the system, saccade eye movement is determined when a magnitude of the gaze point velocity exceeds a second predetermined threshold and remains above the second predetermined threshold for a first threshold period of time.

In embodiments of the system, the analyzing step further comprises determining whether a change in the gaze velocity angle changes by more than 90 degrees between two successive time windows. In embodiments, the change in the gaze velocity angle may range from 45 degrees to 135 degrees.

In embodiments of the system, the analyzing step further comprises determining a gaze point velocity, including a magnitude and angle, and a gaze point acceleration over the sliding time window during the first predetermined amount of time, wherein smooth pursuit eye movement is determined when the magnitude of the gaze point velocity falls within a first predetermined range and a rate of change of the gaze point velocity angle is below a predetermined third threshold value.

In embodiments of the system, blink eye movement is identified when there is no gaze point information for a first period of time.

In embodiments of the system, the determining step includes accessing prior tracking information.

In embodiments of the system, the analyzing step h) includes comparing gaze position information over a sliding time window during the first predetermined amount of time to respective first stimulus location information associated with first stimulus time stamp information falling within the sliding time window, wherein position-matched tracking eye movements are identified when the gaze position is within a predetermined distance from the first stimulus location.

In embodiments of the system, the analyzing step includes comparing gaze position information over a sliding time window during the first predetermined amount of time to respective first stimulus location information associated with first stimulus time stamp information falling within the sliding time window, wherein trajectory matched tracking eye movements are identified when the distance between the first stimulus and the adjusted gaze point of the eye at each time stamp inside the sliding window is below a threshold determined by the properties of the stimulus, where the adjusted gaze point is obtained by subtracting the most recent deviation in position between the first stimulus and the gaze point of the eye obtained from the eye tracker.

In embodiments of the system, the analyzing step further comprises determining a gaze point velocity, including a magnitude and angle, over the sliding time window during the first predetermined amount of time.

In embodiments of the system, saccade-based tracking eye movement is determined when a magnitude of the gaze point velocity exceeds a third predetermined threshold and remains above the third predetermined threshold for a first threshold amount of time.

In embodiments of the system, saccade-based tracking eye movement is identified when saccade eye movement is identified at a predetermined rate and persists for a fourth predetermined period of time.

In embodiments of the system, the first predetermined rate is twice per second. In embodiments, the predetermined rate may have a range of once per second to 4 times per second.

In embodiments of the system, the fourth predetermined time is 2 seconds. In embodiments, the fourth predetermined time may have a range of 1 second to 3 seconds.

In embodiments of the system, the non-transitory memory operably connected to the one or more processors includes machine executable code that when executed by the one or more processors performs the steps of: k) receiving in real time, from the eye-tracking device, for the first predetermined amount of time, second tracking data comprising; i. second gaze point information associated with a second point on the visual display to which a second eye is directed during the predetermined amount of time; ii. second position information associated with a 3D position of the second eye over the predetermined amount of time; and iii. second gaze point time stamp information associated with the second gaze point information and the second position information; l) storing the second tracking data in the non-transitory memory associated with the first stimulus; m) storing in the non-transitory memory, associated with the first stimulus: i. the dynamic evidence-of-visibility score; and ii. the dynamic evidence-of-trackability score; n) analyzing the stored second tracking data to determine a presence of one or more of: i. fixation eye movement(s); ii. saccade eye movement(s); iii. smooth pursuit eye movement(s); iv. optokinetic nystagmus eye movement(s); and v. blink eye movement(s); o) analyzing the second tracking data obtained via the eye-tracking device so as to determine, relative to the first stimulus: i. position-matched tracking eye movements; ii. trajectory-matched tracking eye movements; and iii. saccade-based tracking eye movements; p) updating, in real time, the dynamic evidence-of-visibility score and/or the evidence-of-trackability score associated with the first stimulus based on at least one of any eye movements detected in step m) and step n); q) updating in real time the appearance of the first stimulus to provide the second stimulus based on at least one of the updated evidence-of-visibility score and the updated evidence-of-trackability score for the first visual stimulus.

In embodiments of the system, the second gaze point information indicates a position of the second point on the visual display to which the second eye is directed in terms of degrees of visual angle relative to a center of the visual display.

In embodiments of the system, the second gaze point information indicates a direction of the point on the visual display to which the second eye is directed relative to a center of the visual display.

In embodiments of the system, the second position information indicates a distance between the second eye and the visual display.

In embodiments of the system, the receiving in real time is effected at the device sampling frequency.

In embodiments of the system, the machine executable code, when executed by the one or more processors, performs the step of calibrating the eye-tracking device for the second eye based on the second gaze point information with regard to the stimulus information associated with the first stimulus on the visual display.

In embodiments of the system, the calibrating step is repeated periodically.

In embodiments of the system, the calibrating step is repeated aperiodically.

In embodiments of the system, the determining step d) includes determining, for the first stimulus, the dynamic evidence-of-visibility score and the dynamic evidence-of-trackability score based at least on the second tracking data and the first stimulus information.

In embodiments of the system, the dynamic evidence-of-visibility score indicates a percentage of likelihood that the first stimulus is visible to the at least one eye and the second eye.

In embodiments of the system, the analyzing step further comprises determining a mean gaze point value over a sliding time window during the second predetermined amount of time, wherein fixation movement is determined when the mean gaze value exceeds a first threshold.

In embodiments of the system, the analyzing step further comprises determining a gaze point velocity, including a magnitude and angle, over the sliding time window during the second amount of time.

In embodiments of the system, saccade eye movement is determined when a magnitude of the gaze point velocity exceeds the second predetermined threshold and remains above the second predetermined threshold for the first threshold period of time.

In embodiments of the system, the analyzing step further comprises determining whether a change in the gaze velocity angle changes by more than 90 degrees between two successive time windows. In embodiments, the change in the gaze velocity angle may range from 45 degrees to 135 degrees.

In embodiments of the system, the analyzing step further comprises determining a gaze point velocity, including a magnitude and angle, and a gaze point acceleration over the sliding time window during the second predetermined amount of time, wherein smooth pursuit eye movement is determined when the magnitude of the gaze point velocity falls within a first predetermined range and a rate of change of the gaze point velocity angle is below a predetermined third threshold value.

In embodiments of the system, the determining step includes accessing tracking information associated with a prior amount of time.

In embodiments of the system, the machine executable code, when executed by the one or more processors, may perform the steps for a second eye of the subject.

In embodiments of the system, the analyzing step o) includes comparing gaze position information over a sliding time window during the second predetermined amount of time to respective first stimulus location information associated with first stimulus time stamp information falling within the sliding time window, wherein position-matched tracking eye movements are identified when the gaze position is within a predetermined distance from the first stimulus location.

In embodiments of the system, the analyzing step includes comparing gaze position information over a sliding time window during the first predetermined amount of time to respective first stimulus location information associated with first stimulus time stamp information falling within the sliding time window, wherein trajectory matched tracking eye movements are identified when the distance between the first stimulus and the adjusted gaze point of the eye at each time stamp inside the sliding window is below a threshold determined by the properties of the stimulus, where the adjusted gaze point is obtained by subtracting the most recent deviation in position between the first stimulus and the gaze point of the eye obtained from the eye tracker.

In embodiments of the system, the analyzing step further comprises determining a gaze point velocity, including a magnitude and angle, over the sliding time window during the first predetermined amount of time.

In embodiments of the system, saccade-based tracking eye movement is determined when a magnitude of the gaze point velocity exceeds a third predetermined threshold and remains above the third predetermined threshold for a first threshold amount of time.

In embodiments of the system, saccade-based tracking eye movement is identified when saccade eye movement is identified at a predetermined rate and persists for a fourth predetermined period of time.

In embodiments of the system, the first predetermined rate is twice per second. In embodiments, the first predetermined rate may have a range of once per second to 4 times per second.

In embodiments of the system, the fourth predetermined time is 2 seconds. In embodiments, the fourth predetermined time may have a range of 1 second to 3 seconds.

In embodiments of the system, the second tracking data comprises a gaze point and three-dimensional eye data.

In embodiments of the system, the non-transitory memory operably connected to the one or more processors includes machine executable code that when executed by the one or more processors performs the steps of: k) presenting in real time for a second predetermined amount of time at least the second stimulus at a second location on the visual display; l) storing second stimulus information associated with the second stimulus, the second stimulus information including: i. second stimulus location information associated with the second location of the second stimulus on the visual display for the second predetermined amount of time; ii. second stimulus time stamp information associated with the second stimulus location information; m) receiving in real time, from the eye-tracking device, for the second predetermined amount of time, second tracking data comprising: i. second gaze point information associated with a second point on the visual display to which the at least one eye is directed during the second predetermined amount of time; ii. second position information associated with a 3D position of the at least one eye over the second predetermined amount of time; and iii. second gaze point time stamp information associated with the second gaze point information and the second position information; n) storing the second tracking data in the non-transitory memory associated with the first stimulus; o) determining, for the second stimulus, a second dynamic evidence-of-visibility score and a second dynamic evidence-of-trackability score based at least on the second tracking data and the second stimulus information; p) storing in the non-transitory memory, associated with the second stimulus: i. the second dynamic evidence-of-visibility score; and ii. the second dynamic evidence-of-trackability score; q) analyzing the stored second tracking data to determine a presence of one or more of: i. fixation eye movement(s); ii. saccade eye movement(s); iii. smooth pursuit eye movement(s); and iv. blink eye movement(s); r) analyzing the second tracking data obtained via the eye-tracking device so as to, for the at least one eye, relative to the second stimulus, determine: i. position-matched tracking eye movements; ii. trajectory-matched tracking eye movements; and iii. saccade-based tracking eye movements; s) updating, in real time, at least one of the second dynamic evidence-of-visibility score and the second evidence-of-trackability score associated with the second stimulus based on at least one of any eye movements detected in step q) and step r); and t) updating in real time the appearance of the second stimulus to provide a fifth stimulus based on at least one of the updated second evidence-of-visibility score and the updated second evidence-of-trackability score for the second stimulus.

In embodiments of the system, the second stimulus is the first stimulus.

In embodiments of the system, the second stimulus is different from the first stimulus.

In embodiments of the system, the presenting step includes presenting in real time for the second predetermined period of time a fourth stimulus at a fourth location on the visual display.

In embodiments of the system, the second stimulus location information is the same as the first stimulus location information.

In embodiments of the system, the second stimulus location information is different from the first stimulus location information.

In embodiments of the system, the second stimulus information comprises contrast, spatial frequency, color, and size.

In embodiments of the system, the second gaze point information indicates a position of the second point on the visual display to which the at least one eye is directed in terms of degrees of visual angle relative to a center of the visual display during the second predetermined amount of time.

In embodiments of the system, the second gaze point information indicates a direction of the second point on the visual display to which the at least one eye is directed relative to a center of the visual display during the second predetermined amount of time.

In embodiments of the system, the second position information indicates a distance between the at least one eye and the visual display during the second predetermined amount of time.

In embodiments of the system, the second dynamic evidence-of-visibility score indicates a percentage of likelihood that the second stimulus is visible to the at least one eye.

In embodiments of the system, the second dynamic evidence-of-trackability indicates a percentage of likelihood that the second stimulus is tracked by the at least one eye.

In embodiments of the system, the analyzing step further comprises determining a mean gaze point value over a sliding time window during the second predetermined amount of time, wherein fixation movement is determined when the mean gaze value exceeds a first threshold.

In embodiments of the system, the analyzing step further comprises determining a gaze point velocity, including a magnitude and angle, over the sliding time window during the second amount of time.

In embodiments of the system, saccade eye movement is determined when a magnitude of the gaze point velocity exceeds the second predetermined threshold and remains above the second predetermined threshold for the first threshold period of time.

In embodiments of the system, the analyzing step further comprises determining whether a change in the gaze velocity angle changes by more than 90 degrees between two successive time windows. In embodiments, the change in the gaze velocity angle may range from 45 degrees to 135 degrees.

In embodiments of the system, the analyzing step further comprises determining a gaze point velocity, including a magnitude and angle, and a gaze point acceleration over the sliding time window during the second predetermined amount of time, wherein smooth pursuit eye movement is determined when the magnitude of the gaze point velocity falls within a first predetermined range and a rate of change of the gaze point velocity angle is below a predetermined third threshold value.

In embodiments of the system, blink eye movement is identified when there is no gaze point information for a first period of time.

In embodiments of the system, the analyzing step r) includes comparing gaze position information over a sliding time window during the second predetermined amount of time to respective second stimulus location information associated with second stimulus time stamp information falling within the sliding time window, wherein position-matched tracking eye movements are identified when the gaze position is within a predetermined distance from the first stimulus location.

In embodiments of the system, the analyzing step includes comparing gaze position information over a sliding time window during the second predetermined amount of time to respective second stimulus location information associated with second stimulus time stamp information falling within the sliding time window, wherein trajectory matched tracking eye movements are identified when the distance between the second stimulus and the adjusted gaze point of the eye at each time stamp inside the sliding window is below a threshold determined by the properties of the stimulus, where the adjusted gaze point is obtained by subtracting the most recent deviation in position between the second stimulus and the gaze point of the eye obtained from the eye tracker.

In embodiments of the system, the analyzing step further comprises determining a gaze point velocity, including a magnitude and angle, over the sliding time window during the second predetermined amount of time.

In embodiments of the system, saccade eye movement is determined when a magnitude of the gaze point velocity exceeds a third predetermined threshold and remains above the third predetermined threshold for a first threshold amount of time.

In embodiments of the system, saccade-based tracking movement is identified when saccade eye movement is identified at a predetermined rate and persists for a fourth predetermined period of time.

In embodiments of the system, the first predetermined rate is twice per second. In embodiments, the predetermined rate may have a range of once per second to 4 times per second.

In embodiments of the system, the fourth predetermined time is 2 seconds. In embodiments, the fourth predetermined time may have a range of 1 second to 3 seconds.

In embodiments of the system, the machine executable code, when executed by the one or more processors, performs the step of updating in real time, for the at least one eye and the second eye, the calibration of the eye-tracking device based on the evidence-of-visibility score(s) or evidence-of-trackability score(s) of one or more visual stimuli.

In embodiments of the system, the machine executable code, when executed by the one or more processors, performs the step of presenting auditory or tactile stimuli to the subject based on the evidence-of-visibility score(s) or evidence-of-trackability score(s) of at least one or the at least one stimulus and the second stimulus.

In embodiments of the system, the machine executable code, when executed by the one or more processors, performs the step of determining, in real time, an estimate of the subject's attentiveness, fatigue level, and/or ability based on the evidence-of-visibility score(s) or evidence-of-trackability score(s).

In embodiments, a method for dynamically assessing a visual function of a subject is provided, comprising assessing the subject's visual function in one or both eyes of the subject in accordance with the system of any of the previously discussed embodiments.

Figure 25:
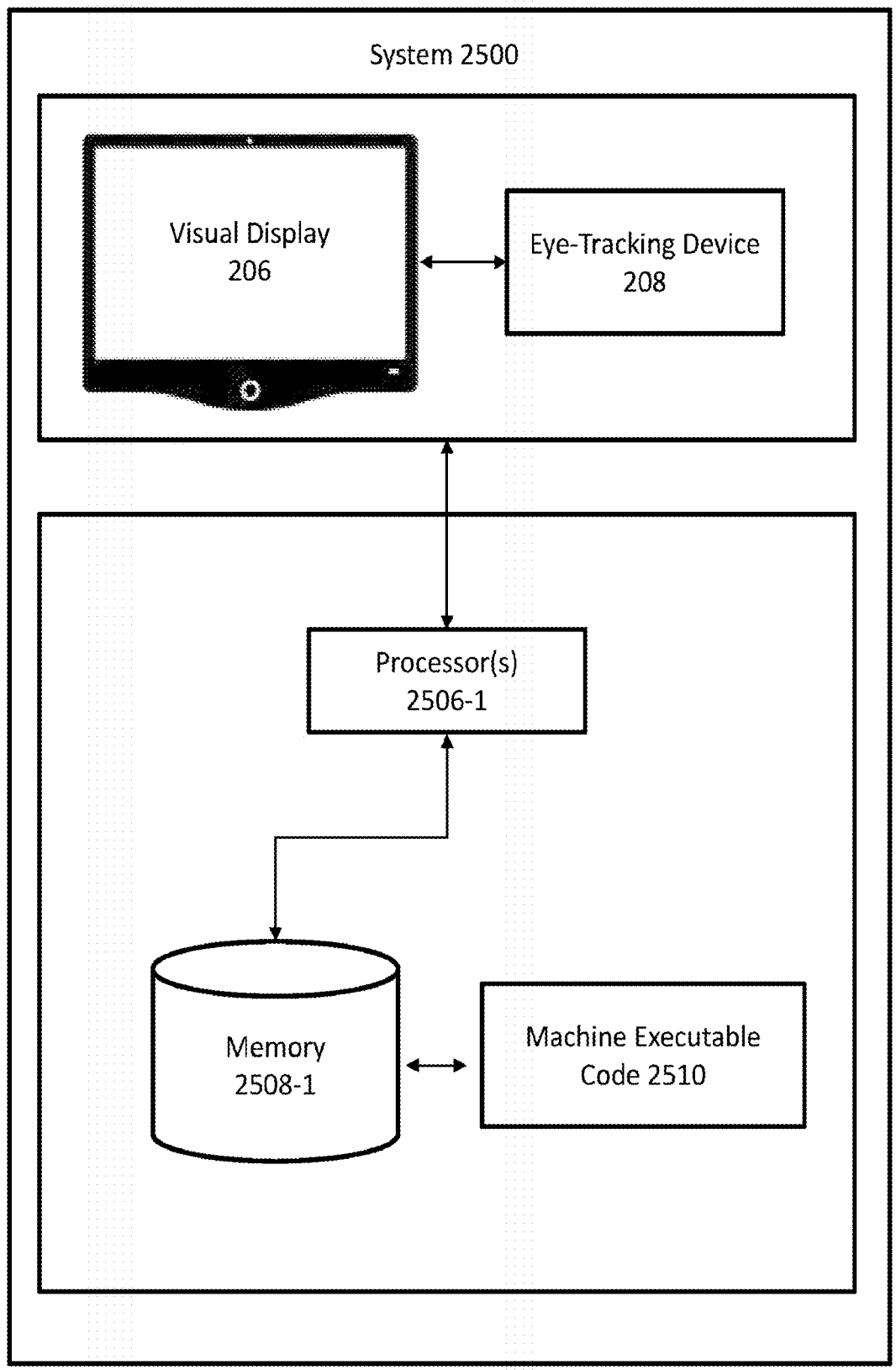
FIG. 25 is a schematic illustration of a system for evaluating contrast sensitivity and other visual metrics in accordance with embodiments of the present invention.
Figure 26:
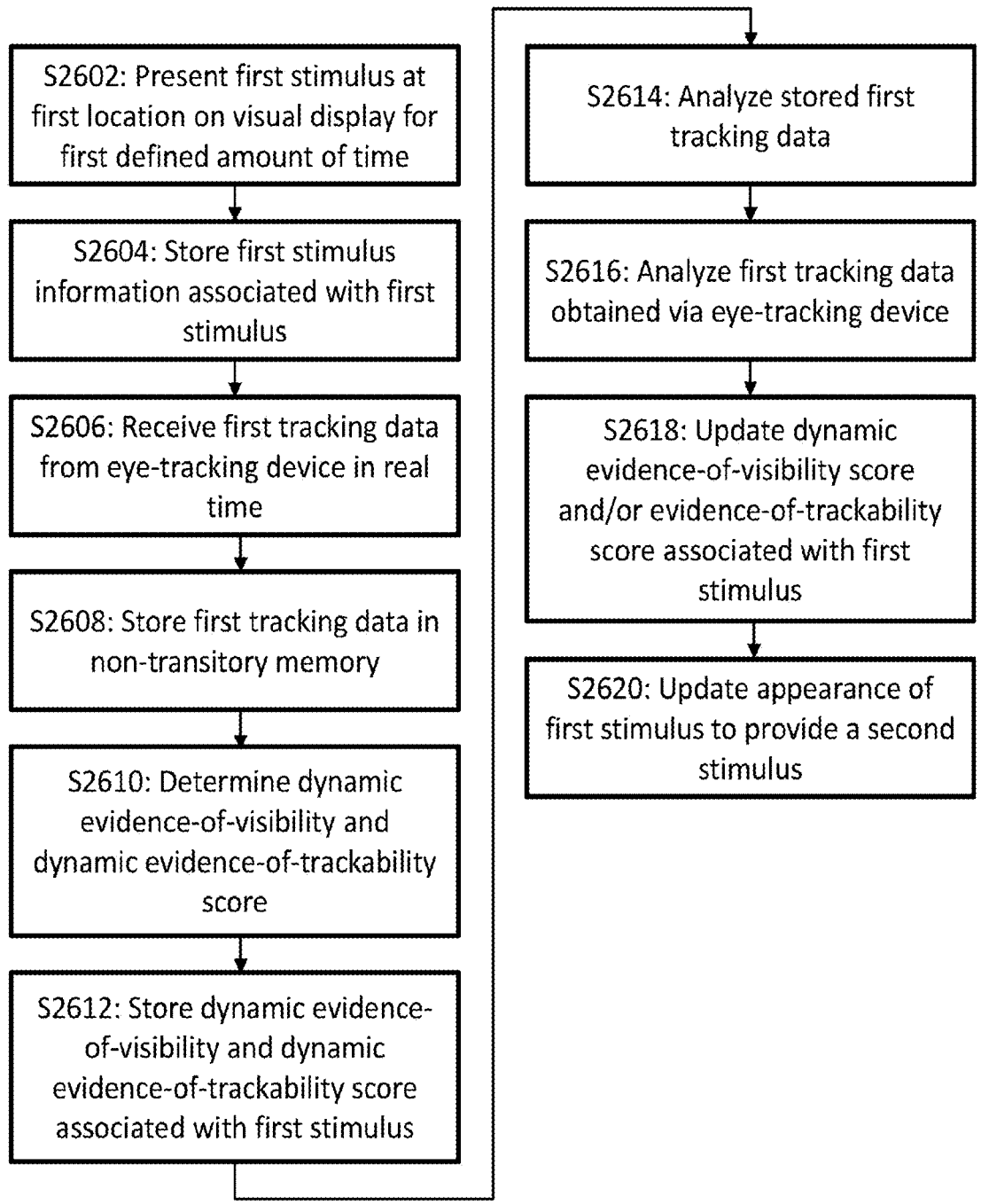
FIG. 26 is a schematic diagram of a process flow for evaluating contrast sensitivity and other visual metrics in accordance with embodiments of the present invention.

FIG. 25 is a schematic illustration of a system for evaluating contrast sensitivity and other visual metrics in accordance with embodiments of the present invention. FIG. 26 is a schematic diagram of a process flow for evaluating contrast sensitivity and other visual metrics in accordance with embodiments of the present invention. In embodiments, a system for dynamically assessing a visual function of a subject may include: i) a visual display 206; ii) an eye-tracking device 208 configured to detect a gaze position of at least one eye 210-1 of the subject 202; iii) one or more processors 2506-1 operably connected to the visual display 206 and the eye-tracking device 208; and iv) a non-transitory memory 2508-1 operably connected to the one or more processors 2506-1 and including machine executable code 2510.

In embodiments, the machine executable code 2510, when executed by the one or more processors 2506-1, may perform the step of a) presenting for a first defined amount of time a first stimulus 204-1 at a first location on the visual display 206 (S2602). In embodiments, the presenting step may include presenting in real time for the first defined period of time a second stimulus 204-2 at a second location on the visual display 206. In embodiments, the machine executable code 2510, when executed by the one or more processors 2506-1 may perform the step of b) storing first stimulus information associated with the first stimulus 204-1 (S2604). In embodiments, the first stimulus information may include: i) a first stimulus location information associated with a location of the first stimulus on the visual display 206 for the first predetermined amount of time; and ii) first stimulus time stamp information associated with the first stimulus location information. In embodiments, the first stimulus information may further include contrast, spatial frequency, color, and size.

In embodiments, the machine executable code 2510, when executed by the one or more processors 2506-1 may perform the step of c) receiving in real time, from the eye-tracking device 208, for the predetermined amount of time, first tracking data (S2606). In embodiments, the first tracking data may include: i) first gaze point information associated with a first point on the visual display 206 to which the eye 210-1 is directed during the predetermined amount of time; ii) first position information associated with a 3D position of the eye 210-1 over the predetermined amount of time; and iii) first gaze point time stamp information associated with the gaze point information and the position information. In embodiments, the first gaze point information may indicate a position of the first point on the visual display 206 to which the eye 210-1 is directed in units of degrees of visual angle relative to the center of the visual display 206. In embodiments, the first gaze point information may indicate a direction of the point on the visual display 206 to which the eye 210-1 is directed relative to the center of the visual display 206. In embodiments, the first gaze point information may indicate a distance between the eye 210-1 and the visual display 206. In embodiments, the receiving in real time may be effected at the device sampling frequency.

In embodiments, the machine executable code 2510, when executed by the one or more processors 2506-1, may perform the step of d) storing the first tracking data in the non-transitory memory 2508-1 associated with the first stimulus 204-1 (S2608). In embodiments, the machine executable code, when executed by the one or more processors 2506-1, may perform the step of calibrating the eye-tracking device 208 for the eye 210-1 based on the gaze point information and the stimulus information associated with the first stimulus 204-1 on the visual display 206. In embodiments, the calibrating step may be repeated periodically. In embodiments, the calibrating step may be repeated aperiodically.

In embodiments, the machine executable code 2510, when executed by the one or more processors 2506-1, may perform the step of e) determining, for the first stimulus 204-1, a dynamic evidence-of-visibility score and a dynamic evidence-of-trackability score based at least on the tracking data and the first stimulus information (S2610). In embodiments, the machine executable code 2510 for determining the dynamic evidence-of-visibility score and the dynamic evidence-of-trackability score may include:

```
trackability = a * position_pursuit_tracking +
b * trajectory_pursuit_tracking + c *
saccade_pursuit_tracking
# where a, b, and c are weight coefficients between 0 and 1
visibility = w * trackability + x * saccade_to_target –
y * saccade_away_from_target + z *
fixation_on_target
# where w, x, y, and z are weight coefficients between 0 and 1
TRACKABLE[stimulus] = trackability >= stimulus_trackability_threshold
VISIBLE[stimulus] = True = visibility >= stimulus_visibility_threshold
```

In embodiments, the dynamic evidence-of-visibility score may indicate a percentage of likelihood that the first stimulus 204-1 is visible to the eye 210-1. In embodiments, the dynamic evidence-of-trackability indicates a percentage of likelihood that the first stimulus 204-1 is tracked by the eye 210-1. In embodiments, the machine executable code 2510, when executed by the one or more processors 2506-1, may perform the step of f) storing in the non-transitory memory 2508-1 associated with the first stimulus 204-1: i) the dynamic evidence-of-visibility score; and ii) the dynamic evidence-of-trackability score (S2612).

In embodiments, the machine executable code 2510, when executed by the one or more processors 2506-1, may perform the step of g) analyzing the stored first tracking data to determine a presence of one or more of: fixation eye movement(s), saccade eye movement(s), smooth pursuit eye movement(s), and blink(s) (S2614). In embodiments, analyzing the stored first tracking data to determine a presence of fixation eye movement(s) may include:

```
dispersion = hypot(mean(get_gaze_dx( )), mean(get_gaze_dy( )))
if dispersion <= max_fixation_dispersion:
    FIXATION_ACTIVE = True
elif FIXATION_ACTIVE:
    FIXATION_ACTIVE = False
```

In embodiments, analyzing the stored first tracking data to determine a presence of saccade eye movement(s) may include:

```
if min_saccade_speed <= get_gaze_speed( ) <= max_saccade_speed:
    if get_gaze_point( ) in get_previous_saccade_path( ):
        SACCADE_ACTIVE = False
    elif get_gaze_angle_change( ) > max_saccade_angle_change:
        SACCADE_ACTIVE = False
    else:
        SACCADE_ACTIVE = True
else:
    SACCADE_ACTIVE = False
```

In embodiments, analyzing the stored first tracking data to determine a presence of smooth pursuit eye movement(s) may include:

```
if min_pursuit_speed <= get_gaze_speed( ) <= max_pursuit_speed:
    if get_gaze_angle_change( ) > max_pursuit_angle_change:
        PURSUIT_ACTIVE = False
    elif hypot(get_gaze_dx( ), get_gaze_dy( )) >= max_pursuit_delta:
        PURSUIT_ACTIVE = False
    else:
        PURSUIT_ACTIVE = True
else:
    PURSUIT_ACTIVE = False
```

In embodiments, the analyzing step may further include determining a mean gaze point value over a sliding time window during the first defined amount of time. In embodiments, the analyzing step may further include determining a gaze point velocity, including a magnitude and angle, over the sliding time window during the first amount of time. In embodiments, the first defined amount of time may be predetermined. In embodiments, the first defined amount of time may be dynamically determined dependent on the dynamic evidence-of-visibility and dynamic evidence-of-trackability score. In embodiments, the saccade eye movement may be determined when a magnitude of the gaze point velocity exceed a second predetermined threshold and remains above the second predetermined threshold and remains above the second predetermined threshold for a first threshold period of time. In embodiments, the analyzing step may further include determining whether a change in the gaze velocity angle changes by more than 90 degrees between two successive time windows. In embodiments, the change in the gaze velocity angle may range from 45 degrees to 135 degrees. In embodiments, the analyzing step may further include determining a gaze point velocity, including a magnitude and angle, and a gaze point acceleration over the sliding time window during the first predetermined amount of time, wherein smooth pursuit eye movement is determined when the magnitude of the gaze point velocity falls within a first predetermined range and a rate of change of the gaze point velocity angle is below a predetermined third threshold value. In embodiments, blink eye movement may be identified when there is no gaze point information for a first period of time. In embodiments, the determining step may include accessing prior tracking information.

In embodiments, the machine executable code 2510, when executed by the one or more processors 2506-1, may perform the step of h) analyzing the first tracking data obtained via the eye-tracking device 208 to identify for the eye 210-1, relative to the first stimulus 204-1, position-matched tracking eye movements, trajectory-matched tracking eye movements, and saccade-based tracking eye movements (S2616). In embodiments, the analyzing step h) may include comparing gaze position information over a sliding time window during the first predetermined amount of time to respective first stimulus location information associated with first stimulus time stamp information falling within the sliding time window, wherein position-matched tracking eye movements are identified when the gaze position is within a predetermined distance from the first stimulus location. In embodiments, the analyzing step may include comparing gaze position information over a sliding time window during the first predetermined amount of time to respective first stimulus location information associated with first stimulus time stamp information falling within the sliding time window, wherein trajectory matched tracking eye movements are identified when the distance between the first stimulus 204-1 and the adjusted gaze point of the eye at each time stamp inside the sliding window is below a threshold determined by the properties of the stimulus, where the adjusted gaze point is obtained by subtracting the most recent deviation in position between the first stimulus and the gaze point of the eye 210-1 obtained from the eye tracker 208. In embodiments, the analyzing step may further include determining a gaze point velocity, including a magnitude and angle, over the sliding time window during the first predetermined amount of time. In embodiments, saccade-based tracking eye movement may be determined when a magnitude of the gaze point velocity exceeds a third predetermined threshold and remains above the third predetermined threshold for a first threshold amount of time. In embodiments, saccade-based tracking eye movement may be identified when saccade eye movement is identified at a predetermined rate and persists for a fourth predetermined period of time. In embodiments, the first predetermined rate may be, for example, twice per second. In embodiments, the fourth predetermined time may be, for example, 2 seconds.

In embodiments, the machine executable code 2510, when executed by the one or more processors 2506-1, may perform the step of i) updating, in real time, the dynamic evidence-of-visibility score and/or the evidence-of-trackability score associated with the first stimulus 204-1 (S2618) based on at least one of any eye movements detected in step g) (S2614) and step h) (S2616). In embodiments, the machine executable code 2510, when executed by the one or more processors 2506-1, may perform the step of updating, in real time the appearance of the first stimulus 204-1 to provide a second stimulus 204-2 based on at least one of the updated evidence-of-visibility score and the updated evidence-of-trackability score for the first visual stimulus 204-1.

Figure 27:
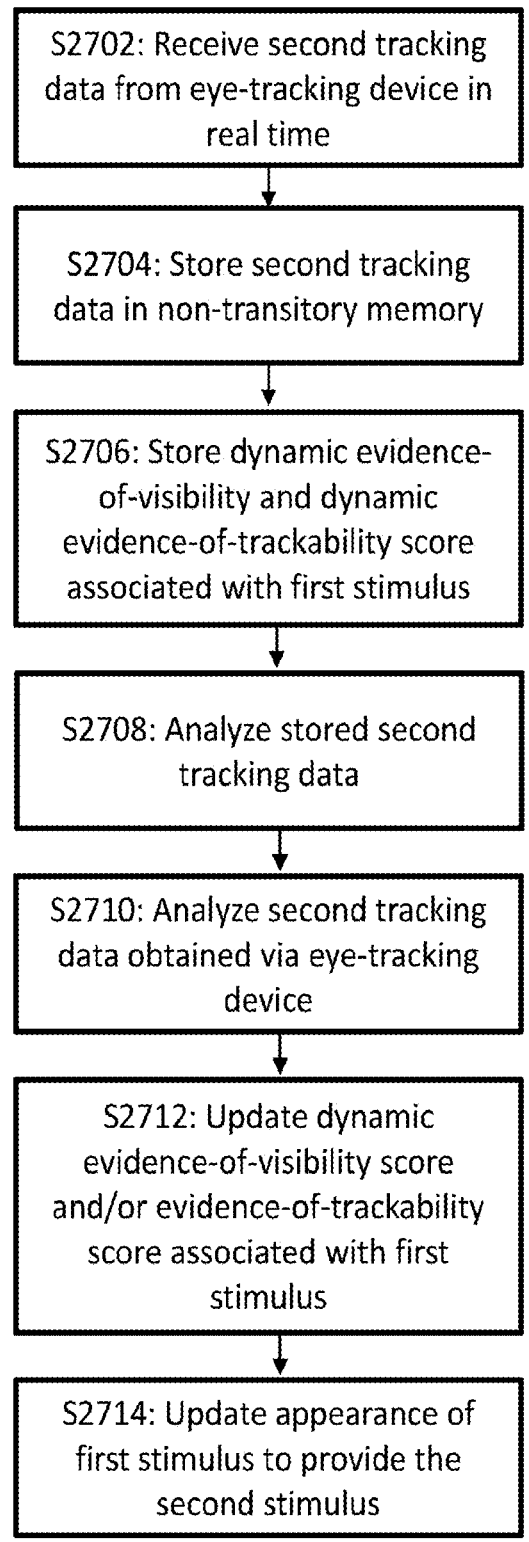
FIG. 27 is a schematic diagram of a process flow for evaluating contrast sensitivity and other visual metrics in accordance with another embodiment of the present invention.

FIG. 27 is a schematic diagram of a process flow for evaluating contrast sensitivity and other visual metrics in accordance with another embodiment of the present invention. In embodiments, the machine executable code 2510, when executed by the one or more processors 2506-1, may perform the step of k) receiving in real time, from the eye-tracking device 208, for the first predetermined amount of time, second tracking data (S2702). In embodiments, the second tracking data may include: i) second gaze point information associated with a second point on the visual display 206 to which a second eye 210-2 is directed during the predetermined amount of time; ii) second position information associated with a 3D position of the second eye 210-2 over the predetermined amount of time; and iii) second gaze point time stamp information associated with the second gaze point information and the second position information. In embodiments, the second gaze point information may indicate a position of the second point on the visual display 206 to which the second eye 210-2 is directed in terms of degrees of visual angle relative to the center of the visual display 206. In embodiments, the second gaze point information may indicate a direction of the point on the visual display 206 to which the second eye 210-2 is directed relative to a center of the visual display. In embodiments, the second position information may indicate a distance between the second eye 210-2 and the visual display 206. In embodiments, the receiving in real time may be effected at the device sampling frequency.

In embodiments, the machine executable code 2510, when executed by the one or more processors 2506-1, may perform the step of l) storing the second tracking data in the non-transitory memory 2508-1 associated with the first stimulus 204-1 (S2704). In embodiments, the machine executable code 2510, when executed by the one or more processors 2506-1, may perform the step of calibrating the eye-tracking device 208 for the second eye 210-2 based on the second gaze point information with regard to the stimulus information associated with the first stimulus 204-1 on the visual display 206. In embodiments, the calibrating step may be repeated periodically. In embodiments, the calibrating step is repeated aperiodically. In embodiments, the determining step d) may further include determining, for the first stimulus 204-1, the dynamic evidence-of-visibility score and the dynamic evidence-of-trackability score based at least on the second tracking data and the first stimulus information. In embodiments, the machine executable code 2510 for determining the dynamic evidence-of-visibility score and the dynamic evidence-of-trackability score may include:

```
trackability = a * position_pursuit_tracking +
b * trajectory_pursuit_tracking + c *
saccade_pursuit_tracking
# where a, b, and c are weight coefficients between 0 and 1
visibility = w * trackability + x * saccade_to_target -
y * saccade_away_from_target + z *
fixation_on_target
# where w, x, y, and z are weight coefficients between 0 and 1
TRACKABLE[stimulus] = trackability >= stimulus_trackability_threshold
VISIBLE[stimulus] = True = visibility >= stimulus_visibility_threshold
```

In embodiments, the dynamic evidence-of-visibility score may indicate a percentage of likelihood that the first stimulus 204-1 is visible to the at least one eye 210-1 and the second eye 210-2. In embodiments, the dynamic evidence-of-trackability may indicate a percentage of likelihood that the first stimulus 204-1 is tracked by the at least one eye 210-1 and the second eye 210-2.

In embodiments, the machine executable code 2510, when executed by the one or more processors 2506-1, may perform the step of m) storing, in the non-transitory memory 2508-1 associated with the first stimulus 204-1: i) the dynamic evidence-of-visibility score; and ii) the dynamic evidence-of-trackability score (S2706). In embodiments, the machine executable code 2510, when executed by the one or more processors 2506-1, may perform the step of n) analyzing the stored second tracking data to determine a presence of one or more of fixation eye movement(s), saccade eye movement(s), smooth pursuit eye movement(s), optokinetic nystagmus eye movement(s), and blink eye movement(s) (S2708). In embodiments, analyzing the stored second tracking data to determine a presence of fixation eye movement(s) may include:

```
dispersion = hypot(mean(get_gaze_dx( )), mean(get_gaze_dy( ))
if dispersion <= max_fixation_dispersion:
    FIXATION_ACTIVE = True
elif FIXATION_ACTIVE:
    FIXATION_ACTIVE = False
```

In embodiments, analyzing the stored second tracking data to determine a presence of saccade eye movement(s) may include:

```
if min_saccade_speed <= get_gaze_speed( ) <= max_saccade_speed:
    if get_gaze_point( ) in get_previous_saccade_path( ):
        SACCADE_ACTIVE = False
    elif get_gaze_angle_change( ) > max_saccade_angle_change:
        SACCADE_ACTIVE = False
    else:
        SACCADE_ACTIVE = True
else:
    SACCADE_ACTIVE = False
```

In embodiments, analyzing the stored second tracking data to determine a presence of smooth pursuit eye movement(s) may include:

```
if min_pursuit_speed <= get_gaze_speed( ) <= max_pursuit_speed:
    if get_gaze_angle_change( ) > max_pursuit_angle_change:
        PURSUIT_ACTIVE = False
    elif hypot(get_gaze_dx( ), get_gaze_dy( )) >= max_pursuit_delta:
        PURSUIT_ACTIVE = False
    else:
        PURSUIT_ACTIVE = True
else:
    PURSUIT_ACTIVE = False
```

In embodiments, the analyzing step may further include determining a mean gaze point value over a sliding time window during the second predetermined amount of time, wherein fixation movement is determined when the mean gaze value exceeds a first threshold. In embodiments, the analyzing step may further include determining a gaze point velocity, including a magnitude and angle, over the sliding time window during the second amount of time. In embodiments, saccade eye movement may be determined when a magnitude of the gaze point velocity exceeds the second predetermined threshold and remains above the second predetermined threshold for the first threshold period of time. In embodiments, the analyzing step may further include determining whether a change in the gaze velocity angle changes by more than 90 degrees between two successive time windows. In embodiments, the change in the gaze velocity angle may range from 45 degrees to 135 degrees. In embodiments, the analyzing step may further include determining a gaze point velocity, including a magnitude and angle, and a gaze point acceleration over the sliding time window during the second predetermined amount of time, wherein smooth pursuit eye movement is determined when the magnitude of the gaze point velocity falls within a first predetermined range and a rate of change of the gaze point velocity angle is below a predetermined third threshold value. In embodiments, the determining step may include accessing tracking information associated with a prior amount of time. In embodiments, the machine executable code 2510, when executed by the one or more processors 2506-1, may perform the steps for a second eye 210-2 of the subject 202.

In embodiments, the machine executable code 2510, when executed by the one or more processors 2506-1, may perform the step of o) analyzing the second tracking data obtained via the eye-tracking device 208 so as to determine, relative to the first stimulus 204-1, position-matched tracking eye movements, trajectory-matched tracking eye movements, and saccade-based tracking eye movements (S2710). In embodiments, the analyzing step o) may include comparing gaze position information over a sliding time window during the second predetermined amount of time to respective first stimulus location information associated with first stimulus time stamp information falling within the sliding time window, wherein position-matched tracking eye movements are identified when the gaze position is within a predetermined distance from the first stimulus location. In embodiments, the analyzing step may include comparing gaze position information over a sliding time window during the first predetermined amount of time to respective first stimulus location information associated with first stimulus time stamp information falling within the sliding time window, wherein trajectory matched tracking eye movements are identified when the distance between the first stimulus 204-1 and the adjusted gaze point of the eye 210-1 at each time stamp inside the sliding window is below a threshold determined by the properties of the stimulus, where the adjusted gaze point is obtained by subtracting the most recent deviation in position between the first stimulus and the gaze point of the eye obtained from the eye tracker 208. In embodiments, the analyzing step may further include determining a gaze point velocity, including a magnitude and angle, over the sliding time window during the first predetermined amount of time. In embodiments, saccade-based tracking eye movement may be determined when a magnitude of the gaze point velocity exceeds a third predetermined threshold and remains above the third predetermined threshold for a first threshold amount of time. In embodiments, saccade-based tracking eye movement may be identified when saccade eye movement is identified at a predetermined rate and persists for a fourth predetermined period of time. In embodiments, the first predetermined rate may be twice per second. In embodiments, the fourth predetermined time may be 2 seconds.

In embodiments, the second tracking data obtained via the eye-tracking device may include a gaze point and three-dimensional eye data. In embodiments, the process may be completed with one or both eyes. In embodiments, the process may be completed with the left eye. In embodiments, the process may be completed with the right eye. In embodiments, the process may be completed by both the right and the left eye, wherein the tracking data of both eyes is averaged to create a mean tracking data. The eye movement system is designed to have both eyes move in lock step in order to maintain a split of the monocular and binocular visual fields as the eyes move around. Therefore, for healthy adult individuals, it would not matter whether one or both eyes are tracked. In embodiments and in accordance with the present invention, however, by tracking both eyes, gaze may be better maintained if the tracker's view of one eye is disrupted. Further, in embodiments, by tracking each eye, it may be possible to gain quantitative evidence of an abnormality. In embodiments, where the eye is extremely deviated, if both eyes are tracked the eye tracker will not pick up the deviated eye and will only be able to use the non-deviated eye.

In embodiments, the machine executable code 2510, when executed by the one or more processors 2506-1, may perform the step of p) updating, in real time, the dynamic evidence-of-visibility score and/or the evidence-of-trackability score associated with the first stimulus (S2712) based on at least one of any eye movements detected in steps n) (S2708) and o) (S2710). In embodiments, the machine executable code 2510, when executed by the one or more processors 2506-1, may perform the step of q) updating in real time the appearance of the first stimulus 204-1 to provide the second stimulus 204-2 based on at least one of the updated evidence-of-visibility score and the updated evidence-of-trackability score for the first visual stimulus 204-1 (S2714).

Figure 28:
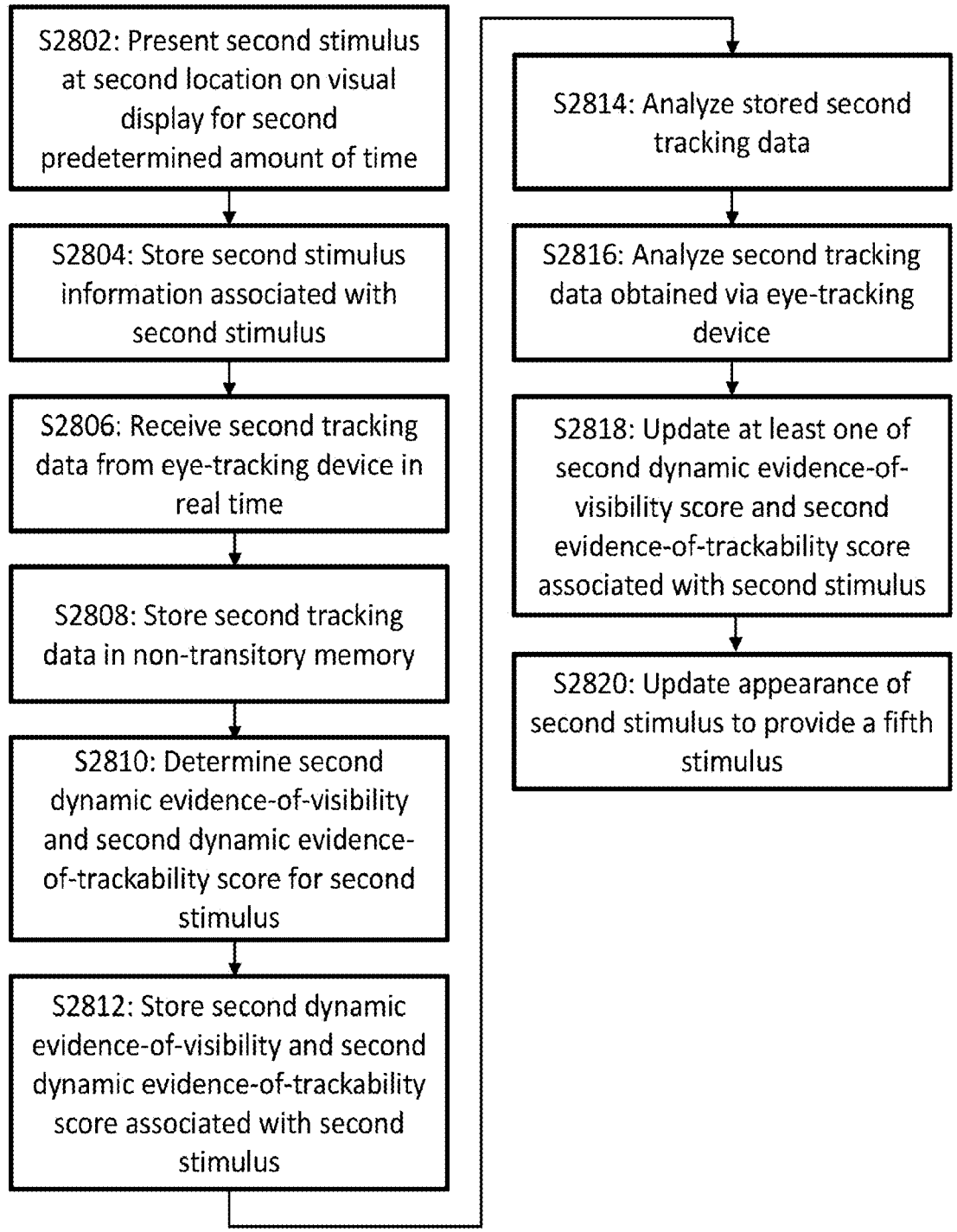
FIG. 28 is a schematic diagram of a process flow for evaluating contrast sensitivity and other visual metrics in accordance with another embodiment of the present invention.

FIG. 28 is a schematic diagram of a process flow for evaluating contrast sensitivity and other visual metrics in accordance with another embodiment of the present invention. In embodiments, the machine executable code 2510, when executed by the one or more processors 2506-1, may perform the step of k) presenting in real time for a second predetermined amount of time at least the second stimulus 204-2 at a second location on the visual display 206 (S2802). In embodiments, the second stimulus 204-2 may be the first stimulus 204-1. In embodiments, the second stimulus 204-2 may be different from the first stimulus 204-1. In embodiments, the presenting step may include presenting in real time for the second predetermined period of time a fourth stimulus 204-4 at a fourth location on the visual display 206. In embodiments, the machine executable code 2510, when executed by the one or more processors 2506-1, may perform the step of l) storing second stimulus information associated with the second stimulus 204-2 (S2804). In embodiments, the second stimulus information may include: i) second stimulus location information associated with the second location of the second stimulus 204-2 on the visual display 206 for the second predetermined amount of time; and ii) second stimulus time stamp information associated with the second stimulus location information. In embodiments, the second stimulus location information may be the same as the first stimulus location information. In embodiments, the second stimulus location information may be different from the first stimulus location information. In embodiments, the second stimulus information may include contrast, spatial frequency, color, and size.

In embodiments, the machine executable code 2510, when executed by the one or more processors 2506-1, may perform the step of m) receiving in real time, from the eye-tracking device 208, for the second predetermined amount of time, second tracking data (S2806). In embodiments, the second tracking data may include: i) second gaze point information associated with a second point on the visual display 206 to which the at least one eye 210-1 is directed during the second predetermined amount of time; ii) second position information associated with a 3D position of the at least one eye 210-1 over the second predetermined amount of time; and iii) second gaze point time stamp information associated with the second gaze point information and the second position information. In embodiments, the second gaze point information indicates a position of the second point on the visual display 206 to which the at least one eye 210-1 is directed in terms of degrees of visual angle relative to the center of the visual display during the second predetermined amount of time. In embodiments, the second gaze point information may indicate a direction of the second point on the visual display 206 to which the at least one eye 210-1 is directed relative to a center of the visual display 206 during the second predetermined amount of time. In embodiments, the second position information may indicate a distance between the at least one eye 210-1 and the visual display 206 during the second predetermined amount of time. In embodiments, the receiving in real time may be effected at the device sampling frequency.

In embodiments, the machine executable code 2510, when executed by the one or more processors 2506-1, may perform the step of n) storing the second tracking data in the non-transitory memory 2508-1 associated with the first stimulus 204-1 (S2808). In embodiments, the machine executable code 2510, when executed by the one or more processors 2506-1, may perform the step of calibrating the eye-tracking device 208 for the at least one eye 210-1 based on the second gaze point information with regard to the stimulus information associated with the first stimulus 204-1 on the visual display 206. In embodiments, the calibrating step may be repeated periodically. In embodiments, the calibrating step is repeated aperiodically. In embodiments, the machine executable code 2510, when executed by the one or more processors 2506-1, may perform the step of o) determining, for the second stimulus 204-2, a second dynamic evidence-of-visibility score and a second dynamic evidence-of-trackability score based at least on the second tracking data and the second stimulus information (S2810). In embodiments, the machine executable code 2510 for determining the second dynamic evidence-of-visibility score and the second dynamic evidence-of-trackability score may include:

```
trackability = a * position_pursuit_tracking +
b * trajectory_pursuit_tracking + c *
saccade_pursuit_tracking
# where a, b, and c are weight coefficients between 0 and 1
visibility = w * trackability + x * saccade_to_target −
y * saccade_away_from_target + z *
fixation_on_target
# where w, x, y, and z are weight coefficients between 0 and 1
TRACKABLE[stimulus] = trackability >= stimulus_trackability_threshold
VISIBLE[stimulus] = True = visibility >= stimulus_visibility_threshold
```

In embodiments, the second dynamic evidence-of-visibility score may indicate a percentage of likelihood that the second stimulus 204-2 is visible to the at least one eye 210-1. In embodiments, the second dynamic evidence-of-trackability may indicate a percentage of likelihood that the second stimulus 204-2 is tracked by the at least one eye 210-1.

In embodiments, the machine executable code 2510, when executed by the one or more processors 2506-1, may perform the step of p) storing, in the non-transitory memory 2508-1 associated with the second stimulus 204-2: i) the second dynamic evidence-of-visibility score; and ii) the second dynamic evidence-of-trackability score (S2812). In embodiments, the machine executable code 2510, when executed by the one or more processors 2506-1, may perform the step of q) analyzing the stored second tracking data to determine a presence of one or more of fixation eye movement(s), saccade eye movement(s), smooth pursuit eye movement(s), and blink eye movement(s) (S2814). In embodiments, analyzing the stored second tracking data to determine a presence of fixation eye movement(s) may include:

```
dispersion = hypot(mean(get_gaze_dx( )), mean(get_gaze_dy( ))
if dispersion <= max_fixation_dispersion:
    FIXATION_ACTIVE = True
elif FIXATION_ACTIVE:
    FIXATION_ACTIVE = False
```

In embodiments, analyzing the stored second tracking data to determine a presence of saccade eye movement(s) may include:

```
if min_saccade_speed <= get_gaze_speed( ) <= max_saccade_speed:
    if get_gaze_point( ) in get_previous_saccade_path( ):
        SACCADE_ACTIVE = False
    elif get_gaze_angle_change( ) > max_saccade_angle_change:
        SACCADE_ACTIVE = False
    else:
        SACCADE_ACTIVE = True
else:
    SACCADE_ACTIVE = False
```

In embodiments, analyzing the stored second tracking data to determine a presence of smooth pursuit eye movement(s) may include:

```
if min_pursuit_speed <= get_gaze_speed( ) <= max_pursuit_speed:
    if get_gaze_angle_change( ) > max_pursuit_angle_change:
        PURSUIT_ACTIVE = False
    elif hypot(get_gaze_dx( ), get_gaze_dy( )) >= max_pursuit_delta:
        PURSUIT_ACTIVE = False
    else:
        PURSUIT_ACTIVE = True
else:
    PURSUIT_ACTIVE = False
```

In embodiments, the analyzing step may further include determining a mean gaze point value over a sliding time window during the second predetermined amount of time, wherein fixation movement is determined when the mean gaze value exceeds a first threshold. In embodiments, the analyzing step may further include determining a gaze point velocity, including a magnitude and angle, over the sliding time window during the second amount of time. In embodiments, saccade eye movement may be determined when a magnitude of the gaze point velocity exceeds the second predetermined threshold and remains above the second predetermined threshold for the first threshold period of time. In embodiments, the analyzing step further comprises determining whether a change in the gaze velocity angle changes by more than 90 degrees between two successive time windows. In embodiments, the change in the gaze velocity angle may range from 45 degrees to 135 degrees. In embodiments, the analyzing step may further include determining a gaze point velocity, including a magnitude and angle, and a gaze point acceleration over the sliding time window during the second predetermined amount of time, wherein smooth pursuit eye movement is determined when the magnitude of the gaze point velocity falls within a first predetermined range and a rate of change of the gaze point velocity angle is below a predetermined third threshold value. In embodiments, blink eye movement may be identified when there is no gaze point information for a first period of time. In embodiments, the determining step may include accessing tracking information associated with a prior amount of time.

In embodiments, the machine executable code 2510, when executed by the one or more processors 2506-1, may perform the step of r) analyzing the second tracking data obtained via the eye-tracking device 208 so as to, for the at least one eye 210-1, relative to the second stimulus 204-2, determine: position-matched tracking eye movements, trajectory-matched tracking eye movements, and saccade-based tracking eye movements (S2816). In embodiments, the analyzing step r) may include comparing gaze position information over a sliding time window during the second predetermined amount of time to respective second stimulus location information associated with second stimulus time stamp information falling within the sliding time window, wherein position-matched tracking eye movements are identified when the gaze position is within a predetermined distance from the first stimulus location. In embodiments, the step of analyzing the second tracking data may include comparing gaze position information over a sliding time window during the second predetermined amount of time to respective second stimulus location information associated with second stimulus time stamp information falling within the sliding time window, wherein trajectory matched tracking eye movements are identified when the distance between the second stimulus 204-2 and the adjusted gaze point of the eye at each time stamp inside the sliding window is below a threshold determined by the properties of the stimulus 204-2, where the adjusted gaze point is obtained by subtracting the most recent deviation in position between the second stimulus 204-2 and the gaze point of the eye obtained from the eye tracker 208. In embodiments, the step of analyzing the second tracking data may further include determining a gaze point velocity, including a magnitude and angle, over the sliding time window during the second predetermined amount of time. In embodiments, saccade eye movement may be determined when a magnitude of the gaze point velocity exceeds a third predetermined threshold and remains above the third predetermined threshold for a first threshold amount of time. In embodiments, saccade-based tracking movement may be identified when saccade eye movement is identified at a predetermined rate and persists for a fourth predetermined period of time. In embodiments, the first predetermined rate may be, for example, twice per second. In embodiments, the fourth predetermined time may be, for example, 2 seconds.

In embodiments, the machine executable code 2510, when executed by the one or more processors 2506-1, may perform the step of s) updating, in real time, at least one of the second dynamic evidence-of-visibility score and the second evidence-of-trackability score associated with the second stimulus 204-2 (S2818) based on at least one of any eye movements detected in step q) (S2814) and step r) (S2816). In embodiments, the machine executable code 2510, when executed by the one or more processors 2506-1, may perform the step of t) updating in real time the appearance of the second stimulus 204-2 to provide a fifth stimulus 204-5 based on at least one of the updated second evidence-of-visibility score and the updated second evidence-of-trackability score for the second stimulus 204-2 (S2820).

In embodiments, the machine executable code 2510, when executed by the one or more processors 2506-1, may perform the step of updating in real time, for the at least one eye 210-1 and the second eye 210-2, the calibration of the eye-tracking device based on the evidence-of-visibility score(s) or evidence-of-trackability score(s) of one or more visual stimuli 204-1.

In embodiments, the machine executable code 2510, when executed by the one or more processors 2506-1, may perform the step of presenting auditory or tactile stimuli to the subject 202 based on the evidence-of-visibility score(s) or evidence-of-trackability score(s) of at least one or the at least one stimulus 204-1 and the second stimulus 204-2. In embodiments, the machine executable code 2510, when executed by the one or more processors 2506-1, may perform the step of determining, in real time, an estimate of the subject's attentiveness, fatigue level, and/or ability based on the evidence-of-visibility score(s) or evidence-of-trackability score(s).

Examples of how the systems and methods of the disclosure can be used are set forth below in non-limiting embodiments:

Visual Metrics

Visibility: the invention can be used for rapid and quantitative measures of visual thresholds. That is, once evidence of seeing is established through evidence of tracking, the visibility of visual stimuli can be adjusted rapidly (up to once per frame) until evidence of seeing (via tracking) falls below a criterion, which would identify the limit (threshold) of ability to see the stimulus. This approach can be used to establish the threshold ability to see any property of a visual stimulus, including (but not limited to) size, luminance, contrast, color, motion, speed, orientation, direction, form, or visual field location. The stimulus conditions can also be altered to identify stimulus visibility by rapidly manipulating the testing context through auditory (e.g., pitch, volume, pattern), haptic (e.g., intensity or pattern of vibrations), or visual (e.g., number of visual elements, background features) changes accompanying a stimulus alone or in combination. Such contextual manipulations can be used to identify thresholds for visual crowding, feature analysis, etc.

Visual Prosthetics

Trackability: the invention can be used to act quickly upon knowledge of altered trackability by correcting for stimulus movement in subjects with abnormal function or who exhibit abnormal tracking behavior, including (but not limited to) impaired tracking smoothness, nystagmus, visual field deficit (e.g., hemifield neglect, hemianopsia, progressive supranuclear palsy, etc.) to make the information visible or more salient.

Improved Calibration

Visibility/Trackability: the invention can be used to update in real time the calibration of the eye tracking devices that are used to assess tracking in response to the system's estimate of where and how an observer is tracking visible stimuli.

Enhanced Gaming/Interface Control

Visibility/Trackability: the invention can be used to control actions within a video game or computer interface by using real-time knowledge of stimulus trackability and visibility. Contextual game mechanics can be activated by established trackability or visibility of a given type and/or weight, such as controlling the character, casting spells, responding to opponents' actions, and changing the appearance of the game (textures, lighting, etc.). Game menus or menus of other software interfaces can also respond to the system's trackability and/or visibility metrics to create eye tracker-based user experiences that are superior to interfaces based solely on gaze fixation. For example, elements of a moving menu overlay may only be triggered if the system determines they are being tracked, with fixation alone not being sufficient, in order to avoid false positives from fixation on an underlying target.

Visibility/Trackability: the invention can be used to dynamically set the difficulty and/or entertainment value of a game for a specific player based on knowledge of stimulus trackability and/or visibility. This knowledge may include estimates of player fatigue, awareness of visual elements, latency between stimulus appearance and visibility, an estimate of current eye tracker calibration quality, etc. Difficulty and/or entertainment value may be dynamically updated as evidence of trackability and visibility of game elements varies in real time in order to maximize player engagement or perceived challenge.

Visibility/Trackability: the invention can be used to adjust the trackability or visibility of stimuli in a task around the limit of a subject's ability to engage neural plasticity that could be used to improve the performance of athletes, gamers, subjects recovering from injury, etc. in seeing and acting upon moving visual information.

Visibility/Trackability: eye trackers may be embedded in the dashboard of planes, cars, tanks, etc. or in head-mounted video devices to monitor in real time the ability of pilots, drivers, observers, etc. to see and act upon moving visual information. Such measures could be used to grade the preparedness of individuals to do a job (e.g., to select for best ability among a group of job candidates), determine the minimum ability to do a job (e.g., for screening applicants), to identify the ability to operate a motor vehicle or other complicated task that requires skill that surpasses a certain criterion, or to distinguish when an individual has fallen below the minimum competence do a job or complete a task (e.g., remove users from a task if they are fatigued or otherwise impaired to function in a job that requires a high level of ability to track visual information and act upon it competently).

Advertising/Entertainment

Visibility and trackability: the invention can be used to monitor stimulus visibility and trackability in focus groups during the evaluation of commercials, video presentations of shelf items, during movie or other video-based content, or any other visually-driven commercial experience to evaluate the saliency of information, viewer attention over time, etc., or as a means of gaining feedback to improve the information content or 'stickiness' of visual information.

While the invention has been described in detail with reference to embodiments for the purposes of making a complete disclosure of the invention, such embodiments are merely exemplary and are not intended to be limiting or represent an exhaustive enumeration of all aspects of the invention. It will be apparent to those of ordinary skill in the art that numerous changes may be made in such details, and the invention is capable of being embodied in other forms, without departing from the spirit, essential characteristics, and principles of the invention. Also, the benefits, advantages, solutions to problems, and any elements that may allow or facilitate any benefit, advantage, or solution are not to be construed as critical, required, or essential to the invention. The scope of the invention is to be limited only by the appended claims.

What is claimed is:

1. A system for dynamically assessing a visual function of a subject, comprising:
   i) a visual display;
   ii) an eye-tracking device configured to detect a gaze position of at least one eye of the subject;
   iii) one or more processors operably connected to the visual display and the eye-tracking device;
   iv) a non-transitory memory operably connected to the one or more processors and including machine executable code that when executed by the one or more processors performs the steps of:

a) presenting for a first defined amount of time a first stimulus at a first location on the visual display;
b) storing first stimulus information associated with the first stimulus, the first stimulus information including:
   i. first stimulus location information associated with a location of the first stimulus on the visual display for the first predetermined amount of time; and
   ii. first stimulus time stamp information associated with the first stimulus location information;
c) receiving in real time, from the eye-tracking device, for the predetermined amount of time, first tracking data comprising:
   i. first gaze point information associated with a first point on the visual display to which the eye is directed during the predetermined amount of time;
   ii. first position information associated with a 3D position of the eye over the predetermined amount of time; and
   iii. first gaze point time stamp information associated with the gaze point information and the position information;
d) storing the first tracking data in the non-transitory memory associated with the first stimulus;
e) determining, for the first stimulus, a dynamic evidence-of-visibility score and a dynamic evidence-of-trackability score based at least on the tracking data and the first stimulus information;
f) storing in the non-transitory memory, associated with the first stimulus:
   i. the dynamic evidence-of-visibility score; and
   ii. the dynamic evidence-of-trackability score;
g) analyzing the stored first tracking data to determine a presence of one or more of:
   i. fixation eye movement(s);
   ii. saccade eye movement(s);
   iii. smooth pursuit eye movement(s); and
   iv. blink(s);
h) analyzing the first tracking data obtained via the eye-tracking device to identify for the eye, relative to the first stimulus:
   i. position-matched tracking eye movements;
   ii. trajectory-matched tracking eye movements; and
   iii. saccade-based tracking eye movements;
i) updating, in real time, the dynamic evidence-of-visibility score and/or the evidence-of-trackability score associated with the first stimulus based on at least one of any eye movements detected in step g) and step h); and
j) updating in real time the appearance of the first stimulus to provide a second stimulus based on at least one of the updated evidence-of-visibility score and the updated evidence-of-trackability score for the first visual stimulus.

2. The system of claim 1, wherein the performing step includes presenting in real time for the first defined period of time a second stimulus at a second location on the visual display.

3. The system of claim 1, wherein the first stimulus information comprises contrast, spatial frequency, color, and size.

4. The system of claim 1, wherein the first gaze point information indicates a position of the first point on the visual display to which the eye is directed in units of degrees of visual angle relative to the center of the visual display.

5. The system of claim 4, wherein the first gaze point information indicates a direction of the point on the visual display to which the eye is directed relative to the center of the visual display.

6. The system of claim 1, wherein the first position information indicates a distance between the eye and the visual display.

7. The system of claim 1, wherein the receiving in real time is effected at the device sampling frequency.

8. The system of claim 1, wherein the machine executable code, when executed by the one or more processors, performs the step of calibrating the eye-tracking device for the eye based on the gaze point information and the stimulus information associated with the first stimulus on the visual display.

9. The system of claim 8, wherein the calibrating step is repeated periodically.

10. The system of claim 8, wherein the calibrating step is repeated aperiodically.

11. The system of claim 1, wherein the dynamic evidence-of-visibility score indicates a percentage of likelihood that the first stimulus is visible to the eye.

12. The system of claim 1, wherein the dynamic evidence-of-trackability indicates a percentage of likelihood that the first stimulus is tracked by the eye.

13. The system of claim 1, wherein the analyzing step further comprises determining a mean gaze point value over a sliding time window during the first defined amount of time.

14. The system of claim 1, wherein the analyzing step further comprises determining a gaze point velocity, including a magnitude and angle, over the sliding time window during the first amount of time.

15. The system of claim 14, wherein saccade eye movement is determined when a magnitude of the gaze point velocity exceeds a second predetermined threshold and remains above the second predetermined threshold for a first threshold period of time.

16. The system of claim 14, wherein the analyzing step further comprises determining whether a change in the gaze velocity angle changes by more than 90 degrees between two successive time windows.

17. The system of claim 1, wherein the analyzing step further comprises determining a gaze point velocity, including a magnitude and angle, and a gaze point acceleration over the sliding time window during the first predetermined amount of time, wherein smooth pursuit eye movement is determined when the magnitude of the gaze point velocity falls within a first predetermined range and a rate of change of the gaze point velocity angle is below a predetermined third threshold value.

18. The system of claim 1, wherein blink eye movement is identified when there is no gaze point information for a first period of time.

19. The system of claim 1, wherein the determining step includes accessing prior tracking information.

20. A method for dynamically assessing a visual function of a subject, comprising assessing the subject's visual function in one or both eyes of the subject with the system of claim 1.

* * * * *